（12） United States Patent
Okada et al.

(10) Patent No.: US 10,035,129 B2
(45) Date of Patent: Jul. 31, 2018

(54) OXYGEN-ABSORBING RESIN COMPOSITION AND OXYGEN-ABSORBING MOLDED ARTICLE USING SAME AND MULTILAYER BODY, CONTAINER, INJECTION-MOLDED ARTICLE AND MEDICAL CONTAINER USING THESE

(71) Applicant: MITSUBISHI GAS CHEMICAL COMPANY, INC., Tokyo (JP)

(72) Inventors: Satoshi Okada, Kanagawa (JP); Toshiya Takagi, Kanagawa (JP); Takashi Kashiba, Kanagawa (JP); Shinpei Iwamoto, Kanagawa (JP); Shinichi Ikeda, Kanagawa (JP); Fumihiro Ito, Kanagawa (JP); Shun Ogawa, Kanagawa (JP); Shota Arakawa, Kanagawa (JP); Kenichiro Usuda, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 348 days.

(21) Appl. No.: 14/360,078

(22) PCT Filed: Nov. 22, 2012

(86) PCT No.: PCT/JP2012/080395
§ 371 (c)(1),
(2) Date: May 22, 2014

(87) PCT Pub. No.: WO2013/077436
PCT Pub. Date: May 30, 2013

(65) Prior Publication Data
US 2014/0308405 A1    Oct. 16, 2014

(30) Foreign Application Priority Data

| Nov. 25, 2011 | (JP) | 2011-257821 |
|---|---|---|
| Oct. 5, 2012 | (JP) | 2012-223276 |
| Oct. 10, 2012 | (JP) | 2012-224914 |
| Oct. 15, 2012 | (JP) | 2012-228313 |
| Oct. 16, 2012 | (JP) | 2012-228749 |
| Oct. 16, 2012 | (JP) | 2012-229009 |
| Oct. 19, 2012 | (JP) | 2012-231635 |
| Oct. 19, 2012 | (JP) | 2012-231636 |
| Oct. 19, 2012 | (JP) | 2012-231790 |
| Oct. 24, 2012 | (JP) | 2012-235091 |
| Oct. 24, 2012 | (JP) | 2012-235092 |
| Oct. 25, 2012 | (JP) | 2012-235248 |
| Oct. 25, 2012 | (JP) | 2012-235249 |
| Oct. 25, 2012 | (JP) | 2012-235409 |
| Oct. 29, 2012 | (JP) | 2012-237569 |
| Oct. 30, 2012 | (JP) | 2012-238926 |
| Oct. 30, 2012 | (JP) | 2012-238927 |
| Oct. 30, 2012 | (JP) | 2012-238928 |
| Oct. 30, 2012 | (JP) | 2012-238929 |

(51) Int. Cl.
C08K 5/098    (2006.01)
C08G 63/181   (2006.01)
(Continued)

(52) U.S. Cl.
CPC .......... B01J 20/264 (2013.01); A23L 3/3436 (2013.01); A61M 5/3129 (2013.01); B01J 20/28042 (2013.01); B01J 20/3007 (2013.01); B32B 1/02 (2013.01); B32B 7/12 (2013.01); B32B 15/085 (2013.01); B32B 15/09 (2013.01); B32B 15/20 (2013.01); B32B 27/08 (2013.01);
(Continued)

(58) Field of Classification Search
CPC ...... B01D 2253/1122; B01D 2253/202; B01D 2253/25; B01D 2257/104; B01D 53/02; C08G 63/181; C08G 63/19; C08G 63/64; C08K 5/098; C08L 67/00; C08L 23/00; C08L 67/02; C08J 2323/08; C08J 2367/02; C08J 2423/08; C08J 2467/02; C08J 5/18
See application file for complete search history.

(56) References Cited

U.S. PATENT DOCUMENTS 3,505,282 A    4/1970  Storms et al.
5,021,515 A    6/1991  Cochran et al.
(Continued)

FOREIGN PATENT DOCUMENTS

EP    0 850 967    1/1998
JP    07-079702    3/1995
(Continued)

OTHER PUBLICATIONS

Search report from PCT/JP2012/080395, dated Jan. 15, 2013.

*Primary Examiner* — Ling Choi
*Assistant Examiner* — Gennadiy Mesh
(74) *Attorney, Agent, or Firm* — Greenblum & Bernstein, P.L.C.

(57) ABSTRACT

Oxygen-absorbing resin composition, not responsive to a metal detector, producing no odor after absorption of oxygen and has excellent oxygen-absorbing performance in a wide range of humidity conditions from low to high humidity. An oxygen-absorbing molded article, and a multilayer body, container, injection-molded article and medical containers also provided. The oxygen absorbing resin composition contains a polyester, comprising at least one constituent unit having a tetralin ring component compound, a transition metal catalyst, and a catalyst for producing the polyester. The oxygen-absorbing molded article of the present invention can be formed by molding the oxygen-absorbing resin composition into a film or a sheet. The multilayer body, container, injection-molded article, medical container, etc. of the present invention are obtained by using the oxygen-absorbing resin composition.

28 Claims, No Drawings

(51) Int. Cl.

| | | |
|---|---|---|
| *B32B 27/32* | (2006.01) | |
| *C08G 63/19* | (2006.01) | |
| *B01J 20/26* | (2006.01) | |
| *A23L 3/3436* | (2006.01) | |
| *A61M 5/31* | (2006.01) | |
| *B32B 7/12* | (2006.01) | |
| *B32B 15/085* | (2006.01) | |
| *B32B 15/09* | (2006.01) | |
| *B32B 15/20* | (2006.01) | |
| *B32B 27/08* | (2006.01) | |
| *B32B 27/10* | (2006.01) | |
| *B32B 27/16* | (2006.01) | |
| *B32B 27/18* | (2006.01) | |
| *B32B 27/30* | (2006.01) | |
| *B32B 27/34* | (2006.01) | |
| *B32B 27/36* | (2006.01) | |
| *B32B 29/06* | (2006.01) | |
| *B32B 1/02* | (2006.01) | |
| *C08J 5/18* | (2006.01) | |
| *C08G 63/64* | (2006.01) | |
| *C08L 67/00* | (2006.01) | |
| *B01J 20/28* | (2006.01) | |
| *B01J 20/30* | (2006.01) | |
| *B65D 85/72* | (2006.01) | |
| *A61J 1/06* | (2006.01) | |
| *A61J 1/10* | (2006.01) | |

(52) U.S. Cl.
CPC ............ *B32B 27/10* (2013.01); *B32B 27/16* (2013.01); *B32B 27/18* (2013.01); *B32B 27/306* (2013.01); *B32B 27/32* (2013.01); *B32B 27/325* (2013.01); *B32B 27/327* (2013.01); *B32B 27/34* (2013.01); *B32B 27/36* (2013.01); *B32B 27/365* (2013.01); *B32B 29/06* (2013.01); *B65D 85/72* (2013.01); *C08G 63/181* (2013.01); *C08G 63/19* (2013.01); *C08G 63/64* (2013.01); *C08J 5/18* (2013.01); *C08K 5/098* (2013.01); *C08L 67/00* (2013.01); *A61J 1/065* (2013.01); *A61J 1/067* (2013.01); *A61J 1/10* (2013.01); *B32B 2250/02* (2013.01); *B32B 2250/03* (2013.01); *B32B 2250/04* (2013.01); *B32B 2250/05* (2013.01); *B32B 2250/24* (2013.01); *B32B 2250/40* (2013.01); *B32B 2255/10* (2013.01); *B32B 2255/20* (2013.01); *B32B 2270/00* (2013.01); *B32B 2307/31* (2013.01); *B32B 2307/518* (2013.01); *B32B 2307/718* (2013.01); *B32B 2307/724* (2013.01); *B32B 2307/7244* (2013.01); *B32B 2307/738* (2013.01); *B32B 2439/46* (2013.01); *B32B 2439/60* (2013.01); *B32B 2439/62* (2013.01); *B32B 2439/70* (2013.01); *B32B 2439/80* (2013.01); *C08J 2323/08* (2013.01); *C08J 2367/02* (2013.01); *C08J 2423/08* (2013.01); *C08J 2467/02* (2013.01); *Y10T 428/1303* (2015.01); *Y10T 428/1355* (2015.01); *Y10T 428/1359* (2015.01); *Y10T 428/31678* (2015.04)

(56) References Cited

U.S. PATENT DOCUMENTS

| | | | |
|---|---|---|---|
| 5,346,644 | A | 9/1994 | Speer et al. |
| 5,350,622 | A | 9/1994 | Speer et al. |
| 5,529,833 | A | 6/1996 | Speer |
| 5,639,815 | A | 6/1997 | Cochran et al. |
| 5,700,554 | A | 12/1997 | Speer et al. |
| 5,955,527 | A | 9/1999 | Cochran et al. |
| 6,063,503 | A | 5/2000 | Hatakeyama et al. |
| 6,124,043 | A | 9/2000 | Tsukamoto et al. |
| 6,254,803 | B1 | 7/2001 | Cochran et al. |
| 6,254,804 | B1 | 7/2001 | Matthews et al. |
| 6,527,976 | B1 * | 3/2003 | Cai .................. C08K 5/098 252/188.28 |
| 6,653,440 | B2 * | 11/2003 | Hirokane .......... C08G 63/16 528/272 |
| 2003/0068455 | A1 * | 4/2003 | Oguro .............. C08L 67/02 428/35.7 |
| 2004/0267194 | A1 | 12/2004 | Sano et al. |
| 2010/0106096 | A1 | 4/2010 | Hirokane et al. |

FOREIGN PATENT DOCUMENTS

| | | |
|---|---|---|
| JP | 07-112949 | 5/1995 |
| JP | 08-127641 | 5/1996 |
| JP | 08-134194 | 5/1996 |
| JP | 9-234832 | 9/1997 |
| JP | 2001-105540 | 4/2001 |
| JP | 2001-252560 | 9/2001 |
| JP | 2004-229750 | 8/2004 |
| JP | 2008-037065 | 2/2008 |
| JP | 2009-108153 | 5/2009 |
| WO | 2008/075639 | 6/2008 |

* cited by examiner

OXYGEN-ABSORBING RESIN COMPOSITION AND OXYGEN-ABSORBING MOLDED ARTICLE USING SAME AND MULTILAYER BODY, CONTAINER, INJECTION-MOLDED ARTICLE AND MEDICAL CONTAINER USING THESE

TECHNICAL FIELD

The present invention relates to an oxygen-absorbing resin composition, particularly to an oxygen-absorbing resin composition at least containing a polyester compound having a tetralin ring and a transition metal catalyst and an oxygen-absorbing molded article etc. using the same. The present invention also relates to a multilayer body, containers, etc. excellent in oxygen barrier performance and oxygen-absorbing performance in a wide range of humidity conditions from low humidity to high humidity. The present invention further relates to an injection-molded article and a medical container having oxygen barrier performance and oxygen-absorbing function as well as articles obtained by secondary processing of the injection-molded article.

BACKGROUND ART

In order to prevent oxygen oxidation and store various types of articles, represented by foods, beverages, medicinal products, cosmetics, etc., which easily deteriorate or degrade under the effect of oxygen for a long time, oxygen absorbents are used for removing oxygen within packaging bodies storing these articles.

As the oxygen absorbent, an oxygen absorbent containing an iron powder as a reactive main component is generally used in view of oxygen-absorbing ability, handling and safety. However, the iron-based oxygen absorbent is responsive to a metal detector and thus it is difficult to use a metal detector in inspecting foreign matter. Furthermore, packaging bodies containing an iron-based oxygen absorbent have a risk of ignition, and thus, they cannot be heated by a microwave oven. Moreover, the oxidation reaction of an iron powder requires water, and thus, an oxygen-absorbing effect is exerted only on an article to be packaged rich in moisture content.

Packaging containers are developed by making the container of a multilayer material having an oxygen-absorbing layer formed of an oxygen-absorbing resin composition containing a thermoplastic resin and an iron-based oxygen absorbent, thereby improving a gas barrier property of the container and providing an oxygen-absorbing function to the container itself (see, Patent Literature 1). To describe more specifically, the oxygen-absorbing multilayer film is used in the form having an oxygen-absorbing layer, which is optionally a thermoplastic resin layer having an oxygen absorbent dispersed in an intermediate layer formed of a thermoplastic resin, between layers of a conventional gas barrier multilayer film formed by stacking a heat sealing layer and a gas barrier layer, thereby adding a function of absorbing oxygen within the container to a function of preventing oxygen transmission from outside, and is manufactured by use of a conventional manufacturing method known in the art such as extrusion lamination, coextrusion lamination and dry lamination. However, such an oxygen-absorbing multilayer film has the same problems: a metal detector for inspecting foreign matter for foods etc. cannot be used; heating cannot be made by a microwave oven; and the effect is only exerted on an article to be packaged rich in moisture content. In addition, the multilayer film has a problem of opacity, leading to insufficient visibility of content. A multilayer film using an oxygen absorbent such as an iron powder, has problems: the film is detected by a metal detector used in inspection of foreign matter in foods etc.; the film is opaque, leading to insufficient visibility of content; and if an alcohol beverage is contained, iron reacts with alcohol to produce aldehyde, reducing taste and flavor.

In the aforementioned circumstances, it has been desired to develop an oxygen absorbent containing an organic substance as a reactive main component. As the oxygen absorbent containing an organic substance as a reactive main component, an oxygen absorbent containing ascorbic acid as a main component is known (see, Patent Literature 2).

In the meantime, an oxygen-absorbing resin composition composed of a resin and a transition metal catalyst is known. For example, a resin composition composed of a polyamide as an oxidizable organic component (in particular, a xylylene group-containing polyamide) and a transition metal catalyst, is known (see, Patent Literatures 3 and 4). In Patent Literatures 3 and 4, articles obtained by molding such a resin composition, such as an oxygen absorbent, a packaging material and a multilayer laminated film for packaging are further exemplified.

As an oxygen-absorbing resin composition requiring no moisture content for absorbing oxygen, an oxygen-absorbing resin composition composed of a resin having a carbon-carbon unsaturated bond and a transition metal catalyst, is known (see, Patent Literature 5).

As a composition for trapping oxygen, a composition composed of a polymer containing a substituted cyclohexene functional group or a low molecular-weight substance bound with the cyclohexene ring and a transition metal is known (see, Patent Literature 6).

In the meantime, injection molding, by which molded articles having a complicate-shape can be manufactured in a high yield, has been used for manufacturing a wide variety of products including machine parts, automotive parts, electric/electronic parts, containers for foods or medical products, etc. Recently, as packaging containers, variety types of plastic containers have been widely used because they have advantages of light-weight, transparency, moldability, etc. As a typical plastic container for a beverage, an injection-molded article having a screw thread cutting on the bottle neck designed to sufficiently screw the lid, has been frequently used.

As a material for use in injection-molded articles, general thermoplastic resins such as a polyolefin (polyethylene, polypropylene, etc.), a polyester and a polystyrene are mentioned. Particularly, injection-molded articles mainly formed of a polyester such as polyethylene terephthalate (PET) are used in a wide variety of plastic containers for beverages such as tea, fruit juice beverages, carbonated beverages and alcohol beverages. However, although an injection-molded article mainly formed of a thermoplastic resin is excellent as a packaging material, oxygen tends to easily transmit from the outside, unlike glass bottles and metal containers. Thus, even if a content is packed and hermetically closed therein, the storage stability of the content is still questioned. Accordingly, injection-molded articles having a gas barrier layer as an intermediate layer in order to provide a gas barrier property to such injection-molded articles composed of a general resin have been put into practical use.

In the meantime, as medical packaging containers for packaging and storing a drug solution in a sealed condition, glass ampoules, vials, prefilled syringes, etc. have been conventionally used. However, these glass containers have problems: sodium ion etc. elute off from the container to a liquid content stored therein; and micro substances called flakes generate; when a light-blocking glass container colored with a metal is used, the content is contaminated with the coloring metal; and the container is easily broken by drop impact. In addition to these problems, since glass containers have a relatively large specific gravity, medical packaging containers become heavy. For these reasons, development of alternate materials has been desired. To be more specific, materials lighter than glass, such as a polyester, a polycarbonate, a polypropylene and a cycloolefin polymer, have been investigated as glass alternatives.

For example, a medical container formed of a polyester resin material is proposed (see, Patent Literature 7).

In the meantime, a multilayer container having a gas barrier layer as an intermediate layer in order to provide a gas barrier property to a container made of plastic, has been investigated. Specifically, a prefilled syringe improved in oxygen barrier property by constituting the innermost layer and the outermost layer formed of a polyolefin resin and an intermediate layer formed of a resin composition excellent in oxygen barrier property is proposed (see, Patent Literature 8). Other than this, multilayer containers obtained by laminating a gas barrier layer formed of e.g., a polyamide (hereinafter, sometimes referred to as "nylon MXD6"), which is obtained from metaxylylenediamine and adipic acid, an ethylene-vinyl alcohol copolymer, a polyacrylonitrile, a poly(vinylidene chloride), an aluminum foil, a carbon coat or a vapor-deposited inorganic oxide, on a resin layer, have been investigated.

In recent years, it has been proposed that a small amount of transition metal compound is added to nylon MXD6 and mixed to provide an oxygen-absorbing function and the resultant material is used as an oxygen barrier material constituting containers and packaging materials (see, Patent Literature 9).

As a method for improving storage stability of foods etc. and preventing degradation of taste and flavor thereof, a technique of charging a deoxidized nitrogen gas in a package is known. In the technique, a metal can or a glass bottle is filled with e.g., an alcohol beverage such as sake, wine and shochu, a fruit juice, a vegetable juice, a broth or a tea beverage, and then, filled with nitrogen gas and sealed. However, metal cans and glass bottles inevitably have a problem of a non-combustible waste treatment. In addition, reducing weight is still demanded. Particularly when a metal can is used, elution of a metal component into the content is a problem. Because of this, alternation of metal cans and glass bottles to plastic containers such as a gas barrier multilayer container, has been widely investigated also in the food fields.

CITATION LIST

Patent Literatures

Patent Literature 1: Japanese Patent Laid-Open No. 9-234832
Patent Literature 2: Japanese Patent Laid-Open No. 51-136845
Patent Literature 3: Japanese Patent Laid-Open No. 2001-252560
Patent Literature 4: Japanese Patent Laid-Open No. 2009-108153
Patent Literature 5: Japanese Patent Laid-Open No. 5-115776

Patent Literature 6: National Publication of International Patent Application No. 2003-521552
Patent Literature 7: Japanese Patent Laid-Open No. 8-127641
Patent Literature 8: Japanese Patent Laid-Open No. 2004-229750
Patent Literature 9: Japanese Patent Laid-Open No. 2-500846

SUMMARY OF INVENTION

Technical Problem

However, the oxygen absorbent of Patent Literature 2 has problems in that the oxygen-absorbing performance is primarily low; an effect is exerted only on an article to be packaged rich in moisture content; and the cost is relatively high.

The resin composition of Patent Literature 3 has the following problem. Since an oxygen-absorbing function is exerted by oxidizing a xylylene group-containing polyamide resin in the presence of a transition metal catalyst, the polymer chain of the resin is cut by oxidation degradation after absorption of oxygen, with the result that the strength of the packaging container itself decreases. In addition, the oxygen-absorbing performance of the resin composition described therein is still insufficient and the effect is exerted only on an article to be packaged rich in moisture content. In Patent Literature 4, a method of improving interlayer peeling is described; however, the effect is limited. In addition to this problem, the oxygen-absorbing performance of the resin composition described therein is still insufficient and the effect is exerted only on an article to be packaged rich in moisture content.

The oxygen-absorbing resin composition of Patent Literature 5 has the same problem as mentioned above, that is, the polymer chain of the resin is cut by oxidation to produce low molecular-weight organic compounds serving as odor-producing components, with the result that odor is produced after absorption of oxygen.

In the composition of Patent Literature 6, a special material containing a cyclohexene functional group must be used. This material still has a problem in relatively easily producing odor.

In the meantime, in the conventional gas barrier multilayer container and medical multilayer container mentioned above, the basic performance including oxygen barrier property, water vapor barrier property, drug solution adsorptivity, durability, etc. is not sufficient. Because of this, in view of storage stability of a content such as a drug solution and a food, improvement is required.

In particular, when foods, drug solutions, etc. are stored in conventional gas barrier multilayer containers, as a matter of fact, it is difficult or economically extremely unfavorable to completely remove oxygen in a packaging container no matter how gas displacement operation is performed. In other words, it is difficult to completely eliminate oxygen such as oxygen dissolved in a liquid content, oxygen contained in air bubbles generated and introduced in mixing contents, and oxygen dissolved in water when water is added. It is possible to remove oxygen as much as possible by highly strictly controlling conditions for selecting and preparing raw materials and manufacturing conditions; however, such an operation ignores an economic aspect and thus unrealistic. In addition, since the oxygen barrier property of the gas barrier multilayer containers as mentioned above is not sufficient, a small amount of oxygen entering through the wall of containers from the outside cannot be completely eliminated.

A medical container formed of a polyester resin, for example, disclosed in Patent Literature 7, has relatively excellent oxygen barrier property; however, the oxygen barrier property is insufficient to completely block oxygen. Such a medical container is inferior also in water vapor barrier property, compared to a container formed of a polyolefin resin. In addition, the polyester resin has no oxygen-absorbing performance. Because of this, when oxygen enters a container from the outside or when oxygen remains in the head space above the content (drug solution) in a container, degradation of the drug solution within the container cannot be prevented. The medical container has such a problem.

Furthermore, the prefilled syringe of Patent Literature 8 has relatively excellent oxygen barrier property and water vapor barrier property; however, the oxygen barrier property is insufficient to completely block oxygen. In addition, the oxygen barrier resin composition used in an intermediate layer does not have oxygen-absorbing performance. Therefore, when oxygen enters the container from the outside or when oxygen remains in the head space above the content in the container, degradation of the drug solution within the container cannot be prevented. The prefilled syringe has such a problem.

The resin composition of Patent Literature 9 has the same problem as in Patent Literatures 3 and 4. The strength of a resin decreases due to oxidation degradation after oxidation absorption and the strength of a packaging container itself decreases. In addition, the resin composition has problems in that oxygen-absorbing performance is still insufficient and an effect is exerted only on an article to be packaged rich in moisture content.

In the food field, when a content is oxidized by oxygen, a characteristic problem in food emerges. To describe more specifically, when foods are exposed to oxygen, components such as flavor components, sugars and vitamins are oxidized and decomposed. As a result, the color tone tends to significantly change and taste and flavor tends to significantly degrades. For example, in alcohol beverages, e.g., taste and flavor degrades. In fruit juices and vegetable juices, e.g., taste and flavor degrades and color tone changes. In broths, e.g., taste and flavor degrades, storage stability reduces and color changes to brown. In tea beverages, e.g., taste and flavor degrades and color tone changes. These problems are particularly concerned. In the food field, the taste and flavor and color tone of foods are recognized by consumers as indicators showing not only quality but also safety and determine their commodity values. Thus, quality control of taste and flavor and color tone is particularly important.

The present invention was made in consideration of the problems mentioned above. An object of the invention is to provide a novel oxygen-absorbing resin composition not responding to a metal detector, producing no odor after absorption of oxygen and having excellent oxygen-absorbing performance, and provide an oxygen-absorbing molded article using the composition. Another object of the present invention is to provide an oxygen-absorbing resin composition having excellent oxygen-absorbing performance in a wide range of humidity conditions from low humidity to high humidity and provide an oxygen-absorbing molded article using the composition.

Another object of the present invention is to provide a novel oxygen-absorbing multilayer body not responding to a metal detector, producing no odor after absorption of oxygen and having excellent oxygen-absorbing performance, and provide an oxygen-absorbing multilayer container using the multilayer body. Another object of the present invention is to provide an oxygen-absorbing multilayer body having excellent oxygen-absorbing performance in a wide range of humidity conditions from low humidity to high humidity and provide an oxygen-absorbing multilayer container using the multilayer body.

Another object of the present invention is to provide an oxygen-absorbing multilayer body excellent in oxygen-absorbing performance in a wide range of humidity conditions from low humidity to high humidity, resin strength and resin processability, and producing no odor, and provide an oxygen-absorbing multilayer container obtained by thermoforming the multilayer body.

Another object of the present invention is to provide a novel oxygen-absorbing paper container not responding to a metal detector, producing no odor after absorption of oxygen and having excellent oxygen-absorbing performance. Another object of the present invention is to provide an oxygen-absorbing paper container having excellent oxygen-absorbing performance in a wide range of humidity conditions from low humidity to high humidity.

Another object of the present invention is to provide a novel oxygen-absorbing injection-molded article and oxygen-absorbing multilayer injection-molded article not responding to a metal detector, producing no odor after absorption of oxygen and having excellent oxygen-absorbing performance, and provide oxygen-absorbing containers using these. Another object of the present invention is to provide a single-layer or multilayer oxygen-absorbing injection-molded article having excellent oxygen-absorbing performance in a wide range of humidity conditions from low humidity to high humidity, and provide an oxygen-absorbing container using the molded article.

Another object of the present invention is to provide a novel oxygen-absorbing medical multilayer molded container producing no odor after absorption of oxygen and having excellent oxygen barrier performance, preferably having excellent water vapor barrier performance, maintaining strength even in long-term storage and eluting a small amount of impurities. Another object of the present invention is to provide an oxygen-absorbing medical multilayer molded container having excellent oxygen-absorbing performance in a wide range of humidity conditions from low humidity to high humidity.

Another object of the present invention is to provide a novel oxygen-absorbing prefilled syringe suppressed in production of low molecular weight compounds after absorption of oxygen, having excellent oxygen barrier performance, maintaining strength even in long-term storage and eluting a small amount of impurities.

Another, new object of the present invention is to provide a method for stably storing an alcohol beverage for a long time, while keeping the taste and flavor and color tone of the alcohol beverage satisfactory by preventing oxidative degradation. Another, new object of the present invention is to provide a method for stably storing a fruit juice and/or a vegetable juice for a long time while keeping the taste and flavor and color tone of the fruit juice and/or the vegetable juice satisfactory by preventing oxidative degradation. Another object of the present invention is to provide a method for stably storing a broth for a long time while keeping the taste and flavor and color tone of the broth satisfactory by preventing oxidative degradation. Another object of the present invention is to provide a method for stably storing a liquid-state tea or a paste-state tea for a long time while keeping the taste and flavor and color tone of the liquid-state tea or paste-state tea satisfactory by preventing oxidative degradation.

Solution to Problem

The present inventors conducted intensive studies on an oxygen-absorbing resin composition. As a result, they found that the aforementioned problems are solved by using a polyester compound having a predetermined tetralin ring and a transition metal catalyst, and accomplished the present invention.

More specifically, the present invention provides the following <1-1> to <1-29>.

<1-1> An oxygen-absorbing resin composition containing a polyester compound and a transition metal catalyst, wherein the polyester compound has at least one constituent unit having a tetralin ring selected from the group consisting of constituent units represented by the following general formulas (1) to (4):

[Formula 1]

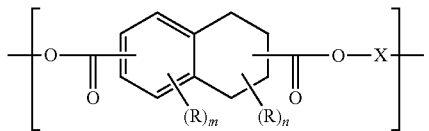
(1)

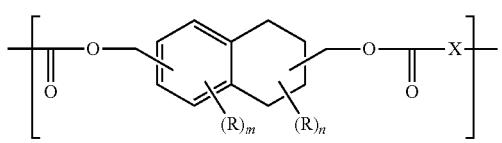
(2)

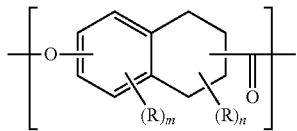
(3)

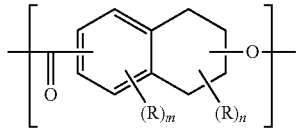
(4)

where R each independently represent a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; where m each independently represent an integer of 0 to 3; where n each independently represent an integer of 0 to 6, and at least one hydrogen atom is bound to a benzyl position of the tetralin ring; where X each independently represent a divalent group containing at least one group selected from the group consisting of an aromatic hydrocarbon group, a saturated or unsaturated alicyclic hydrocarbon group and a linear or branched and saturated or unsaturated aliphatic hydrocarbon group and a heterocyclic group.

<1-2> The oxygen-absorbing resin composition according to the above <1-1>, wherein the transition metal catalyst contains at least one transition metal selected from the group consisting of manganese, iron, cobalt, nickel and copper.

<1-3> The oxygen-absorbing resin composition according to the above <1-1> or <1-2>, wherein the transition metal catalyst is contained in an amount of 0.001 to 10 parts by mass in terms of a transition metal based on 100 parts by mass of the polyester compound.

<1-4> The oxygen-absorbing resin composition according to any one of the above <1-1> to <1-3>, wherein the constituent unit represented by the general formula (1) is at least one selected from the group consisting of the constituent units represented by following formulas (5) to (7):

[Formula 2]

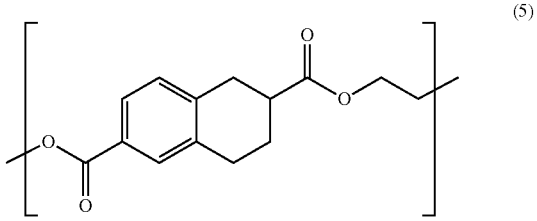
(5)

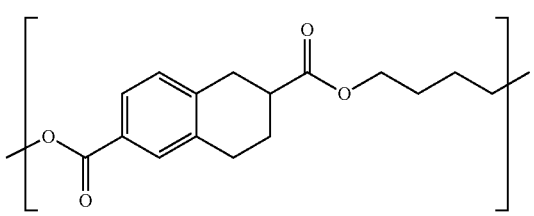
(6)

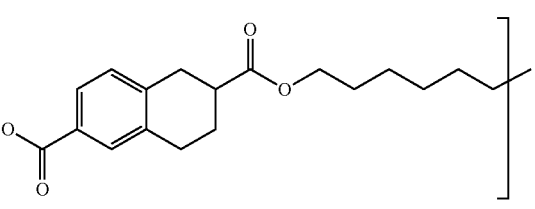
(7)

<1-5> The oxygen-absorbing resin composition according to any one of the above <1-1> to <1-4>, further containing a thermoplastic resin.

<1-6> The oxygen-absorbing resin composition according to any one of the above <1-1> to <1-5>, further containing a polyolefin resin.

<1-7> The oxygen-absorbing resin composition according to the above <1-6>, wherein the polyester compound is contained in an amount of 10 to 80 parts by mass based on 100 parts by mass of a total amount of the polyester compound and the polyolefin resin.

<1-8> An oxygen-absorbing molded article obtained by molding the oxygen-absorbing resin composition according to any one of the above <1-1> to <1-7> into a film or sheet form.

<1-9> An oxygen-absorbing multilayer body at least comprising an oxygen-absorbing layer formed of the oxygen-absorbing resin composition according to any one of the above <1-1> to <1-7> and a resin layer containing a thermoplastic resin.

<1-10> An oxygen-absorbing multilayer container comprising the oxygen-absorbing multilayer body according to the above <1-9>.

<1-11> An oxygen-absorbing multilayer body having at least three layers including a sealant layer containing a thermoplastic resin, an oxygen-absorbing layer formed of the oxygen-absorbing resin composition according to any one of the above <1-1> to <1-7> and a gas barrier layer containing a gas barrier substance, in this order.

<1-12> An oxygen-absorbing multilayer container comprising the oxygen-absorbing multilayer body according to the above <1-11>.

<1-13> An oxygen-absorbing paper container obtained by forming a carton from an oxygen-absorbing multilayer body having at least four layers including an isolation layer containing a thermoplastic resin, an oxygen-absorbing layer formed of the oxygen-absorbing resin composition according to any one of the above <1-1> to <1-7>, a gas barrier layer containing a gas barrier substance and a paper substrate layer in this order.

<1-14> An oxygen-absorbing injection-molded article formed of the oxygen-absorbing resin composition according to any one of the above <1-1> to <1-7>.

<1-15> An oxygen-absorbing container obtained by molding the oxygen-absorbing injection-molded article according to the above <1-14> into a cup or bottle form.

<1-16> The oxygen-absorbing container according to the above <1-15>, wherein the molding is stretch blow molding.

<1-17> An oxygen-absorbing multilayer injection-molded article comprising an oxygen-absorbing layer formed of the oxygen-absorbing resin composition according to any one of the above <1-1> to <1-7> and a resin layer containing a thermoplastic resin.

<1-18> An oxygen-absorbing multilayer container obtained by molding the oxygen-absorbing multilayer injection-molded article according to the above <1-17> into a cup or bottle form.

<1-19> The oxygen-absorbing multilayer container according to the above <1-18>, wherein the molding is stretch blow molding.

<1-20> An oxygen-absorbing medical multilayer molded container having at least three layers including a first resin layer at least containing a thermoplastic resin, an oxygen-absorbing layer formed of the oxygen-absorbing resin composition according to any one of the above <1-1> to <1-7> and a second resin layer at least containing a thermoplastic resin in this order.

<1-21> The oxygen-absorbing medical multilayer molded container according to the above <1-20>, wherein each of the thermoplastic resin of the first resin layer and the thermoplastic resin of the second resin layer is a polyolefin.

<1-22> The oxygen-absorbing medical multilayer molded container according to the above <1-20>, wherein each of the thermoplastic resin of the first resin layer and the thermoplastic resin of the second resin layer is a polyester other than the polyester compound containing the constituent unit having the tetralin ring.

<1-23> The oxygen-absorbing medical multilayer molded container according to the above <1-22>, wherein the polyester of the first resin layer and the polyester of the second resin layer each are obtained by polycondensation of at least two components of a polyvalent carboxylic acid containing no tetralin ring and a polyhydric alcohol containing no tetralin ring.

<1-24> An oxygen-absorbing prefilled syringe made capable of storing a medicinal agent in advance in a sealed condition, and releasing the sealed condition to eject the medical agent at the time of use, wherein the prefilled syringe is formed of a multilayered structure having at least three layers including a first resin layer containing a thermoplastic resin, an oxygen-absorbing layer formed of the oxygen-absorbing resin composition according to any one of the above <1-1> to <1-7> and a second resin layer containing a thermoplastic resin in this order.

<1-25> A method for storing a biopharmaceutical, comprising storing the biopharmaceutical in the oxygen-absorbing medical multilayer molded container according to any one of the above <1-20> to <1-23> or in the oxygen-absorbing prefilled syringe according to the above <1-24>.

<1-26> A method for storing an alcohol beverage, comprising storing the alcohol beverage in an oxygen-absorbing multilayer container using an oxygen-absorbing multilayer body in all or a part of the container, wherein the oxygen-absorbing multilayer body at least comprises an oxygen-absorbing layer formed of the oxygen-absorbing resin composition according to any one of the above <1-1> to <1-7> and a resin layer containing a thermoplastic resin.

<1-27> A method for storing a fruit juice and/or a vegetable juice, comprising storing the fruit juice and/or vegetable juice in an oxygen-absorbing multilayer container using an oxygen-absorbing multilayer body in all or a part of the container, wherein the oxygen-absorbing multilayer body at least comprises an oxygen-absorbing layer formed of the oxygen-absorbing resin composition according to any one of the above <1-1> to <1-7> and a resin layer containing a thermoplastic resin.

<1-28> A method for storing a broth, comprising storing the broth in an oxygen-absorbing container using an oxygen-absorbing multilayer body in all or a part of the container, wherein the oxygen-absorbing multilayer body at least comprises an oxygen-absorbing layer formed of the oxygen-absorbing resin composition according to any one of the above <1-1> to <1-7> and a resin layer containing a thermoplastic resin.

<1-29> A method for storing a liquid-state tea or a paste-state tea, comprising storing the liquid-state tea or paste-state tea in an oxygen-absorbing container using an oxygen-absorbing multilayer body in all or a part of the container, wherein the oxygen-absorbing multilayer body at least comprises an oxygen-absorbing layer formed of the oxygen-absorbing resin composition according to any one of the above <1-1> to <1-7> and a resin layer containing a thermoplastic resin.

Furthermore, the present inventors conducted intensive studies on an oxygen-absorbing resin composition. As a result, they found that the aforementioned problems are solved by using a polyester compound having a predetermined tetralin ring in combination with a transition metal catalyst and a polyolefin resin, and accomplished the present invention.

More specifically, the present invention provides the following <2-1> to <2-5>.

<2-1> An oxygen-absorbing resin composition containing a polyester compound, a transition metal catalyst and a polyolefin resin, wherein
the polyester compound has at least one constituent unit having a tetralin ring selected from the group consisting of constituent units represented by the above general formulas (1) to (4).

<2-2> The oxygen-absorbing resin composition according to the above <2-1>, wherein the transition metal catalyst contains at least one transition metal selected from the group consisting of manganese, iron, cobalt, nickel and copper.

<2-3> The oxygen-absorbing resin composition according to the above <2-1> or <2-2>, wherein the transition metal catalyst is contained in an amount of 0.001 to 10 parts by mass in terms of a transition metal based on 100 parts by mass of the polyester compound.

<2-4> The oxygen-absorbing resin composition according to any one of the above <2-1> to <2-3>, wherein the constituent unit represented by the general formula (1) is at least one selected from the group consisting of the constituent units represented by the above formulas (5) to (7).

<2-5> The oxygen-absorbing resin composition according to any one of the above <2-1> to <2-4>, wherein the polyester compound is contained in an amount of 10 to 80 parts by mass based on 100 parts by mass of the total amount of the polyester compound and the polyolefin resin.

The present inventors further conducted intensive studies on an oxygen-absorbing multilayer body. As a result, they found that the aforementioned problems are solved by using a polyester compound having a predetermined tetralin ring and a transition metal catalyst, and accomplished the present invention.

More specifically, the present invention provides the following <3-1> to <3-5>.

<3-1> An oxygen-absorbing multilayer body having at least an oxygen-absorbing layer (layer A) formed of an oxygen-absorbing resin composition containing a polyester compound and a transition metal catalyst and a resin layer (layer B) containing a thermoplastic resin, wherein
the polyester compound has at least one constituent unit having a tetralin ring selected from the group consisting of constituent units represented by the above general formulas (1) to (4).

<3-2> The oxygen-absorbing multilayer body according to the above <3-1>, wherein the transition metal catalyst contains at least one transition metal selected from the group consisting of manganese, iron, cobalt, nickel and copper.

<3-3> The oxygen-absorbing multilayer body according to the above <3-1> or <3-2>, wherein the transition metal catalyst is contained in an amount of 0.001 to 10 parts by mass in terms of a transition metal based on 100 parts by mass of the polyester compound.

<3-4> The oxygen-absorbing multilayer body according to any one of the above <3-1> to <3-3>, wherein the constituent unit represented by the general formula (1) is at least one selected from the group consisting of the constituent units represented by the above formulas (5) to (7).

<3-5> An oxygen-absorbing multilayer container having the oxygen-absorbing multilayer body according to any one of the above <3-1> to <3-4>.

The present inventors further conducted intensive studies on an oxygen-absorbing multilayer body. As a result, they found that the aforementioned problems are solved by using a polyester compound having a predetermined tetralin ring and a transition metal catalyst, and accomplished the present invention.

More specifically, the present invention provides the following <4-1> to <4-5>.

<4-1> An oxygen-absorbing multilayer body constituted of at least three layers, comprising a sealant layer (layer C) containing a thermoplastic resin, an oxygen-absorbing layer (layer A) formed of an oxygen-absorbing resin composition containing a polyester compound and a transition metal catalyst, and a gas barrier layer (layer D) containing a gas barrier substance, these of which are laminated in this order, wherein
the polyester compound has at least one constituent unit having a tetralin ring selected from the group consisting of constituent units represented by the above general formulas (1) to (4).

<4-2> The oxygen-absorbing multilayer body according to the above <4-1>, wherein the transition metal catalyst contains at least one transition metal selected from the group consisting of manganese, iron, cobalt, nickel and copper.

<4-3> The oxygen-absorbing multilayer body according to the above <4-1> or <4-2>, wherein the transition metal catalyst is contained in an amount of 0.001 to 10 parts by mass in terms of a transition metal based on 100 parts by mass of the polyester compound.

<4-4> The oxygen-absorbing multilayer body according to any one of the above <4-1> to <4-3>, wherein the constituent unit represented by the general formula (1) is at least one selected from the group consisting of the constituent units represented by the above formulas (5) to (7).

<4-5> An oxygen-absorbing multilayer container having the oxygen-absorbing multilayer body according to any one of the above <4-1> to <4-4>.

The present inventors conducted intensive studies on an oxygen-absorbing multilayer body. As a result, they found that the aforementioned problems are solved by using a polyester compound having a predetermined tetralin ring and a transition metal catalyst, and accomplished the present invention.

More specifically, the present invention provides the following <5-1> to <5-6>.

<5-1> An oxygen-absorbing multilayer body having at least three layers, comprising a sealant layer (layer C) containing a thermoplastic resin, an oxygen-absorbing layer (layer A) formed of an oxygen-absorbing resin composition containing a polyester compound, a transition metal catalyst and a polyolefin resin, and a gas barrier layer (layer D) containing a gas barrier substance, these of which are laminated in this order, wherein
the polyester compound has at least one constituent unit having a tetralin ring selected from the group consisting of constituent units represented by the above general formulas (1) to (4).

<5-2> The oxygen-absorbing multilayer body according to the above <5-1>, wherein the transition metal catalyst contains at least one transition metal selected from the group consisting of manganese, iron, cobalt, nickel and copper.

<5-3> The oxygen-absorbing multilayer body according to the above <5-1> or <5-2>, wherein the transition metal catalyst is contained in an amount of 0.001 to 10 parts by mass in terms of a transition metal based on 100 parts by mass of the polyester compound.

<5-4> The oxygen-absorbing multilayer body according to any one of the above <5-1> to <5-3>, wherein the constituent unit represented by the general formula (1) is at least one selected from the group consisting of the constituent units represented by the above formulas (5) to (7).

<5-5> The oxygen-absorbing multilayer body according to any one of the above <5-1> to <5-4>, wherein the polyester compound is contained in an amount of 10 to 80 parts by mass based on 100 parts by mass of the total amount of the polyester compound and the polyolefin resin.

<5-6> An oxygen-absorbing multilayer container having the oxygen-absorbing multilayer body according to any one of the above <5-1> to <5-5>.

The present inventors further conducted intensive studies on an oxygen-absorbing paper container. As a result, they found that the aforementioned problems are solved by using a polyester compound having a predetermined tetralin ring and a transition metal catalyst, and accomplished the present invention.

More specifically, the present invention provides the following <6-1> to <6-4>.

<6-1> An oxygen-absorbing paper container obtained by forming a carton from an oxygen-absorbing multilayer body having at least four layers, comprising an isolation layer (layer F) containing a thermoplastic resin, an oxygen-absorbing layer (layer A) formed of an oxygen-absorbing resin composition containing a polyester compound and a transition metal catalyst, a gas barrier layer (layer D) containing a gas barrier substance and a paper substrate layer (layer E), these of which are laminated in this order, wherein the polyester compound has at least one constituent unit having a tetralin ring selected from the group consisting of constituent units represented by the above general formulas (1) to (4).

<6-2> The oxygen-absorbing paper container according to the above <6-1>, wherein the transition metal catalyst contains at least one transition metal selected from the group consisting of manganese, iron, cobalt, nickel and copper.

<6-3> The oxygen-absorbing paper container according to the above <6-1> or <6-2>, wherein the transition metal catalyst is contained in an amount of 0.001 to 10 parts by mass in terms of a transition metal based on 100 parts by mass of the polyester compound.

<6-4> The oxygen-absorbing paper container according to any one of the above <6-1> to <6-3>, wherein the constituent unit represented by the general formula (1) is at least one selected from the group consisting of the constituent units represented by the above formulas (5) to (7).

The present inventors further conducted intensive studies on an oxygen-absorbing injection-molded article. As a result, they found that the aforementioned problems are solved by using a polyester compound having a predetermined tetralin ring, a transition metal catalyst and a thermoplastic resin, and accomplished the present invention.

More specifically, the present invention provides the following <7-1> to <7-7>.

<7-1> An oxygen-absorbing injection-molded article formed of an oxygen-absorbing resin composition containing a polyester compound, a transition metal catalyst and a thermoplastic resin, wherein the polyester compound has at least one constituent unit having a tetralin ring selected from the group consisting of constituent units represented by the above general formulas (1) to (4).

<7-2> The oxygen-absorbing injection-molded article according to the above <7-1>, wherein the transition metal catalyst contains at least one transition metal selected from the group consisting of manganese, iron, cobalt, nickel and copper.

<7-3> The oxygen-absorbing injection-molded article according to the above <7-1> or <7-2>, wherein the transition metal catalyst is contained in an amount of 0.001 to 10 parts by mass in terms of a transition metal based on 100 parts by mass of the oxygen-absorbing layer.

<7-4> The oxygen-absorbing injection-molded article according to any one of the above <7-1> to <7-3>, wherein the constituent unit represented by the general formula (1) is at least one selected from the group consisting of the constituent units represented by the above formulas (5) to (7).

<7-5> The oxygen-absorbing injection-molded article according to any one of the above <7-1> to <7-4>, wherein the polyester compound is contained in an amount of 5 to 95 parts by mass based on 100 parts by mass of the total amount of the polyester compound and the thermoplastic resin.

<7-6> An oxygen-absorbing container obtained by further processing the oxygen-absorbing injection-molded article according to any one of the above <7-1> to <7-5>.

<7-7> The oxygen-absorbing container according to the above <7-6> obtained by stretch blow molding.

The present inventors conducted intensive studies on an oxygen-absorbing multilayer injection-molded article. As a result, they found that the aforementioned problems are solved by using a polyester compound having a predetermined tetralin ring and a transition metal catalyst, and accomplished the present invention.

More specifically, the present invention provides the following <8-1> to <8-6>.

<8-1> An oxygen-absorbing multilayer injection-molded article having an oxygen-absorbing layer (layer A) formed of an oxygen-absorbing resin composition containing a polyester compound and a transition metal catalyst, and a resin layer (layer B) containing a thermoplastic resin, wherein the polyester compound has at least one constituent unit having a tetralin ring selected from the group consisting of constituent units represented by the above general formulas (1) to (4).

<8-2> The oxygen-absorbing multilayer injection-molded article according to the above <8-1>, wherein the transition metal catalyst contains at least one transition metal selected from the group consisting of manganese, iron, cobalt, nickel and copper.

<8-3> The oxygen-absorbing multilayer injection-molded article according to the above <8-1> or <8-2>, wherein the transition metal catalyst is contained in an amount of 0.001 to 10 parts by mass in terms of a transition metal based on 100 parts by mass of the polyester compound.

<8-4> The oxygen-absorbing multilayer injection-molded article according to any one of the above <8-1> to <8-3>, wherein the constituent unit represented by the general formula (1) is at least one selected from the group consisting of the constituent units represented by the above formulas (5) to (7).

<8-5> An oxygen-absorbing multilayer container obtained by further processing the oxygen-absorbing multilayer injection-molded article according to any one of the above <8-1> to <8-4>.

<8-6> The oxygen-absorbing multilayer container according to the above <8-5> obtained by stretch blow molding.

The present inventors further conducted intensive studies on an oxygen-absorbing multilayer injection-molded article. As a result, they found that the aforementioned problems are solved by using a polyester compound having a predetermined tetralin ring and a transition metal catalyst, and accomplished the present invention.

More specifically, the present invention provides the following <9-1> to <9-7>.

<9-1> An oxygen-absorbing multilayer injection-molded article having an oxygen-absorbing layer (layer A) formed of an oxygen-absorbing resin composition containing a polyester compound, a transition metal catalyst and a thermoplastic resin (a), and a resin layer (layer B) containing a thermoplastic resin (b), wherein the polyester compound has at least one constituent unit having a tetralin ring selected from the group consisting of constituent units represented by the above general formulas (1) to (4).

<9-2> The oxygen-absorbing multilayer injection-molded article according to the above <9-1>, wherein the transition metal catalyst contains at least one transition metal selected from the group consisting of manganese, iron, cobalt, nickel and copper.

<9-3> The oxygen-absorbing multilayer injection-molded article according to the above <9-1> or <9-2>, wherein the transition metal catalyst is contained in an amount of 0.001 to 10 parts by mass in terms of a transition metal based on 100 parts by mass of the polyester compound.

<9-4> The oxygen-absorbing multilayer injection-molded article according to any one of the above <9-1> to <9-3>, wherein the constituent unit represented by the general formula (1) is at least one selected from the group consisting of the constituent units represented by the above formulas (5) to (7).

<9-5> The oxygen-absorbing multilayer injection-molded article according to any one of the above <9-1> to <9-4>, wherein the polyester compound is contained in an amount of 5 to 95 parts by mass based on 100 parts by mass of the total amount of polyester compound and thermoplastic resin (a).

<9-6> An oxygen-absorbing multilayer container obtained by further processing the oxygen-absorbing multilayer injection-molded article according to any one of the above <9-1> to <9-5>.

<9-7> The oxygen-absorbing multilayer container according to the above <9-6> obtained by stretch blow molding.

The present inventors conducted intensive studies on an oxygen-absorbing medical multilayer molded container. As a result, they found that the aforementioned problems are solved by using a polyester compound having a predetermined tetralin ring and a transition metal catalyst, and accomplished the present invention.

More specifically, the present invention provides the following <10-1> to <10-4>.

<10-1> An oxygen-absorbing medical multilayer molded container having at least three layers, comprising an oxygen-absorbing layer (layer A) formed of an oxygen-absorbing resin composition containing a polyester compound and a transition metal catalyst, and a resin layer (layer B) containing a thermoplastic resin, the layer B being laminated on both sides of the layer A, wherein the polyester compound has at least one constituent unit having a tetralin ring selected from the group consisting of constituent units represented by the above general formulas (1) to (4).

<10-2> The oxygen-absorbing medical multilayer molded container according to the above <10-1>, wherein the transition metal catalyst contains at least one transition metal selected from the group consisting of manganese, iron, cobalt, nickel and copper.

<10-3> The oxygen-absorbing medical multilayer molded container according to the above <10-1> or <10-2>, wherein the transition metal catalyst is contained in an amount of 0.001 to 10 parts by mass in terms of a transition metal based on 100 parts by mass of the polyester compound.

<10-4> The oxygen-absorbing medical multilayer molded container according to any one of the above <10-1> to <10-3>, wherein the constituent unit represented by the general formula (1) is at least one selected from the group consisting of the constituent units represented by the above formulas (5) to (7).

The present inventors conducted intensive studies on an oxygen-absorbing medical multilayer molded container. As a result, they found that the aforementioned problems are solved by using a polyester compound having a predetermined tetralin ring and a transition metal catalyst, and accomplished the present invention.

More specifically, the present invention provides the following <11-1> to <11-4>.

<11-1> An oxygen-absorbing medical multilayer molded container having at least three layers, comprising an oxygen-absorbing layer (layer A) formed of an oxygen-absorbing resin composition containing a polyester compound and a transition metal catalyst, and a resin layer (layer B) containing a polyolefin, the layer B being laminated on both sides of the layer A, wherein the polyester compound has at least one constituent unit having a tetralin ring selected from the group consisting of constituent units represented by the above general formulas (1) to (4).

<11-2> The oxygen-absorbing medical multilayer molded container according to the above <11-1>, wherein the transition metal catalyst contains at least one transition metal selected from the group consisting of manganese, iron, cobalt, nickel and copper.

<11-3> The oxygen-absorbing medical multilayer molded container according to the above <11-1> or <11-2>, wherein the transition metal catalyst is contained in an amount of 0.001 to 10 parts by mass in terms of a transition metal based on 100 parts by mass of the polyester compound.

<11-4> The oxygen-absorbing medical multilayer molded container according to any one of the above <11-1> to <11-3>, wherein the constituent unit represented by the general formula (1) is at least one selected from the group consisting of the constituent units represented by the above formulas (5) to (7).

The present inventors further conducted intensive studies on an oxygen-absorbing medical multilayer molded container. As a result, they found that the aforementioned problems are solved by laminating an oxygen-absorbing layer using a polyester compound having a predetermined tetralin ring and a transition metal catalyst, and a resin layer using a polyester compound containing no tetralin ring, and accomplished the present invention.

More specifically, the present invention provides the following <12-1> to <12-9>.

<12-1> An oxygen-absorbing medical multilayer molded container having at least three layers, comprising an oxygen-absorbing layer (layer A) formed of an oxygen-absorbing resin composition containing a polyester compound (a) and a transition metal catalyst, and a resin layer (layer B) containing a polyester compound (b), the layer B being laminated on both sides of the layer A, wherein the polyester compound (a) contains at least one constituent unit having a tetralin ring selected from the group consisting of constituent units represented by the above general formulas (1) to (4) and the polyester compound (b) does not contain a constituent unit having a tetralin ring selected from the group consisting of constituent units represented by the above general formulas (1) to (4).

<12-2> The oxygen-absorbing medical multilayer molded container according to the above <12-1>, wherein the transition metal catalyst contains at least one transition metal selected from the group consisting of manganese, iron, cobalt, nickel and copper.

<12-3> The oxygen-absorbing medical multilayer molded container according to the above <12-1> or <12-2>, wherein the transition metal catalyst is contained in an amount of 0.001 to 10 parts by mass in terms of a transition metal based on 100 parts by mass of the polyester compound (a).

<12-4> The oxygen-absorbing medical multilayer molded container according to any one of the above <12-1> to <12-3>, wherein the constituent unit represented by the general formula (1) is at least one selected from the group consisting of the constituent units represented by the above formulas (5) to (7).

<12-5> The oxygen-absorbing medical multilayer molded container according to any one of the above <12-1> to <12-4>, wherein the polyester compound (b) contains a dicarboxylic acid unit, 70 mole % or more of which is derived from at least one dicarboxylic acid selected from the group consisting of terephthalic acid, isophthalic acid, 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid.

<12-6> The oxygen-absorbing medical multilayer molded container according to any one of the above <12-1> to <12-4>, wherein the polyester compound (b) contains a dicarboxylic acid unit, 70 mole % or more of which is derived from terephthalic acid.

<12-7> The oxygen-absorbing medical multilayer molded container according to any one of the above <12-1> to <12-4>, wherein the polyester compound (b) contains a dicarboxylic acid unit, 90 mole % or more of which is derived from terephthalic acid.

<12-8> The oxygen-absorbing medical multilayer molded container according to any one of the above <12-1> to <12-4>, wherein the polyester compound (b) contains a dicarboxylic acid unit, 70 mole % or more of which is derived from 2,6-naphthalenedicarboxylic acid.

<12-9> The oxygen-absorbing medical multilayer molded container according to any one of the above <12-1> to <12-4>, wherein the polyester compound (b) contains a dicarboxylic acid unit, 90 mole % or more of which has a 2,6-naphthalenedicarboxylic acid skeleton.

The present inventors conducted intensive studies on an oxygen-absorbing prefilled syringe. As a result, they found that the aforementioned problems are solved by using a polyester compound having a predetermined tetralin ring and a transition metal catalyst, and accomplished the present invention.

More specifically, the present invention provides the following <13-1> to <13-4>.

<13-1> An oxygen-absorbing prefilled syringe made capable of storing a medicinal agent in advance in a sealed condition, and releasing the sealed condition to eject the medical agent at the time of use, wherein the prefilled syringe is formed of a multilayered structure having at least three layers, which is comprising an oxygen-absorbing layer (layer A) formed of an oxygen-absorbing resin composition containing a polyester compound and a transition metal catalyst, and a resin layer (layer B) containing a thermoplastic resin, the layer B being laminated on both sides of the layer A and the polyester compound has at least one constituent unit having a tetralin ring selected from the group consisting of constituent units represented by the above general formulas (1) to (4).

<13-2> The oxygen-absorbing prefilled syringe according to the above <13-1>, wherein the transition metal catalyst contains at least one transition metal selected from the group consisting of manganese, iron, cobalt, nickel and copper.

<13-3> The oxygen-absorbing prefilled syringe according to the above <13-1> or <13-2>, wherein the transition metal catalyst is contained in an amount of 0.001 to 10 parts by mass in terms of a transition metal based on 100 parts by mass of the polyester compound.

<13-4> The oxygen-absorbing prefilled syringe according to any one of the above <13-1> to <13-3>, wherein the constituent unit represented by the general formula (1) is at least one selected from the group consisting of the constituent units represented by the above formulas (5) to (7).

The present inventors conducted intensive studies on a method for storing a biopharmaceutical. As a result, they found that the aforementioned problems are solved by storing the biopharmaceutical in an oxygen-absorbing medical multilayer molded container using a polyester compound having a predetermined tetralin ring and a transition metal catalyst, and accomplished the present invention.

More specifically, the present invention provides the following <14-1> to <14-4>.

<14-1> A method for storing a biopharmaceutical including storing the biopharmaceutical in an oxygen-absorbing medical multilayer molded container having at least three layers, comprising an oxygen-absorbing layer (layer A) formed of an oxygen-absorbing resin composition containing a polyester compound and a transition metal catalyst, and a resin layer (layer B) containing a thermoplastic resin, the layer B being laminated on both sides of the layer A, wherein the polyester compound has at least one constituent unit having a tetralin ring selected from the group consisting of constituent units represented by the above general formulas (1) to (4).

<14-2> The method for storing a biopharmaceutical according to the above <14-1>, wherein the transition metal catalyst contains at least one transition metal selected from the group consisting of manganese, iron, cobalt, nickel and copper.

<14-3> The method for storing a biopharmaceutical according to the above <14-1> or <14-2>, wherein the transition metal catalyst is contained in an amount of 0.001 to 10 parts by mass in terms of a transition metal based on 100 parts by mass of the polyester compound.

<14-4> The method for storing a biopharmaceutical according to any one of the above <14-1> to <14-3>, wherein the constituent unit represented by the general formula (1) is at least one selected from the group consisting of the constituent units represented by the above formulas (5) to (7).

The present inventors conducted intensive studies on a method for storing an alcohol beverage. As a result, they found that the aforementioned problems are solved by storing the alcohol beverage in a container using an oxygen-absorbing resin composition containing a polyester compound having a predetermined tetralin ring and a transition metal catalyst as one of the layers constituting the container, and accomplished the present invention.

More specifically, the present invention provides the following <15-1> to <15-4>.

<15-1> A method for storing an alcohol beverage including storing the alcohol beverage in an oxygen-absorbing container using an oxygen-absorbing multilayer body containing an oxygen-absorbing layer (layer A) formed of an oxygen-absorbing resin composition containing a polyester compound and a transition metal catalyst, and a resin layer (layer B) containing a thermoplastic resin, in whole or in part, wherein the polyester compound has at least one constituent unit having a tetralin ring selected from the group consisting of constituent units represented by the above general formulas (1) to (4).

<15-2> The method for storing an alcohol beverage according to the above <15-1>, wherein the transition metal catalyst contains at least one transition metal selected from the group consisting of manganese, iron, cobalt, nickel and copper.

<15-3> The method for storing an alcohol beverage according to the above <15-1> or <15-2>, wherein the transition metal catalyst is contained in an amount of 0.001 to 10 parts by mass in terms of a transition metal based on 100 parts by mass of the polyester compound.

<15-4> The method for storing an alcohol beverage according to any one of the above <15-1> to <15-3>, wherein the constituent unit represented by the general formula (1) is at least one selected from the group consisting of the constituent units represented by the above formulas (5) to (7).

The present inventors conducted intensive studies on a method for storing a fruit juice and/or a vegetable juice. As a result, they found that the aforementioned problems are solved by storing the fruit juice and/or a vegetable juice in a container using an oxygen-absorbing resin composition containing a polyester compound having a predetermined tetralin ring and a transition metal catalyst as one of the layers constituting the container, and accomplished the present invention.

More specifically, the present invention provides the following <16-1> to <16-4>.

<16-1> A method for storing a fruit juice and/or a vegetable juice including storing the fruit juice and/or the vegetable juice in an oxygen-absorbing container using an oxygen-absorbing multilayer body containing an oxygen-absorbing layer (layer A) formed of an oxygen-absorbing resin composition containing a polyester compound and a transition metal catalyst, and a resin layer (layer B) containing a thermoplastic resin, in whole or in part, wherein
the polyester compound has at least one constituent unit having a tetralin ring selected from the group consisting of constituent units represented by the above general formulas (1) to (4).

<16-2> The method for storing a fruit juice and/or a vegetable juice according to the above <16-1>, wherein the transition metal catalyst contains at least one transition metal selected from the group consisting of manganese, iron, cobalt, nickel and copper.

<16-3> The method for storing a fruit juice and/or a vegetable juice according to the above <16-1> or <16-2>, wherein the transition metal catalyst is contained in an amount of 0.001 to 10 parts by mass in terms of a transition metal based on 100 parts by mass of the polyester compound.

<16-4> The method for storing a fruit juice and/or a vegetable juice according to any one of the above <16-1> to <16-3>, wherein the constituent unit represented by the general formula (1) is at least one selected from the group consisting of the constituent units represented by the above formulas (5) to (7).

The present inventors conducted intensive studies on a method for storing a broth. As a result, they found that the aforementioned problems are solved by storing the broth in a container using an oxygen-absorbing resin composition containing a polyester compound having a predetermined tetralin ring and a transition metal catalyst as one of the layers constituting the container, and accomplished the present invention.

More specifically, the present invention provides the following <17-1> to <17-4>.

<17-1> A method for storing a broth including storing the broth in an oxygen-absorbing container using an oxygen-absorbing multilayer body containing an oxygen-absorbing layer (layer A) formed of an oxygen-absorbing resin composition containing a polyester compound and a transition metal catalyst, and a resin layer (layer B) containing a thermoplastic resin, in whole or in part, wherein
the polyester compound has at least one constituent unit having a tetralin ring selected from the group consisting of constituent units represented by the above general formulas (1) to (4).

<17-2> The method for storing a broth according to the above <17-1>, wherein the transition metal catalyst contains at least one transition metal selected from the group consisting of manganese, iron, cobalt, nickel and copper.

<17-3> The method for storing a broth according to the above <17-1> or <17-2>, wherein the transition metal catalyst is contained in an amount of 0.001 to 10 parts by mass in terms of a transition metal based on 100 parts by mass of the polyester compound.

<17-4> The method for storing a broth according to any one of the above <17-1> to <17-3>, wherein the constituent unit represented by the general formula (1) is at least one selected from the group consisting of the constituent units represented by the above formulas (5) to (7).

The present inventors conducted intensive studies on a method for storing a liquid-state tea or a paste-state tea. As a result, they found that the aforementioned problems are solved by storing the liquid-state tea or the paste-state tea in a container using an oxygen-absorbing resin composition containing a polyester compound having a predetermined tetralin ring and a transition metal catalyst as one of the layers constituting the container, and accomplished the present invention.

More specifically, the present invention provides the following <18-1> to <18-4>.

<18-1> A method for storing a liquid-state tea or a paste-state tea including storing the liquid-state tea or the paste-state tea in an oxygen-absorbing container using an oxygen-absorbing multilayer body containing an oxygen-absorbing layer (layer A) formed of an oxygen-absorbing resin composition containing a polyester compound and a transition metal catalyst, and a resin layer (layer B) containing a thermoplastic resin, in whole or in part, wherein
the polyester compound has at least one constituent unit having a tetralin ring selected from the group consisting of constituent units represented by the above general formulas (1) to (4).

<18-2> The method for storing a liquid-state tea or a paste-state tea according to the above <18-1>, wherein the transition metal catalyst contains at least one transition metal selected from the group consisting of manganese, iron, cobalt, nickel and copper.

<18-3> The method for storing a liquid-state tea or a paste-state tea according to the above <18-1> or <18-2>, wherein the transition metal catalyst is contained in an amount of 0.001 to 10 parts by mass in terms of a transition metal based on 100 parts by mass of the polyester compound.

<18-4> The method for storing a liquid-state tea or a paste-state tea according to any one of the above <18-1> to <18-3>, wherein the constituent unit represented by the general formula (1) is at least one selected from the group consisting of the constituent units represented by the above formulas (5) to (7).

Advantageous Effects of Invention

According to one aspect of the present invention, it is possible to provide an oxygen-absorbing resin composition having excellent oxygen-absorbing performance in a wide range of humidity conditions from low humidity to high humidity and an oxygen-absorbing molded article using the composition, as well as an oxygen-absorbing multilayer body, an oxygen-absorbing multilayer container, etc. The oxygen-absorbing resin composition etc., since they can absorb oxygen regardless of the presence or absence of the moisture content of an article to be packaged and produce no odor after absorption of oxygen, can be applied to a wide variety of uses including foods, cooking foods, beverages, medicinal products and health foods, no matter what products they are. Furthermore, it is also possible to provide an oxygen-absorbing resin composition etc. not responsive to a metal detector. Moreover, the oxygen-absorbing resin composition, since it is excellent in processability and adhesion with a polyolefin resin, can also be provided as an oxygen-absorbing resin composition excellent in processability into films, sheets, molded containers, etc. In addition, according to a preferable aspect of the present invention, since a reduction in strength of the polyester compound having a tetralin ring by oxidation is extremely low even after absorption of oxygen and the strength of the oxygen-absorbing layer can be maintained even in long-term use, it is also possible to provide an oxygen-absorbing multilayer body rarely having interlayer peeling, an oxygen-absorbing multilayer container, etc. using the multilayer body.

According to another aspect of the present invention, it is possible to provide an oxygen-absorbing injection-molded article and an oxygen-absorbing multilayer injection-molded article having excellent oxygen-absorbing performance in a wide range of humidity conditions from low humidity to high humidity as well as oxygen-absorbing containers using these. These oxygen-absorbing injection-molded articles, oxygen-absorbing containers, etc., since they can absorb oxygen regardless of the presence or absence of a moisture content of an article to be packaged and produce no odor after absorption of oxygen, can be applied to a wide variety of uses including foods, cooking foods, beverages, medicinal products, health foods, etc., no matter what products they are. Furthermore, it is also possible to provide an oxygen-absorbing injection-molded article, an oxygen-absorbing container, etc. not responsive to a metal detector. In addition, according to a preferable aspect of the present invention, since a reduction in strength of the polyester compound by oxidation is extremely low even after absorption of oxygen and the strength of the oxygen-absorbing layer can be maintained even in long-term use, it is also possible to provide an oxygen-absorbing injection-molded article, an oxygen-absorbing container, etc. rarely having interlayer peeling.

According to another aspect of the present invention, it is possible to provide an oxygen-absorbing medical multilayer molded container, such as a vial and a prefilled syringe, having excellent oxygen-absorbing performance in a wide range of humidity conditions from low humidity to high humidity and satisfactory oxygen barrier property and, in a preferable aspect, further excellent water vapor barrier property. Such an oxygen-absorbing medical multilayer molded container, since it can absorb oxygen regardless of the presence or absence of the moisture content of an article to be packaged and produces no odor after absorption of oxygen, can be used in various medicinal products and medical supplies. Furthermore, since a reduction in strength of the polyester compound having a tetralin ring by oxidation is extremely low even after absorption of oxygen and the strength of the oxygen-absorbing layer is maintained even in long-term use, it is also possible to provide an oxygen-absorbing medical multilayer molded container rarely having interlayer peeling. Moreover, since generation of a low molecular weight organic compound is suppressed after absorption of oxygen, it is also possible to provide an oxygen-absorbing medical multilayer molded container less contaminating the content with low molecular weight organic compound. Because of this, the oxygen-absorbing medical multilayer molded container of the present invention is particularly useful in storing medicinal products, biopharmaceuticals, medical supplies, etc. requiring storage under a low oxygen concentration.

According to one aspect of the method of the present invention, it is possible to provide a method for storing an alcohol beverage for a long term without producing odor from a container after absorption of oxygen and without excessively degrading taste and flavor of the alcohol beverage. In addition, since replacement of metal cans and glass bottles can be made, the weight of the container and the amount of non-combustible waste can be reduced. Furthermore, since the strength of the packaging container is maintained even after long-term storage, handling property and reliability are improved. According to one aspect of the method of the present invention, it is possible to provide a method for storing a fruit juice and/or a vegetable juice for a long term without producing odor from a container after absorption of oxygen and without excessively degrading taste and flavor and color tone of the fruit juice and/or vegetable juice. In addition, since replacement of metal cans and glass bottles can be made, the weight of the container and the amount of non-combustible waste can be reduced. Furthermore, since the strength of the packaging container is maintained even after long-term storage, handling property and reliability are improved. According to one aspect of the method of the present invention, it is possible to provide a method for storing a broth for a long term without producing odor from a container after absorption of oxygen and without excessively degrading taste and flavor of the broth. In addition, since replacement of metal cans and glass bottles can be made, the weight of the container and the amount of non-combustible waste can be reduced. Furthermore, since the strength of the packaging container is maintained even after long-term storage, handling property and reliability are improved. According to one aspect of the method of the present invention, it is possible to provide a method for storing a liquid-state tea or a paste-state tea for a long term without producing odor from a container after absorption of oxygen and without excessively degrading taste and flavor of the liquid-state tea or the paste-state tea. In addition, since replacement of metal cans and glass bottles can be made, the weight of the container and the amount of non-combustible waste can be reduced. Furthermore, since the strength of the packaging container is maintained even after long-term storage, handling property and reliability are improved.

DESCRIPTION OF EMBODIMENTS

Now, embodiments of the present invention will be described below. Note that the following embodiments are examples for explaining the present invention and the present invention is not limited to the embodiments alone.

(First Embodiment)
[Oxygen-Absorbing Resin Composition]

The oxygen-absorbing resin composition of the embodiment at least contains a polyester compound (hereinafter, simply referred also to a "tetralin ring-containing polyester compound") containing at least one constituent unit having a tetralin ring selected from the group consisting of constituent units represented by the above general formulas (1) to (4) and a transition metal catalyst.

<Tetralin Ring-Containing Polyester Compound>

The tetralin ring-containing polyester compound to be used in the oxygen-absorbing resin composition of the embodiment contains at least one of the constituent units represented by the above general formulas (1) to (4). It is preferable that the constituent unit represented by the above general formula (1) is at least one selected from the group consisting of constituent units represented by the above formulas (5) to (7). The phrase of "contains . . . a constituent unit" herein means that one or more constituent units are contained in a compound. It is preferable that such a constituent unit is contained as a repeat unit in a tetralin ring-containing polyester compound. Likewise, if a tetralin ring-containing polyester compound is a polymer, the compound may be any one of a homopolymer of the above constituent unit, a random copolymer of the above constituent unit and another constituent unit, and a block copolymer of the above constituent unit and another constituent unit.

In the constituent units represented by the above general formulas (1) to (4), examples of the monovalent substituent represented by R include, but not particularly limited to, a halogen atom (for example, a chlorine atom, a bromine atom, an iodine atom), an alkyl group (a linear, branched or cyclic alkyl group having preferably 1 to 15 carbon atoms and more preferably 1 to 6 carbon atoms, such as a methyl group, an ethyl group, a n-propyl group, an isopropyl group, a t-butyl group, a n-octyl group, a 2-ethylhexyl group, a cyclopropyl group, and a cyclopentyl group), an alkenyl group (a linear, branched or cyclic alkenyl group having preferably 2 to 10 carbon atoms and more preferably 2 to 6 carbon atoms, such as a vinyl group and an allyl group), an alkynyl group (an alkynyl group having preferably 2 to 10 carbon atoms and more preferably 2 to 6 carbon atoms, such as an ethynyl group and a propargyl group), an aryl group (an aryl group having preferably 6 to 16 carbon atoms and more preferably 6 to 10 carbon atoms, such as a phenyl group and a naphthyl group), a heterocyclic group (a monovalent group obtained by removing a single hydrogen atom from a 5-member or 6-member aromatic or non-aromatic heterocyclic compound having preferably 1 to 12 carbon atoms and more preferable 2 to 6 carbon atoms, such as a 1-pyrazolyl group, a 1-imidazolyl group and a 2-furyl group), a cyano group, a hydroxy group, a carboxyl group, an ester group, an amido group, a nitro group, an alkoxy group (linear, branched or cyclic alkoxy group having preferably 1 to 10 carbon atoms and more preferably 1 to 6 carbon atoms, such as a methoxy group and an ethoxy group), an aryloxy group (an aryloxy group having preferably 6 to 12 carbon atoms and more preferably 6 to 8 carbon atoms, such as a phenoxy group), an acyl group (including a formyl group. An alkyl carbonyl group having preferably 2 to 10 carbon atoms and more preferably 2 to 6 carbon atoms, and an arylcarbonyl group having preferably 7 to 12 carbon atoms and more preferably 7 to 9 carbon atoms, such as an acetyl group, a pivaloyl group and a benzoyl group), an amino group (an alkylamino group having preferably 1 to 10 carbon atoms and more preferably 1 to 6 carbon atoms, an anilino group having preferably 6 to 12 carbon atoms and more preferably 6 to 8 carbon atoms, a heterocyclic amino group having preferably 1 to 12 carbon atoms and more preferably 2 to 6 carbon atoms, such as an amino group, a methylamino group and an anilino group), a mercapto group, an alkylthio group (an alkylthio group having preferably 1 to 10 carbon atoms and more preferably 1 to 6 carbon atoms, such as a methylthio group and an ethylthio group), an arylthio group (an arylthio group having preferably 6 to 12 carbon atoms and more preferably 6 to 8 carbon atoms, such as a phenylthio group), a heterocyclic thio group (a heterocyclic thio group having preferably 2 to 10 carbon atoms and more preferably 1 to 6 carbon atoms, such as a 2-benzothiazolylthio group), an imido group (an imido group having preferably 2 to 10 carbon atoms and more preferably 4 to 8 carbon atoms, such as a N-succinimido group and a N-phthalimido group).

Note that when the above monovalent substituent R has a hydrogen atom, the hydrogen atom may be further substituted with a substituent T (herein, substituent T is the same as defined in the above monovalent substituent R). Specific examples thereof include, but not particularly limited to, an alkyl group substituted with a hydroxy group (for example, a hydroxyethyl group), an alkyl group substituted with an alkoxy group (for example, a methoxyethyl group), an alkyl group substituted with an aryl group (for example, a benzyl group), an alkyl group substituted with a primary or secondary amino group (for example, an aminoethyl group), an aryl group substituted with an alkyl group (for example, a p-tolyl group) and an aryloxy group substituted with an alkyl group (for example, a 2-methylphenoxy group). Note that when the monovalent substituent R has a monovalent substituent T, the number of carbon atoms of the substituent T is not included in the number of carbon atoms mentioned above. For example, a benzyl group is regarded as an alkyl group having a single carbon atom substituted with a phenyl group and not regarded as an alkyl group having 7 carbon atoms substituted with a phenyl group. Furthermore, when the above monovalent substituent R has a substituent T, the substituent T may be plural.

In the constituent units represented by the above general formulas (1) to (4), X represents a divalent group containing at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group. The aromatic hydrocarbon group, saturated or unsaturated alicyclic hydrocarbon group, linear or branched, saturated or unsaturated aliphatic hydrocarbon group, and heterocyclic group may be substituted or unsubstituted. X may contain a hetero atom or an ether group, a sulfide group, a carbonyl group, a hydroxy group, an amino group, a sulfoxide group or a sulfone group.

Herein, examples of the aromatic hydrocarbon group include, but not particularly limited to, an o-phenylene group, a m-phenylene group, a p-phenylene group, a methylphenylene group, an o-xylylene group, a m-xylylene group, a p-xylylene group, a naphthylene group, an anthracenylene group, a phenanthrylene group, a biphenylene group and a fluonylene group. Examples of the alicyclic hydrocarbon group include, but not particularly limited to, cycloalkenylene groups such as a cyclopentylene group, a cyclohexylene group, a methylcyclohexylene group, a cycloheptylene group and a cyclooctylene group; and cycloalkenylene groups such as a cyclohexycenylene group. Examples of the aliphatic hydrocarbon group include, but not particularly limited to, linear or branched alkylene groups such as a methylene group, an ethylene group, a trimethylene group, a propylene group, an isopropylidene group, a tetramethylene group, an isobutylidene group, a sec-butylidene group, a pentamethylene group, a hexamethylene group, a heptamethylene group, an octamethylene group, a nonamethylene group and a dacamethylene group; and alkenylene groups such as a vinylene group, a propenylene group, a 1-butenylene group, a 2-butenylene group, a 1,3-butadienylene group, a 1-pentenylene group, a 2-pentenylene group, a 1-hexenylene group, a 2-hexenylene group and a 3-hexenylene group. These may further have a substituent. Specific examples thereof include, but not particularly limited to, a halogen, an alkoxy group, a hydroxy group, a carboxyl group, a carboalkoxy group, an amino group, an acyl group, a thio group (for example, an alkylthio group, a phenylthio group, a tolylthio group and a pyridylthio group), an amino group (for example, an unsubstituted amino group, a methylamino group, a dimethylamino group and a phenylamino group), a cyano group and a nitro group.

The tetralin ring-containing polyester compound having the constituent unit represented by the above general formula (1) can be obtained, for example, by polycondensation of a dicarboxylic acid having a tetralin ring or a derivative (I) thereof and a diol or a derivative (II) thereof.

Examples of the dicarboxylic acid having a tetralin ring or a derivative (I) thereof include compounds represented by the following general formula (8). The dicarboxylic acids having a tetralin ring or derivatives (I) thereof can be used alone or in combination with two or more.

[Formula 3]

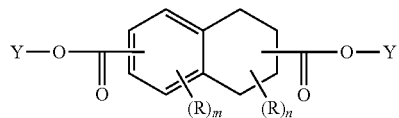

(8)

where R each independently represents a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, an heterocyclic thio group and an imido group, these of which may further have a substituent; m represents an integer of 0 to 3; n represents an integer of 0 to 6, and at least one hydrogen atom is bound to the benzyl position of the tetralin ring; and Y each independently represent a hydrogen atom or an alkyl group.

Note that a compound represented by the above general formula (8) can be obtained by reacting, for example, a dicarboxylic acid having a naphthalene ring represented by the following general formula (9) or a derivative thereof with hydrogen.

[Formula 4]

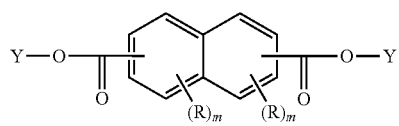

(9)

where R each independently represent a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, an heterocyclic thio group and an imido group, these of which may further have a substituent; m each independently represent an integer of 0 to 3; and Y each independently represent a hydrogen atom or an alkyl group.

Examples of the diol or a derivative (II) thereof include ethylene glycol, diethylene glycol, triethylene glycol, polyethylene glycol, propylene glycol, dipropylene glycol, polypropylene glycol, 1,3-propanediol, 2-methyl-1,3-propanediol, 1,3-butanediol, 1,4-butanediol, 1,5-pentanediol, 1,6-hexanediol, 1,7-heptanediol, 1,8-octanediol, 1,9-nonandiol, neopentyl glycol, 1,4-cyclohexanedimethanol, 2-phenylpropanediol, 2-(4-hydroxyphenyl)ethyl alcohol, α,α-dihydroxy-1,3-diisopropylbenzene, α,α-dihydroxy-1,4-diisopropylbenzene, o-xylene glycol, m-xylene glycol, p-xylene glycol, hydroquinone, 4,4-dihydroxyphenyl and naphthalene diol or derivatives of these. Diols or derivatives (II) thereof can be used alone or in combination with two or more.

A tetralin ring-containing polyester compound containing a constituent unit represented by the above general formula (2) can be obtained, for example, by polycondensation of a diol having a tetralin ring or a derivative (III) thereof and a dicarboxylic acid or a derivative (IV) thereof.

Examples of the diol having a tetralin ring or a derivative (III) thereof include compounds represented by the following general formula (10). The diol having a tetralin ring or derivatives (III) thereof can be used alone or in combination with two or more.

[Formula 5]

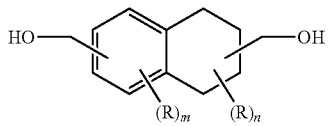

(10)

where R each independently represent a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m represents an integer of 0 to 3; n represents an integer of 0 to 6, and at least one hydrogen atom is bound to the benzyl position of the tetralin ring.

Note that a compound represented by the above general formula (10) can be obtained by reacting, for example, a diol having a naphthalene ring represented by the following general formula (11) or a derivative thereof with hydrogen.

[Formula 6]

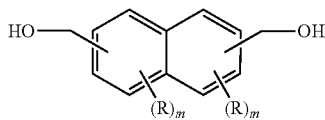

(11)

where R each independently represent a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m each independently represent an integer of 0 to 3.

Examples of the dicarboxylic acid or a derivative (IV) thereof include benzene dicarboxylic acids such as oxalic acid, malonic acid, succinic acid, glutaric acid, adipic acid, pimelic acid, suberic acid, azelaic acid, sebacic acid, undecane diacid, dodecane diacid, 3,3-dimethylpentane diacid, phthalic acid, isophthalic acid and terephthalic acid, and naphthalene dicarboxylic acids such as 2,6-naphthalene dicarboxylic acid, anthracene dicarboxylic acid, phenyl malonic acid, phenylene diacetic acid, phenylene dibutyric acid, 4,4-diphenyletherdicarboxylic acid and p-phenylene dicarboxylic acid or derivatives of these. Dicarboxylic acids or derivatives (IV) thereof can be used alone or in combination with two or more.

The tetralin ring-containing polyester compound containing a constituent unit represented by the above general formula (3) or (4) can be obtained by polycondensation of, for example, a hydroxy carboxylic acid having a tetralin ring or a derivative (V) thereof.

Examples of the hydroxycarboxylic acid having a tetralin ring or a derivative (V) thereof include compounds represented by the following general formula (12) or (13). The hydroxycarboxylic acids having a tetralin ring or derivatives (V) thereof can be used alone or in combination with two or more.

[Formula 7]

(12)

(13)

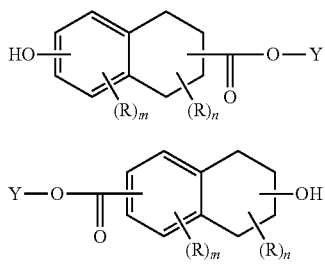

where R each independently represent a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m represents an integer of 0 to 3; n represents an integer of 0 to 6, and at least one hydrogen atom is bound to the benzyl position of the tetralin ring; and Y each independently represent a hydrogen atom or an alkyl group.

A tetralin ring-containing polyester compound containing a constituent unit represented by the above general formula (1) or (2) can be also obtained, for example, by a hydrogenation reaction of a polyester compound containing a constituent unit represented by the following general formula (14) or (15).

[Formula 8]

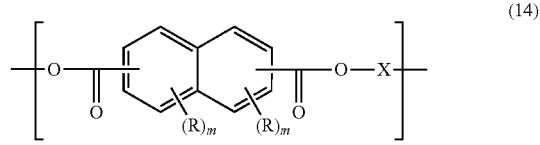

(14)

where R each independently represent a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m each independently represent an integer of 0 to 3; X represents a divalent group containing at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

[Formula 9]

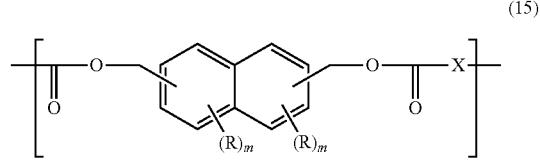

(15)

where R each independently represent a monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; m each independently represent an integer of 0 to 3; X represents a divalent group containing at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

Specific examples of the monovalent substituents represented by R and the divalent group represented by X in the constituent units represented by the above general formulas (8) to (15) are the same as those described in the constituent units represented by the above general formulas (1) to (4). Thus, repetition of explanation is avoided herein.

The tetralin ring-containing polyester compound to be used in the oxygen-absorbing resin composition of the embodiment may contain another constituent unit having a tetralin ring other than the constituent units represented by the above general formulas (1) to (4) and/or a constituent unit having no tetralin ring as a copolymerization component(s). Specifically, the compounds mentioned above as a diol or a derivative (II) thereof and a dicarboxylic acid or a derivative (IV) thereof can be used as the copolymerization component(s).

As more preferable compounds among the tetralin ring-containing polyester compounds containing a constituent unit represented by the above general formula (1), tetralin ring-containing polyester compounds containing constituent units represented by the above formulas (5) to (7) and tetralin ring-containing polyester compounds containing constituent units represented by the following formulas (16) to (18) are mentioned.

[Formula 10]

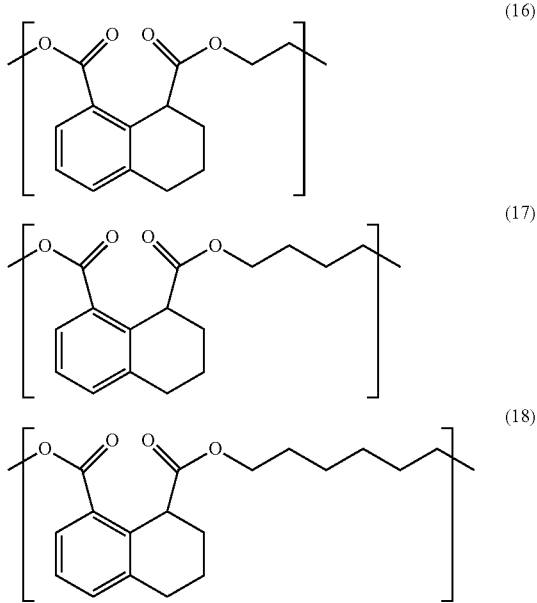

(16)

(17)

(18)

The molecular weight of the above tetralin ring-containing polyester compounds, which can be appropriately specified in consideration of desired performance, handling property, etc., is not particularly limited. Generally, the weight average molecular weight (Mw) is preferably $1.0 \times 10^3$ to $8.0 \times 10^6$ and more preferably $5.0 \times 10^3$ to $5.0 \times 10^6$. Similarly, the number average molecular weight (Mn) thereof is preferably $1.0 \times 10^3$ to $1.0 \times 10^6$ and more preferably $5.0 \times 10^3$ to $5.0 \times 10^4$. Note that the molecular weights used herein each refer to a polystyrene equivalent value. Note that the above tetralin ring-containing polyester compounds can be used alone or in combination with two or more.

The glass transition temperature (Tg) of a tetralin ring-containing polyester compound as mentioned above, which is not particularly limited, is preferably 0 to 90° C. and more preferably 10 to 80° C. Note that the glass transition temperature herein refers to a value measured by differential scanning calorimetry.

A method for producing a tetralin ring-containing polyester compound as mentioned above is not particularly limited and any one of methods for producing a polyester conventionally known can be applied. As the method for producing a polyester, a melt polymerization method such as a transesterification method, a direct esterification method, a solution polymerization method or the like is mentioned. Of them, a transesterification method or a direct esterification method is preferable since raw materials are easily obtained.

In producing a tetralin ring-containing polyester compound, a conventional catalyst such as a transesterification catalyst, an esterification catalyst and a polycondensation catalyst, a conventional stabilizer such as an etherification inhibitor, a heat stabilizer and a photo stabilizer, and a polymerization moderator, etc. may be used. The types and use amounts of these may be appropriately selected depending upon the reaction rate, the molecular weight of a tetralin ring-containing polyester compound, glass transition temperature, viscosity, color tone, safety, heat stability, weather resistance, elution properties themselves, etc. and are not particularly limited. Examples of the catalyst as mentioned above include compounds of metals such as zinc, lead, cerium, cadmium, manganese, cobalt, lithium, sodium, potassium, calcium, nickel, magnesium, vanadium, aluminum, titanium, antimony and tin (for example, a fatty acid salt, a carbonate, a phosphate, a hydroxide, a chloride, an oxide, and an alkoxide) and magnesium metal. These can be used alone or in combination with two or more.

Note that the limiting viscosity of a tetralin ring-containing polyester compound (measurement value at 25° C. using a solvent mixture containing phenol and 1,1,2,2-tetrachloroethane in a mass ratio of 6:4), which is not particularly limited, is preferably 0.1 to 2.0 dL/g and more preferably 0.5 to 1.5 dL/g in view of moldability of the tetralin ring-containing polyester compound.

The above tetralin ring-containing polyester compounds all have hydrogen at the benzyl position of the tetralin ring. Since the hydrogen at the benzyl position is removed by using a tetralin ring-containing polyester compound in combination with a transition metal catalyst as mentioned above, more excellent oxygen absorptivity is exhibited.

The oxygen-absorbing resin composition of the embodiment is significantly suppressed in odor generation after absorption of oxygen. The reason is not elucidated; however, for example, the following oxidation reaction mechanism is presumable. In the tetralin ring-containing polyester compound as mentioned above, first hydrogen at the benzyl position of a tetralin ring is removed to produce a radical. The radical then reacts with oxygen to oxidize carbon at the benzyl position. In this manner, a hydroxy group or a ketone group is considered to be produced. Because of this, it is presumed that, in the oxygen-absorbing resin composition of the embodiment, a molecular chain of a main oxygen-absorbing component is not cut by an oxidation reaction as is in the prior art and the structure of a tetralin ring-containing polyester compound is maintained, with the result that a low molecular weight organic compound serving as a cause of odor is rarely produced after absorption of oxygen.

<Transition Metal Catalyst>

As the transition metal catalyst to be used in the oxygen-absorbing resin composition of the embodiment, any catalyst known in the art can be appropriately selected and used as long as it can serve as a catalyst for the oxidation reaction of a tetralin ring-containing polyester compound as mentioned above. The transition metal catalyst is not particularly limited.

Specific examples of such a transition metal catalyst include organic acid salts, halides, phosphates, phosphites, hypophosphites, nitrates, sulfates, oxides and hydroxides of transition metals. Examples of the transition metal to be contained in the transition metal catalyst include, but not limited to, titanium, vanadium, chromium, manganese, iron, cobalt, nickel, copper, zinc, ruthenium and rhodium. Of them, manganese, iron, cobalt, nickel and copper are preferable. Examples of the organic acids include, but not limited to, acetic acid, propionic acid, octanoic acid, lauric acid, stearic acid, acetylacetone, dimethyldithiocarbamic acid, palmitic acid, 2-ethylhexanoic acid, neodecanoic acid, linoleic acid, tall acid, oleic acid, capric acid and naphthenic acid. The transition metal catalyst is preferably a combination of a transition metal as mentioned above and an organic acid, and more preferably a combination of a transition metal such as manganese, iron, cobalt, nickel or copper and an organic acid such as acetic acid, stearic acid, 2-ethylhexanoic acid, oleic acid or naphthenic acid. Note that transition metal catalysts can be used alone or in combination with two or more.

In the oxygen-absorbing resin composition of the embodiment, the content rate of a tetralin ring-containing polyester compound and a transition metal catalyst, which can be appropriately specified depending upon the types of tetralin ring-containing polyester compound and transition metal catalyst to be used and the desired performances thereof, is not particularly limited. In view of the amount of oxygen absorbed of oxygen-absorbing resin composition, the content of a transition metal catalyst is preferably 0.001 to 10 parts by mass in terms of transition metal based on 100 parts by mass of a tetralin ring-containing polyester compound, and more preferably 0.002 to 2 parts by mass, and further preferably 0.005 to 1 part by mass.

<Other Thermoplastic Resin>

The oxygen-absorbing resin composition of the embodiment, if necessary, may further contain another thermoplastic resin other than a tetralin ring-containing polyester compound as mentioned above. If another thermoplastic resin is used in combination, moldability and handling property can be enhanced.

As another thermoplastic resin, those known in the art can be appropriately used. Examples thereof include, but not limited to, polyolefins such as random or block copolymers of α-olefins such as a low-density polyethylene, a medium-density polyethylene, a high-density polyethylene, a linear and low-density polyethylene, a linear and extremely low-density polyethylene, a polypropylene, poly-1-butene, poly-4-methyl-1-pentene or ethylene, propylene, 1-butene, and 4-methyl-1-pentene; acid-modified polyolefins such as maleic anhydride-grafted polyethylene and maleic anhydride-grafted polypropylene; ethylene-vinyl compound copolymers such as an ethylene-vinyl acetate copolymer, an ethylene-vinyl chloride copolymer, an ethylene-(meth)acrylate copolymer, an ion crosslinked product (ionomer) thereof and an ethylene-methyl methacrylate copolymer; styrene resins such as polystyrene, an acrylonitrile-styrene copolymer and an α-methylstyrene-styrene copolymer; polyvinyl compounds such as poly(methyl acrylate) and poly(methyl methacrylate); polyamides such as nylon 6, nylon 66, nylon 610, nylon 12, poly(metaxylylene adipamide) (MXD6); polyesters such as poly(ethylene terephthalate) (PET), poly(butylene terephthalate) (PBT), poly(trimethylene terephthalate) (PTT), poly(ethylene naphthalate)(PEN), glycol-modified poly(ethylene terephthalate) (PETG), poly(ethylene succinate) (PES), poly(butylene succinate) (PBS), polylactate, polyglycolate, polycaprolactone and polyhydroxyalkanoate; polycarbonates; polyethers such as polyethylene oxide; and mixtures of these. These thermoplastic resins can be used alone or in combination with two or more.

The oxygen-absorbing resin composition of the embodiment more preferably contains a polyolefin resin as another thermoplastic resin. Examples of the polyolefin resin include polyethylenes such as a high-density polyethylene, a medium-density polyethylene, a low-density polyethylene, a linear and low-density polyethylene and an extremely low-density polyethylene as mentioned above, and a polyethylene obtained in the presence of a metallocene catalyst; polypropylenes such as a propylene homopolymer, a propylene-ethylene block copolymer and a propylene-ethylene random copolymer; polystyrenes; polymethylpentenes; and cyclic polyolefins such as a cycloolefin polymer and a cycloolefin copolymer using a cyclic olefin. These can be used alone or in combination with two or more. Note that in blending each of these polyolefin resins, an ethylene-vinyl acetate copolymer, an ethylene-methyl acrylate copolymer, an ethylene-ethyl acrylate copolymer, an ethylene-acrylic acid copolymer, an ethylene-methacrylic acid copolymer, an ethylene-methyl methacrylate copolymer, a thermoplastic elastomer, etc. may be added. Note that in consideration of moldability and processability in molding the oxygen-absorbing resin composition of the embodiment into a film, the melt flow rate (hereinafter, expressed as "MFR") of a polyolefin resin is preferably 1 to 35 g/10 minutes at 200° C. or 2 to 45 g/10 minutes at 240° C. Note that in the specification, unless otherwise specified, MFR refers to a value measured by an apparatus in accordance with JIS K7210 at a predetermined temperature under application of a load of 2160 g and represented by a unit of "g/10 minutes" together with the measurement temperature. However, in view of oxygen-absorbing performance, a polyolefin resin having an oxygen transmission coefficient of 50 to 200 cc·mm/(m²·day·atm) (23° C., 60% RH) is preferable. If a polyolefin resin having an oxygen transmission coefficient within the range is used, more satisfactory oxygen-absorbing performance tends to be easily obtained. Furthermore, in view of recycling and reprocessing of offcuts generated during manufacturing, it is preferable to add an antioxidant to a polyolefin resin.

In consideration of miscibility with a tetralin ring-containing polyester compound as mentioned above, it is preferable to add a maleic anhydride-modified polyolefin resin in blending a polyolefin resin. In this case, the amount of maleic anhydride-modified polyolefin resin added is not particularly limited; however, the amount added is preferably 1 to 30 parts by mass based on 100 parts by mass of the polyolefin resin and more preferably 3 to 15 parts by mass.

When the oxygen-absorbing composition of the embodiment contains a thermoplastic resin, the content rate of the thermoplastic resin is preferably 10 to 80 parts by mass based on the total amount (100 parts by mass) of a tetralin ring-containing polyester compound and the thermoplastic resin, in view of oxygen-absorbing performance and moldability, more preferably 15 to 70 parts by mass, and further preferably 20 to 60 parts by mass.

When the oxygen-absorbing resin composition of the embodiment contains a polyolefin resin, the content rate of a tetralin ring-containing polyester compound is not particularly limited; however, the content rate is preferably 10 to 80 parts by mass based on the total amount (100 parts by mass) of the tetralin ring-containing polyester compound and the polyolefin resin, more preferably 15 to 70 parts by mass and further preferably 20 to 60 parts by mass. If the content of the tetralin ring-containing polyester compound falls within the preferable range, the amount of oxygen absorbed tends to be high compared to that in the case where the content is less than 10 parts by mass, and processability with the polyolefin resin tends to be more satisfactory compared to that in the case where the content exceeds 80 parts by mass.

The thermoplastic resin to be added, if necessary, to a tetralin ring-containing polyester compound and a transition metal catalyst can be mixed in accordance with a method known in the art. If these are kneaded by use of an extruder, an oxygen-absorbing resin composition having higher dispersibility can be obtained.

<Additives>

The oxygen-absorbing resin composition of the embodiment herein may contain additives known in the art other than the aforementioned components, as long as the effect of the embodiment is not excessively damaged. Examples of such optional components include, but not particularly limited to, additives such as a drying agent, a pigment such as titanium oxide, a dye, an antioxidant, a slipping agent, an antistatic agent and a stabilizer; fillers such as calcium carbonate, clay, mica and silica; and a deodorant.

The oxygen-absorbing resin composition of the embodiment may further contain a radical generator and a photo initiator, if necessary, in order to facilitate an oxygen absorption reaction. Specific examples of the radical generator include various types of N-hydroxy imide compounds. Specific examples thereof include, but not particularly limited to, N-hydroxysuccinimide, N-hydroxymaleimide, N,N'-dihydroxycyclohexanetetracarboxydiimide, N-hydroxyphthalimide, N-hydroxytetrachlorophthalimide, N-hydroxytetrabromophthalimide, N-hydroxyhexahydrophthalimide, 3-sulfonyl-N-hydroxyphthalimide, 3-methoxycarbonyl-N-hydroxyphthalimide, 3-methyl-N-hydroxyphthalimide, 3-hydroxy-N-hydroxyphthalimide, 4-nitro-N-hydroxyphthalimide, 4-chloro-N-hydroxyphthalimide, 4-methoxy-N-hydroxyphthalimide, 4-dimethylamino-N-hydroxyphthalimide, 4-carboxy-N-hydroxyhexahydrophthalimide, 4-methyl-N-hydroxyhexahydrophthalimide, N-hydroxyhetimide, N-hydroxyhimimide, N-hydroxytrimellitimide and N,N-dihydroxypyromellitdiimide. Specific examples of the photo initiator include, but not particularly limited to, benzophenone and a derivative thereof, a thiazine dye, a metal porphyrin derivative and an anthraquinone derivative. Note that these radical generators and photo initiators can be used alone or in combination with two or more.

<Usage>

To the oxygen-absorbing resin composition of the embodiment, a known granulation method or a known molding method such as an extrusion molding can be applied. The composition is molded into, for example, powdery, granular, pellet, film or sheet-forms or other small-piece forms. The oxygen-absorbing resin molded article thus obtained can be used directly as an oxygen absorbent. Alternatively, if the obtained oxygen-absorbing resin molded article is packed in an air-permeable packaging material, the molded article can also be used as an oxygen absorbent packaging body. Furthermore, if the oxygen-absorbing resin composition of the embodiment is molded into film-form or sheet-form, the molded article can also be used in the form of a label, a card, a packing, etc. Note that a molded article having a thickness of 0.1 to 500 µm is specified as a film, whereas a molded article having a thickness exceeding 500 µm is specified as a sheet.

It is preferable that a pellet-form oxygen-absorbing resin molded article herein is further ground into powdery grains when used in order to increase the contact area with oxygen to thereby effectively deliver oxygen-absorbing performance.

Note that as the air-permeable packaging material, which is not particularly limited, a known packaging material having air permeability can be applied. In view of sufficiently exerting the oxygen absorption effect, an air-permeable packaging material having high air permeability is preferred. Specific examples of the air-permeable packaging material include, but not particularly limited to, highly air-permeable packaging materials used in various usages, including paper sheets such as Japanese paper, machine-made paper and rayon paper; non-woven clothes using various types of fibers obtained from pulp, cellulose and a synthetic resin; a plastic film or a porous plastic film; or a microporous film obtained by adding calcium carbonate etc., followed by drawing it; and a laminate obtained by stacking two types or more selected from these. As the plastic film, laminate films, each formed by laminating and attaching a film of e.g., a polyethylene terephthalate, a polyamide, a polypropylene or a polycarbonate film and a film serving as a sealing film and formed of a polyethylene, an ionomer, a polybutadiene, an ethylene acrylate copolymer, an ethylene methacrylate copolymer or an ethylene vinyl acetate copolymer, can be used.

Note that if the oxygen-absorbing resin composition of the embodiment is molded into a film form or a sheet form and put in use, it is preferable to form micro voids in the film or the sheet, for example, by drawing. Owing to this operation, the oxygen permeability of the film or sheet to be molded can be enhanced, with the result that the oxygen-absorbing performance of the tetralin ring-containing polyester compound mentioned above tends to be extremely effectively delivered. Furthermore, if an oxygen-absorbing resin composition contains a polyolefin resin, the polyolefin resin and a tetralin ring-containing polyester compound may possibly form an island structure in a film or a sheet. In this case, it is preferable to form voids in the interface between them, for example, by drawing. As the polyolefin resin that is used in drawing a film or a sheet in this way, a high-density polyethylene is preferable.

The oxygen-absorbing resin composition of the embodiment molded into a film form or a sheet form can be not only used as a packaging material or a packaging container in the form of a single-layer form but also used in combination with another substrate in the form of a laminate. Typical example of such a laminate is a laminate obtained by stacking at least one layer formed of the oxygen-absorbing resin composition of the embodiment and at least one layer selected from other resin layers, paper substrate layers or metal foil layers. This laminate can be used as an oxygen-absorbing multi-layer packaging material and an oxygen-absorbing multi-layer packaging container. Note that generally, the oxygen-absorbing resin composition (layer) of the embodiment molded into a film form or a sheet form is preferably provided to an interior side rather than the outer surface of a container etc. so as not to be exposed at the outer surface of the container etc. In view of avoiding direct contact with the content of a container, the oxygen-absorbing resin composition (layer) of the embodiment molded into a film form or a sheet form is preferably provided outer than the inner surface of the container etc. Likewise, in using the oxygen-absorbing resin composition (layer) of the embodiment in a multilayer body, it is preferable that the composition is molded into a film form or a sheet form and arranged as at least one intermediate layer.

As one preferable aspect of the laminate mentioned above, an oxygen-absorbing multilayer body having at least three layers, i.e., a sealant layer containing a thermoplastic resin, an oxygen-absorbing layer containing the oxygen-absorbing resin composition of the embodiment and a gas barrier layer containing a gas barrier substance, in this order is mentioned. The phrase "having at least three layers in this order" means that the sealant layer, oxygen-absorbing layer and gas barrier layer are arranged in this order; and is a concept including not only an aspect where a sealant layer, an oxygen-absorbing layer and a gas barrier layer are directly stacked (hereinafter, expressed as a "sealant layer/oxygen-absorbing layer/gas barrier layer") but also an aspect where one or more other layers such as a resin layer, a metal foil layer or an adhesive layer are interposed between a sealant layer and an oxygen-absorbing layer or between an oxygen-absorbing layer and a gas barrier layer (hereinafter, referred to as an "intermediate layer") (for example, "sealant layer/resin layer/oxygen-absorbing layer/adhesion layer/gas barrier layer", and "sealant layer/resin layer/adhesion layer/oxygen-absorbing layer/adhesion layer/resin layer/adhesion layer/gas barrier layer/adhesion layer/support") (the same applied hereinafter without an exception).

As another preferable aspect of the laminate mentioned above, an oxygen-absorbing multilayer body having at least three layers, i.e., a sealant layer having a polyolefin resin, an oxygen-absorbing layer containing the oxygen-absorbing resin composition of the embodiment and a gas barrier layer containing a gas barrier substance in this order, is mentioned.

As the thermoplastic resin and polyolefin resin used in the sealant layer, the same thermoplastic resins and polyolefin resins described in the oxygen-absorbing resin composition of the embodiment can be used. It is preferable that the thermoplastic resin and polyolefin resin to be used in the sealant layer are appropriately selected in consideration of compatibility with other layers (oxygen-absorbing layer, gas barrier layer, resin layer, adhesive layer, support, etc.) in adjacent to the sealant layer.

As the gas barrier substance to be used as a gas barrier layer, a gas barrier thermoplastic resin, a gas barrier thermosetting resin, silica, alumina, aluminum, etc., (as vapor deposition films) and a metal (as aluminum in the form of foil) can be used. Examples of the gas barrier thermoplastic resin include an ethylene-vinyl alcohol copolymer, MXD6 and poly(vinylidene chloride). As the gas barrier thermosetting resin, a gas barrier epoxy resin, for example, "MAXIVE" manufactured by Mitsubishi Gas Chemical Company, Inc., can be mentioned.

Note that, in consideration of processability of the oxygen-absorbing multilayer body as mentioned above in manufacturing, it is preferably to interpose an intermediate layer containing a thermoplastic resin such as a polyolefin resin between a gas barrier layer containing a gas barrier substance and an oxygen-absorbing layer containing the oxygen-absorbing resin composition of the embodiment. It is preferable that the thickness of the intermediate layer is substantially the same as the thickness of the sealant layer, in view of processability. Herein in consideration of variation by processing, the phrase "substantially the same" means that the ratio of thickness values falls within ±10%.

In the above oxygen-absorbing multilayer body, the thickness of the oxygen-absorbing layer, which is not particularly limited, is preferably 5 to 100 µm and more preferably 10 to 50 µm. If the thickness of the oxygen-absorbing layer falls within the preferable range, oxygen-absorbing performance tends to be more improved without excessively damaging processability and economic aspect, compared to an oxygen-absorbing layer having a thickness outside the range.

In contrast, in the above oxygen-absorbing multilayer body, the thickness of the sealant layer, which is not particularly limited, is preferably 2 to 50 µm and more preferably 5 to 30 µm. If the thickness of the sealant layer falls within the preferable range, the oxygen-absorbing rate of the oxygen-absorbing layer tends to be more enhanced without excessively damaging processability and economic aspect, compared to a sealant layer having a thickness outside the range. Note that in consideration of processability in molding the oxygen-absorbing resin composition of the embodiment into a film-form or a sheet-form, the thickness ratio of the sealant layer and the oxygen-absorbing layer is preferably 1:0.5 to 1:3 and more preferably 1:1 to 1:2.5.

In the above oxygen-absorbing multilayer body, the thickness of the gas barrier layer, which may be appropriately specified depending upon the type of gas barrier substance to be used and gas barrier performance required, is not particularly limited. In view of processability and economic aspect, the thickness is preferably 1 to 100 µm and more preferably 2 to 80 µm.

Note that the above oxygen-absorbing multilayer body, if a paper substrate is stacked on the gas barrier layer as the outer layer, can be used as an oxygen-absorbing paper container. In this case, in view of moldability into a paper container, the thickness of the layers inside the gas barrier layer is preferably 100 µm or less, more preferably 80 µm or less, and further preferably 60 µm or less, for example, 50 µm or less.

As a method for manufacturing an oxygen-absorbing multilayer body as mentioned above, which is not particularly limited, known methods such as a coextrusion method, a laminating method and a coating method can be applied depending upon e.g., the properties of the material, purpose of processing and processing step. For example, a film or a sheet can be formed by a manufacturing method of extruding a molten resin composition through e.g., a T die and a circular die by an extruder attached therewith or by a method of applying an adhesive to an oxygen-absorbing film or a sheet and adhering it to another film or sheet. Also, if molten resins are simultaneously injected or sequentially injected through multi-layered multiple dies into an injection mold by use of an injector, a multilayer container or a preform for manufacturing a container having a predetermined shape can be formed. The preform is heated to a drawing temperature and stretched in the axial direction and simultaneously stretched in the circumferential direction in accordance with stretch blow-molding by hydrostatic pressure to obtain a bottle.

For example, a film-form oxygen-absorbing multilayer body can be further processed into a bag-form or a cover material. For example, a sheet-form oxygen-absorbing multilayer body is thermoformed into an oxygen-absorbing multilayer container of a predetermined shape such as a tray, a cup, a bottle and a tube by a molding method such as vacuum molding, air-pressure forming and plug assist molding. The bag-form container, if it is filled with stuff such as food and an open hole is provided, can be preferably used as a pouch for microwave cooking provided with a hole for easily releasing water vapor during microwave cooking.

In using the oxygen-absorbing resin composition of the embodiment and various types of moldings such as laminates using the composition, initiation of an oxygen absorption reaction can be facilitated and an oxygen-absorbing rate can be increased by irradiation of an energy beam. Examples of the usable energy beam include visible ray, UV ray, X-ray, electron ray and γ ray. The amount of irradiation energy can be appropriately selected depending upon the type of energy line to be used.

The oxygen-absorbing resin composition of the embodiment and various types of moldings such as laminates and containers using the composition do not require a moisture content for absorbing oxygen. In other words, oxygen can be absorbed regardless of the presence or absence of the moisture content of an article to be packaged. Thus, the composition and moldings can be used in a wide variety of uses no matter which type of article to be packaged is contained. In particular, no odor is produced after absorption of oxygen, the composition and moldings can be particularly preferably used in e.g., foods, cooking foods, beverages, health foods and medicinal products. More specifically, since the oxygen-absorbing resin composition of the embodiment and various types of moldings such as laminates using the composition are excellent in oxygen-absorbing performance in a wide range of humidity conditions from low humidity to high humidity (relative humidity 0% to 100%) and excellent in taste and flavor retention property of a content, they are suitable for packaging various articles. In addition, unlike a conventional oxygen-absorbing resin composition using iron powder, the oxygen-absorbing resin composition of the embodiment can be suitably used for storing an article to be packaged (for example, alcohol beverages and carbonate beverages) which cannot be stored because of the presence of iron.

Specific examples of the article to be packaged include, but not particularly limited to, beverages such as cow milk, juice, coffee, tea and alcohol beverage; liquid seasonings such as source, soy sauce, noodle broth and dressing; cooking foods such as soup, stew and curry; paste foods such as jam and mayonnaise; seafood products such as tuna and fish and shellfish; processed milk products or processed egg products such as cheese, butter and egg; processed livestock products such as meat, salami sausage, sausage and ham; vegetables such as carrot, potato, asparagus and shiitake mushroom; fruits; egg; noodles; rices such as rice and polished rice; cereals such as beans; processed rice foods or processed cereal foods such as steamed rice, festive red rice, rice cake and rice gruel; confectionaries such as adzuki-bean jelly, pudding, cake and steamed bean-jam buns; dry foods (food having a low water activity) such as powdered seasoning, powdered coffee, coffee bean, tea, powdered milk for infants, cooking food for infants, powdered dietary food, nursing care cooking food, dry vegetable, Japanese cracker and rice cracker; chemical products such as an adhesive, a gluing agent, an agrichemical and a pesticide; medicinal products; health foods such as a vitamin supplement; pet foods; sundry articles such as a cosmetic, a shampoo, a conditioner and a detergent; and other various articles. Particularly, the oxygen-absorbing resin composition of the embodiment is suitable for packaging materials for an article to be packaged easily degrading in the presence of oxygen. Examples of such an article to be packaged include beverages such as beer, wine, fruit juice beverage, fruit juice, vegetable juice, carbonate soft drink and tea; foods such as fruit, nut, vegetable, meat products, infant food, coffee, jam, mayonnaise, ketchup, edible oil, dressing, source, food boiled in soy sauce and milk products; and others such as medicinal products and cosmetics. Note that the term "water activity" refers to a scale showing the content of free water in an article and represented by a numeral from 0 to 1. The article containing no water is represented by 0 and pure water is represented by 1. More specifically, the water activity Aw of an article is defined as follows:

$$Aw = P/P_0 = RH/100$$

where P represents a water vapor pressure of a space where an article is sealed and the state of the space reaches equivalent, $P_o$ represents the water vapor pressure of pure water and RH (%) represents the relative humidity of the space.

Note that before and after filling (packaging) of an article to be packaged, the container and the article to be packaged can be sterilized by a method suitable for the article to be packaged. Examples of the sterilization method include heat treatment such as a boiling treatment performed at 100° C. or less, a semi-retort treatment and a retort treat performed at 100° C. or more, and a high retort treatment performed at 130° C. or more; sterilization with an electromagnetic wave such as UV rays, microwave and gamma ray; gas treatment performed with ethylene oxide etc.; and sterilization with a chemical agent such as hydrogen peroxide and hypochlorite.

More specific embodiment using the oxygen-absorbing resin composition of the first embodiment will be described in detail below.

(Second Embodiment)

Now, the second embodiment of the present invention will be described below. Note that repetition of explanation with respect to the same content as in the first embodiment is avoided herein.

[Oxygen-Absorbing Multilayer Body]

The oxygen-absorbing multilayer body of the embodiment at least has an oxygen-absorbing layer (layer A) formed of the oxygen-absorbing resin composition of the first embodiment and a resin layer (layer B) containing a thermoplastic resin.

The layer constitution of the oxygen-absorbing multilayer body of the embodiment is not particularly limited and the number and types of oxygen-absorbing layers (layer A) and resin layers (layer B) are not particularly limited. For example, the multilayer body may be constituted of A/B, i.e., formed of a single-layer A and single-layer B; may be constituted of three layers (B/A/B), i.e., formed of a single-layer A and two layers B; or alternatively may be constituted of five layers (B1/B2/A/B2/B1), i.e., formed of a single-layer A and four layers of two types of B, (two B1 layers and two B2 layers). Furthermore, the multilayer body of the embodiment may contain, if necessary, an optional layer such as an adhesion layer (layer AD). The multilayer body may be constituted of seven layers (for example, B1/AD/B2/A/B2/AD/B1).

[Oxygen-Absorbing Layer (Layer A)]

The oxygen-absorbing layer (layer A) of the oxygen-absorbing multilayer body of the embodiment is formed of an oxygen-absorbing resin composition containing at least one tetralin ring-containing polyester compound having at least one selected from the group consisting of the constituent units represented by the above general formulas (1) to (4) and a transition metal catalyst. The oxygen-absorbing resin composition used herein is the same as described in the first embodiment.

The content rate of the tetralin ring-containing polyester compound in layer A, which is not particularly limited, is preferably 50 mass % or more based on the total amount of layer A, more preferably 70 mass % or more and further preferably 90 mass % or more. If the content rate of a tetralin ring-containing polyester compound is a preferable value or more, the oxygen-absorbing performance tends to be more enhanced, compared to the case where the content rate does not satisfy the above condition.

In the oxygen-absorbing multilayer body of the embodiment, the thickness of the oxygen-absorbing layer (layer A), which can be appropriately specified depending upon the use and desired performance, is not particularly limited; however, the thickness is preferably 1 to 1000 μm, more preferably 2 to 800 μm and further preferably 5 to 700 μm. If the thickness falls within the preferable range mentioned above, the performance of layer A to absorb oxygen can be more enhanced and processability and economic aspect can be maintained at high levels, compared to the case where the thickness does not satisfy the above condition.

[Resin Layer (Layer B) Containing a Thermoplastic Resin]

The resin layer (layer B) of the oxygen-absorbing multilayer body of the embodiment is a layer containing a thermoplastic resin. The content rate of the thermoplastic resin in layer B, which can be appropriately specified, is not particularly limited; however, the content is preferably 70 to 100 mass % based on the total amount of layer B, more preferably 80 to 100 mass % and further preferably 90 to 100 mass %.

The oxygen-absorbing multilayer body of the embodiment may have a plurality of layers B and the constitutions of plural layers B may be the same or different. In the oxygen-absorbing multilayer body of the embodiment, the thickness of layer B, which can be appropriately specified depending upon the use and desired performance, is not particularly limited; however, the thickness is preferably 5 to 1000 μm, more preferably 10 to 800 μm and further preferably 20 to 500 μm, in view of ensuring physical properties required for a multilayer body such as strength including drop resistance and flexibility.

As the thermoplastic resin of layer B in the oxygen-absorbing multilayer body of the embodiment, any thermoplastic resin can be used, in other words, the thermoplastic resin of layer B is not particularly limited. Specifically, thermoplastic resins as exemplified in the first embodiment are mentioned. In particular, layer B of the embodiment preferably contains at least one type of thermoplastic resin selected from the group consisting of a polyolefin, a polyester, a polyamide, an ethylene-vinyl alcohol copolymer, a plant-derived resin and a chlorine resin. The thermoplastic resin to be used in layer B of the embodiment preferably contains a thermoplastic resin other than a tetralin ring-containing polyester compound as described in the first embodiment, in an amount of 50 to 100 mass % based on the total amount of thermoplastic resins, more preferably 70 to 100 mass % and further preferably 90 to 100 mass %.

Now, examples of the thermoplastic resin preferably used in layer B of the oxygen-absorbing multilayer body of the embodiment will be mentioned below.

<Polyolefin>

Specific examples of the polyolefin to be used in layer B of the oxygen-absorbing multilayer body of the embodiment include polyethylenes such as a low-density polyethylene, a medium-density polyethylene, a high-density polyethylene, a linear and low-density polyethylene, and a linear and extremely low-density polyethylene; olefin homopolymers such as a polypropylene, polybutene-1 and poly-4-methyl-pentene-1; ethylene and α-olefin copolymers such as an ethylene-propylene random copolymer, an ethylene-propylene block copolymer, an ethylene-propylene-polybutene-1 copolymer and an ethylene-cyclic olefin copolymer; other ethylene copolymers such as an ethylene-α,β-unsaturated carboxylic acid copolymer such as ethylene-(meth)acrylate copolymer, an ethylene-α,β-unsaturated carboxylic acid ester copolymer such as an ethylene-ethyl (meth)acrylate copolymer, ion crosslinked compound of ethylene-α,β-unsaturated carboxylic acid copolymer and an ethylene-vinyl acetate copolymer; open-ring polymers of a cyclic olefin and hydrogenated compounds thereof; cyclic olefin-ethylene copolymers; and graft-modified polyolefins obtained by modifying these polyolefins with an acid anhydride such as maleic anhydride.

<Polyester>

The polyester that will be described below is a polyester exemplified as a thermoplastic resin for layer B and does not contain a tetralin ring-containing polyester compound according to the first embodiment. As specific examples of the polyester to be used in layer B of the oxygen-absorbing multilayer body of the embodiment, those formed of one or two or more compounds selected from polyvalent carboxylic acids containing a dicarboxylic acid and ester-forming derivatives of these and one or two or more compounds selected from polyhydric alcohols including a glycol; those formed of hydroxy carboxylic acids and ester-forming derivative of these; or those formed of cyclic esters are mentioned. Ethylene terephthalate thermoplastic polyester is preferably a polyester in which a most part of ester repeat units, generally 70 mole % or more thereof, is occupied by an ethylene terephthalate unit and having a glass transition point (Tg) within the range of 50 to 90° C. and a melting point (Tm) within the range of 200 to 275° C. As an ethylene terephthalate thermoplastic polyester, a polyethylene terephthalate is particularly excellent in pressure resistance, heat resistance, thermal pressure resistance, etc. A polyester copolymer containing a small amount of ester unit formed of a dicarboxylic acid such as isophthalic acid and a naphthalene dicarboxylic acid and a diol such as propylene glycol, other than the ethylene terephthalate unit, can also be used.

Specific examples of the dicarboxylic acid include saturated aliphatic dicarboxylic acids such as oxalic acid, malonic acid, succinic acid, glutaric acid, adipic acid, pimelic acid, suberic acid, azelaic acid, sebacic acid, decanedicarboxylic acid, dodecanedicarboxylic acid, tetradecanedicarboxylic acid, hexadecanedicarboxylic acid, 3-cyclobutanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid, 2,5-norbornanedicarboxylic acid and dimer acid or ester-forming derivatives of these; unsaturated aliphatic dicarboxylic acids such as fumaric acid, maleic acid and itaconic acid or ester-forming derivatives of these; naphthalenedicarboxylic acids such as orthophthalic acid, isophthalic acid, terephthalic acid, 1,3-naphthalenedicarboxylic acid, 1,4-naphthalenedicarboxylic acid, 1,5-naphthalenedicarboxylic acid, 2,6-naphthalenedicarboxylic acid and 2,7-naphthalenedicarboxylic acid; aromatic dicarboxylic acids such as 4,4'-biphenyldicarboxylic acid, 4,4'-biphenylsulfonedicarboxylic acid, 4,4'-biphenyletherdicarboxylic acid, 1,2-bis(phenoxy)ethane-p,p'-dicarboxylic acid and anthracenedicarboxylic acid or ester-forming derivatives of these; and metal sulfonate group-containing aromatic dicarboxylic acids such as 5-sodium sulfo-isophthalic acid, 2-sodium sulfo-terephthalic acid, 5-lithium sulfo-isophthalic acid, 2-lithium sulfo-terephthalic acid, 5-potassium sulfo-isophthalic acid and 2-potassium sulfo-terephthalic acid or lower alkyl ester derivatives of these.

Of the aforementioned dicarboxylic acids, particularly, terephthalic acid, isophthalic acid and naphthalene dicarboxylic acid are preferably used in view of the physical properties etc. of the polyesters to be obtained. Note that, if necessary, other dicarboxylic acids may be copolymerized.

Specific examples of the polyvalent carboxylic acids other than these dicarboxylic acids include ethane tricarboxylic acid, propane tricarboxylic acid, butane tetracarboxylic acid, pyromellitic acid, trimellitic acid, trimesic acid, 3,4,3',4'-biphenyltetracarboxylic acid and ester-forming derivatives of these.

Specific examples of the glycol include aliphatic glycols such as ethylene glycol, 1,2-propylene glycol, 1,3-propylene glycol, diethylene glycol, triethylene glycol, 1,2-butylene glycol, 1,3-butylene glycol, 2,3-butylene glycol, 1,4-butylene glycol, 1,5-pentanediol, neopentyl glycol, 1,6-hexanediol, 1,2-cyclohexanediol, 1,3-cyclohexanediol, 1,4-cyclohexanediol, 1,2-cyclohexane dimethanol, 1,3-cyclohexane dimethanol, 1,4-cyclohexane dimethanol, 1,4-cyclohexane diethanol, 1,10-dacamethylene glycol, 1,12-dodecane diol, polyethylene glycol, poly(trimethylene glycol) and poly(tetramethylene glycol); and aromatic glycols such as hydroquinone, 4,4'-dihydroxy bisphenol, 1,4-bis(3-hydroxyethoxy)benzene, 1,4-bis(β-hydroxyethoxyphenyl)sulfone, bis(p-hydroxyphenyl)ether, bis(p-hydroxyphenyl)sulfone, bis(p-hydroxyphenyl)methane, 1,2-bis(p-hydroxyphenyl)ethane, bisphenol A, bisphenol C, 2,5-naphthalene diol and glycols formed by adding an ethylene oxide to these glycols.

Of the glycols mentioned above, particularly, ethylene glycol, 1,3-propylene glycol, 1,4-butylene glycol, and 1,4-cyclohexane dimethanol are preferably used as a main component.

Specific examples of the polyhydric alcohols other than these glycols include trimethylol methane, trimethylol ethane, trimethylol propane, pentaerythritol, glycerol and hexane triol.

Specific examples of the hydroxy carboxylic acid include, lactic acid, citric acid, malic acid, tartaric acid, hydroxyacetic acid, 3-hydroxybutyrate, p-hydroxybenzoate, p-(2-hydroxyethoxy)benzoate, 4-hydroxycyclohexanecarboxylic acid and ester-forming derivatives of these.

Specific examples of the cyclic esters include ε-caprolactone, β-propiolactone, β-methyl-β-propiolactone, δ-valerolactone, glycolide and lactide.

Specific examples of the ester-forming derivatives of a polyvalent carboxylic acid and a hydroxy carboxylic acid include alkyl esters, acid chlorides and acid anhydrides of these.

Of the aforementioned ones, a polyester containing terephthalic acid or an ester-forming derivative thereof or a naphthalene dicarboxylic acid or an ester-forming derivative thereof as a main acid component and an alkylene glycol as a main glycol component is preferable.

Note that the polyester containing terephthalic acid or an ester-forming derivative thereof as a main acid component is a polyester preferably containing the terephthalic acid or an ester-forming derivative thereof in total in an amount of 70 mole % or more based on the total of the acid components, more preferably in an amount of 80 mole % or more and further preferably in an amount of 90 mole % or more. Similarly, the polyester containing naphthalene dicarboxylic acids or ester-forming derivatives thereof as a main acid component is a polyester preferably containing naphthalene dicarboxylic acids or ester-forming derivatives thereof in total in an amount of 70 mole % or more, more preferably in an amount of 80 mole % or more and further preferably in an amount of 90 mole % or more.

Of the aforementioned naphthalene dicarboxylic acids or ester-forming derivatives of these, dicarboxylic acids exemplified above such as 1,3-naphthalene dicarboxylic acid, 1,4-naphthalene dicarboxylic acid, 1,5-naphthalene dicarboxylic acid, 2,6-naphthalene dicarboxylic acid and 2,7-naphthalene dicarboxylic acid or ester-forming derivatives of these are preferable.

The aforementioned polyester, in which the main glycol component is an alkylene glycol, is a polyester containing alkylene glycols in total preferably in an amount of 70 mole % or more based on the total of the glycol components, more preferably in an amount of 80 mole % or more and further preferably in an amount of 90 mole % or more. Note that the alkylene glycols herein may contain a substituent and an alicyclic structure in the molecular chain.

A copolymerization component other than the aforementioned terephthalic acid/ethylene glycol, in view of attaining transparency and moldability at the same time, is preferably at least one selected from the group consisting of isophthalic acid, 2,6-naphthalene dicarboxylic acid, diethylene glycol, neopentyl glycol, 1,4-cyclohexanedimethanol, 1,2-propanediol, 1,3-propanediol and 2-methyl-1,3-propanediol, and more preferably at least one selected from the group consisting of isophthalic acid, diethylene glycol, neopentyl glycol and 1,4-cyclohexane dimethanol.

A preferable example of the polyester to be used in layer B of the oxygen-absorbing multilayer body of the embodiment is a polyester having a main repeat unit constituted of ethylene terephthalate, more preferably a linear polyester containing an ethylene terephthalate unit in an amount of 70 mole % or more, further preferably a linear polyester containing an ethylene terephthalate unit in an amount of 80 mole % or more and particularly preferably a linear polyester containing an ethylene terephthalate unit in an amount of 90 mole % or more.

Another preferable example of the polyester to be used in layer B of the oxygen-absorbing multilayer body of the embodiment is a polyester having a main repeat unit constituted of ethylene-2,6-naphthalate, more preferably a linear polyester containing ethylene-2,6-naphthalate unit in an amount of 70 mole % or more, further preferably a linear polyester containing ethylene-2,6-naphthalate unit in an amount of 80 mole % or more and particularly preferably a linear polyester containing ethylene-2,6-naphthalate unit in an amount of 90 mole % or more.

Another preferable example of the polyester to be used in layer B of the oxygen-absorbing multilayer body of the embodiment is a linear polyester containing a propylene terephthalate unit in an amount of 70 mole % or more, a linear polyester containing a propylene naphthalate unit in an amount of 70 mole % or more, a linear polyester containing a 1,4-cyclohexanedimethylene terephthalate unit in an amount of 70 mole % or more, a linear polyester containing a butylene naphthalate unit in an amount of 70 mole % or more or a linear polyester containing a butylene terephthalate unit in an amount of 70 mole % or more.

In view of attaining transparency and moldability at the same time, a particularly preferable polyester, in other words, a particularly preferable combination of components constituting a total polyester, includes a combination of terephthalic acid/isophthalic acid/ethylene glycol, a combination of terephthalic acid/ethylene glycol/1,4-cyclohexane dimethanol and a combination of terephthalic acid/ethylene glycol/neopentyl glycol. Note that, needless to say, the polyesters mentioned above may inevitably contain diethylene glycol, which is produced by dimerization of ethylene glycols during an esterification (transesterification) reaction and a polycondensation reaction, in a small amount (5 mole % or less).

Another preferable example of the polyester to be used in layer B of the oxygen-absorbing multilayer body of the embodiment is poly(glycolic acid), which is obtained through polycondensation of a glycolic acid and methyl glycolate or ring-opening polycondensation of glycolide.

Note that the poly(glycolic acid) may be copolymerized with another component such as lactide.

<Polyamide>

Specific examples of the polyamide to be used in layer B of the oxygen-absorbing multilayer body of the embodiment include polyamides containing a unit derived from a lactam or an aminocarboxylic acid as a main constituent unit; aliphatic polyamides containing a unit derived from an aliphatic diamine and an aliphatic dicarboxylic acid as a main constituent unit; partially aromatic polyamides containing a unit derived from an aliphatic diamine and an aromatic dicarboxylic acid as a main constituent unit; and partially aromatic polyamides containing a unit derived from an aromatic diamine and an aliphatic dicarboxylic acid as a main constituent unit. Note that the polyamides herein may be, if necessary, copolymerized with a monomer unit other than a main constituent unit.

Specific examples of the lactam or aminocarboxylic acid include lactams such as ε-caprolactam and laurolactam; aminocarboxylic acids such as aminocaproic acid and aminoundecanoic acid; and aromatic aminocarboxylic acids such as para-aminomethylbenzoic acid.

Specific examples of the aliphatic diamine include aliphatic diamines having 2 to 12 carbon atoms or functional derivatives thereof and alicyclic diamines. Note that the aliphatic diamines may be linear aliphatic diamines or branched aliphatic diamines. Specific examples of the linear aliphatic diamines include aliphatic diamines such as ethylenediamine, 1-methylethylenediamine, 1,3-propylenediamine, tetramethylenediamine, pentamethylenediamine, hexamethylenediamine, heptamethylenediamine, octamethylenediamine, nonamethylenediamine, dacamethylenediamine, undecamethylenediamine and dodecamethylenediamine. Specific examples of the alicyclic diamines include cyclohexanediamine, 1,3-bis(aminomethyl)cyclohexane and 1,4-bis(aminomethyl)cyclohexane.

Specific examples of the aliphatic dicarboxylic acid include linear aliphatic dicarboxylic acids and alicyclic dicarboxylic acids. In particular, linear aliphatic dicarboxylic acids having an alkylene group of 4 to 12 carbon atoms are preferable. Examples of the linear aliphatic dicarboxylic acids include adipic acid, sebacic acid, malonic acid, succinic acid, glutaric acid, pimelic acid, suberic acid, azelaic acid, undecanoic acid, undecadioic acid, dodecanedioic acid, dimeric acid and functional derivatives of these. Examples of the alicyclic dicarboxylic acids include 1,4-cyclohexane dicarboxylic acid, hexahydroterephthalic acid and hexahydroisophthalic acid.

Specific examples of the aromatic diamines include metaxylylenediamine, paraxylylenediamine and para-bis(2-aminoethyl)benzene.

Specific examples of the aromatic dicarboxylic acids include terephthalic acid, isophthalic acid, phthalic acid, 2,6-naphthalene dicarboxylic acid, diphenyl-4,4'-dicarboxylic acid, diphenoxyethane dicarboxylic acid and functional derivatives thereof.

Specific examples of the polyamide include polyamide 4, polyamide 6, polyamide 10, polyamide 11, polyamide 12, polyamide 4,6, polyamide 6,6, polyamide 6,10, polyamide 6T, polyamide 9T, polyamide 6IT, poly(metaxylylene adipamide) (polyamide MXD6), isophthalic acid copolymerized poly(metaxylylene adipamide) (polyamide MXD6I), poly(metaxylylene sebacamide) (polyamide MXD10), poly(metaxylylene dodecanamide) (polyamide MXD12), poly(1,3-bisaminocyclohexane adipamide) (polyamide BAC6) and poly(paraxylylene sebacamide) (polyamide PXD10). As more preferable polyamide, polyamide 6, polyamide MXD6 and polyamide MXD6I are mentioned.

As a component to be copolymerized with the polyamide, a polyether having at least one terminal amino group or terminal carboxyl group, and having a number average molecular weight of 2000 to 20000, an organic carboxylic acid salt of a polyether having at least one terminal amino group or an amino salt of a polyether having at least one terminal carboxyl group, can be used. Specific examples thereof include bis(aminopropyl)poly(ethylene oxide) (polyethylene glycol having a number average molecular weight of 2000 to 20000).

The partially aromatic polyamides may contain a constituent unit derived from a polyvalent carboxylic acid having 3 bases or more, such as trimellitic acid and pyromellitic acid, as long as they maintain a substantially linear chain.

<Ethylene-Vinyl Alcohol Copolymer>

As the ethylene vinyl alcohol copolymer to be used in layer B of the oxygen-absorbing multilayer body of the embodiment, an ethylene vinyl alcohol copolymer, which contains an ethylene in an amount of 15 to 60 mole % and has a saponification degree of a vinyl acetate component of 90 mole % or more, is preferable. The content of ethylene is preferably 20 to 55 mole % and more preferably 29 to 44 mole %. The saponification degree of the vinyl acetate component is preferably 95 mole % or more. Note that the ethylene vinyl alcohol copolymer may further contain a small amount of comonomer of propylene, isobutene, an α-olefin such as α-octene, α-dodecene and α-octadecene, an unsaturated carboxylic acid or a salt thereof, a partial alkyl ester, a complete alkyl ester, a nitrile, an amide or an anhydride, or an unsaturated sulfonic acid or a salt thereof, etc.

<Vegetable-Derived Resin>

As the vegetable-derived resin to be used in layer B of the oxygen-absorbing multilayer body of the embodiment, any vegetable-derived resin can be used as long as it is a resin containing a vegetable-derived substance as a raw material. The vegetable serving as a raw material thereof is not particularly limited. Specific examples of the vegetable-derived resin include aliphatic polyester based biodegradable resins. Furthermore, examples of the aliphatic polyester based biodegradable resins include poly(α-hydroxy acid) such as poly(glycolic acid) (PGA) and polylactic acid (PLA); and polyalkylene alkanoate such as polybutylenesuccinate (PBS) and polyethylenesuccinate (PES).

<Chlorine Resin>

The chlorine resin to be used in layer B of the oxygen-absorbing multilayer body of the embodiment is not limited as long as it is a resin containing chlorine in a constituent unit and a known resin can be used. Specific examples of the chlorine resin include poly(vinyl chloride), poly(vinylidene chloride) and copolymers of these with vinyl acetate, a maleic acid derivative or a higher alkyl vinyl ether, etc.

Layer B of the oxygen-absorbing multilayer body of the embodiment may contain various types of additives known in the art other than a thermoplastic resin as mentioned above. Examples of such optional components include, but not particularly limited to, additives such as a drying agent, a pigment such as titanium oxide, a dye, an antioxidant, a slipping agent, an antistatic agent, a plasticizer, a stabilizer, a lubricant; fillers such as calcium carbonate, clay, mica and silica; and a deodorant. Particularly, in view of recycling and reprocessing offcuts generated during manufacturing, it is preferable to add an antioxidant to layer B.

[Other Layers]

The oxygen-absorbing multilayer body of the embodiment may have an optional layer, which varies depending upon the desired performance etc., other than the oxygen-absorbing layer (layer A) and the resin layer (layer B) mentioned above. Examples of such an optional layer include an adhesion layer, a metal foil, a metal vapor deposition layer and an organic-inorganic film.

For example, in view of more enhancing interlayer adhesion strength between adjacent two layers, an adhesion layer (layer AD) is preferably provided between the two layers. The adhesion layer preferably contains a thermoplastic resin having adhesiveness. Examples of the thermoplastic resin having adhesiveness include acid modified polyolefin resins obtained by modifying a polyolefin resin such as a polyethylene or a polypropylene with an unsaturated carboxylic acid such as acrylic acid, methacrylic acid, maleic acid, maleic anhydride, fumaric acid and itaconic acid; and polyester thermoplastic elastomers containing a polyester block copolymer as a main component. In view of enhancing adhesiveness with the aforementioned resin layer (layer B), a resin obtained by modifying the same type of resin as a thermoplastic resin used in layer B is preferable. Note that the thickness of the adhesion layer is not particularly limited; however, in view of ensuring molding processability while exerting substantial adhesion strength, the thickness of the adhesion layer is preferably 2 to 100 µm, more preferably 5 to 90 µm and further preferably 10 to 80 µm.

In view of more enhancing gas barrier property and light-blocking property, it is preferable to provide a metal foil, a metal vapor deposition layer, an organic-inorganic film or the like to one of the surfaces of layer A or layer B mentioned above. The metal foil herein is not particularly limited; however, an aluminum foil is preferable. The thickness of the metal foil is preferably 3 to 50 µm, more preferably 3 to 30 µm and further preferably 5 to 15 µm, in view of gas barrier property, light-blocking property, flex resistance, etc. The metal vapor deposition layer is not particularly limited; however, a resin film etc., on which a film of a metal or a metal oxide such as aluminum or alumina is formed by vapor-deposition, is preferable. Note that examples of a method for forming a vapor deposition film include physical vapor deposition methods such as a vacuum vapor deposition method, a sputtering method and an ion plating method and chemical vapor deposition methods such as PECVD, but not particularly limited to these and known methods are applicable. The thickness of the vapor deposition film is preferably 5 to 500 nm and more preferably 5 to 200 nm, in view of gas barrier property, light-blocking property, flex resistance, etc. Although the organic-inorganic film layer is not particularly limited, a resin film having a coating film such as a silica-polyvinyl alcohol hybrid film formed by a sol-gel method etc. is preferable. The thickness of the coating film is preferably 100 nm to 50 µm and more preferably 1 to 15 µm in view of gas barrier property, light-blocking property, flex resistance, etc.

The oxygen-absorbing multilayer body of the embodiment may have an easy-to-peel layer and an easy-to-tear layer in order to easily open an oxygen-absorbing multilayer container. As the easy-to-peel layer, for example, a film formed by blending two types or more of polyolefins to control sealing strength and peeling strength is generally known. As the easy-to-tear layer, for example, an easy-to-tear film formed by blending nylon MXD6 with nylon 6 is generally known.

The oxygen-absorbing multilayer body of the embodiment can be manufactured by using a known method such as a coextrusion method, a laminating method and a coating method, which varies depending upon e.g., the properties of the material, processing purpose and processing step. The manufacturing method is not particularly limited. For molding e.g., a film or a sheet, a manufacturing method of extruding a molten resin composition from an extruder provided with a T die, a circular die, etc., and a manufacturing method of applying an adhesive to an oxygen-absorbing film or sheet separately formed and attaching it to another film or sheet are known. If necessary, a pretreatment such as a corona treatment and an ozone treatment can be applied to a film etc. Furthermore, a known anchor coating agent, an adhesive, etc. can also be used. Examples of the anchor coating agent include isocyanate (urethane), polyethylene imine, polybutadiene and organic titanium. Examples of the adhesive include polyurethane, polyacrylate, polyester, epoxy, poly(vinyl acetate), cellulose and other adhesives for lamination.

[Oxygen-Absorbing Multilayer Container]

The oxygen-absorbing multilayer container of the embodiment has an oxygen-absorbing multilayer body as mentioned above in the packaging container in whole or in part. The oxygen-absorbing multilayer container of the embodiment can absorb oxygen within the container (even if the amount of oxygen transmitting or coming into the container from the outside through the wall of the container is small, transmitting or incoming oxygen is also absorbed) to prevent deterioration etc. of the content (article to be packaged) stored therein by oxygen.

The shape of the oxygen-absorbing multilayer container of the embodiment is not particularly limited and can be appropriately specified depending upon the article to be contained and stored. For example, a film-form or sheet-form oxygen-absorbing multilayer body as mentioned above can be formed into a bag such as a three-side sealed flat bag, a standing pouch, a gusset packaging bag, a pillow packaging bag, a multi-chamber pouch, which contains a main chamber and a sub chamber having an easy-to-peel wall between the main chamber and the sub chamber, and a shrink film package; and can be also formed into a container having an arbitrary shape by thermoforming.

More specifically, if a film-form or sheet-form oxygen-absorbing multilayer body as mentioned above is subjected to a molding such as vacuum molding, air-pressure forming and plug assist molding, oxygen-absorbing multilayer containers having a predetermined shape such as a tray, a cup, a bottle, a tube and PTP (press-through pack) can be manufactured. Also, if molten resins are simultaneously injected or sequentially injected through multi-layered multiple dies into an injection mold by use of an injector, a multilayer container having a predetermined shape can be formed at a time.

Note that when a container having a flange portion is manufactured by thermoforming, a special process for imparting an easy-peeling function may be applied to the flange portion. If an oxygen-absorbing multilayer body as mentioned above is used as a material for a cover of a container, top seal, etc., oxygen-absorbing function can be imparted to these containers.

(Third Embodiment)

Now, the third embodiment of the present invention will be described below. Note that repetition of explanation with respect to the same content as in the first and second embodiments is avoided herein.

[Oxygen-Absorbing Multilayer Body]

The oxygen-absorbing multilayer body of the embodiment is obtained by laminating at least three layers, i.e., a sealant layer (layer C) containing a thermoplastic resin, an oxygen-absorbing layer (layer A) formed of an oxygen-absorbing resin composition containing a tetralin ring-containing polyester compound and a transition metal catalyst, and a gas barrier layer (layer D) containing a gas barrier substance, in this order. Similarly to the first and second embodiments, the oxygen-absorbing multilayer body of the embodiment may have a layer other than these three layers in any position, if necessary.

By using the oxygen-absorbing multilayer body of the embodiment in part or in whole of a packaging container for sealing such that layer C faces inside, oxygen within the container can be absorbed (even if the amount of oxygen transmitting or coming into the container from the outside through the wall of the container is small, transmitting or incoming oxygen is also absorbed) to prevent deterioration etc. of the content (article to be packaged) stored therein by oxygen.

[Sealant Layer (Layer C)]

The sealant layer (layer C) of the oxygen-absorbing multilayer body of the embodiment contains a thermoplastic resin. Layer C has, in addition to a role as a sealant, a role in transmitting oxygen in the container up to an oxygen-absorbing layer; at the same time, isolating the content (article to be packaged) from the oxygen-absorbing layer (layer A) (inhibiting physical contact between layer A and the article to be packaged). The oxygen transmission rate of layer C measured in the case of a film having a thickness of 20 μm at 23° C. under the conditions of a relative humidity of 60% is preferably 300 mL/(m²·day·atm) or more, more preferably 400 mL/(m²·day·atm) or more and further preferably 500 mL/(m²·day·atm) or more. If the oxygen transmission rate satisfies the aforementioned preferable values or more, the oxygen-absorbing rate of layer A can be more enhanced, compared to the case where the oxygen transmission rate does not satisfy the above values.

Examples of the thermoplastic resin to be used in layer C of the oxygen-absorbing multilayer body of the embodiment include polyethylenes such as a high-density polyethylene, a medium-density polyethylene, a low-density polyethylene, linear and low-density polyethylene, a linear and extremely low-density polyethylene and a polyethylene obtained in the presence of a metallocene catalyst; polystyrenes; polymethylpentenes; polypropylenes such as a propylene homo polymer, a propylene-ethylene block copolymer and a propylene-ethylene random copolymer; polyesters having a heat sealing property such as PET, A-PET, PETG and PBT; and amorphous nylon. These can be used alone or in a combination. To these thermoplastic resins, if necessary, an ethylene-vinyl acetate copolymer, an ethylene-methyl acrylate copolymer, an ethylene-ethyl acrylate copolymer, an ethylene-acrylate copolymer, an ethylene-methacrylate copolymer, an ethylene-methyl methacrylate copolymer and a thermoplastic elastomer may be added. The thermoplastic resin to be preferably used in layer C of the oxygen-absorbing multilayer body of the embodiment has an MFR at 200° C. of 1 to 35 g/10 minutes or an MFR at 240° C. of 2 to 45 g/10 minutes, in consideration of moldability and processability of a multilayer body.

Furthermore, layer C of the oxygen-absorbing multilayer body of the embodiment may contain additives known in the art other than a thermoplastic resin as mentioned above. Examples of such optional components include, but not particularly limited to, additives such as a drying agent, a pigment such as titanium oxide, a dye, an antioxidant, a slipping agent, an antistatic agent, a plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant to layer C.

The content rate of the thermoplastic resin in layer C, which can be appropriately specified, is not particularly limited; however the content rate is preferably 70 to 100 mass % based on the total amount of layer C, more preferably 80 to 100 mass % and further preferably 90 to 100 mass %. The thermoplastic resin to be used in layer C of the embodiment preferably contains a thermoplastic resin other than a tetralin ring-containing polyester compound as described in the first embodiment, in an amount of 50 to 100 mass % based on the total amount of layer C, more preferably 70 to 100 mass % and further preferably 90 to 100 mass %.

[Oxygen-Absorbing Layer (Layer A)]

The oxygen-absorbing layer (layer A) of the oxygen-absorbing multilayer body of the embodiment is formed of an oxygen-absorbing resin composition containing at least one tetralin ring-containing polyester compound having at least one selected from the group consisting of the constituent units represented by the above general formulas (1) to (4) and a transition metal catalyst. The oxygen-absorbing resin composition used herein is the same as described in the first embodiment.

The content rate of the tetralin ring-containing polyester compound in layer A, which is not particularly limited, is preferably 50 mass % or more based on the total amount of layer A, more preferably 70 mass % or more and further preferably 90 mass % or more. If the content rate of a tetralin ring-containing polyester compound is the preferable value or more, the oxygen-absorbing performance can be more enhanced, compared to the case where the content rate does not satisfy the above value.

In the oxygen-absorbing multilayer body of the embodiment, the thickness of the oxygen-absorbing layer (layer A), which can be appropriately specified depending upon use and desired performance, is not particularly limited. The thickness is preferably 5 to 200 μm and more preferably 10 to 100 μm. If the thickness falls within the preferable range mentioned above, the performance of layer A to absorb oxygen can be more enhanced; at the same time, the processability and economic aspect can be maintained at high levels, compared to the case where the thickness does not fall the above range. The thickness of the sealant layer (layer C), which can be also appropriately specified depending upon use and desired performance, is not particularly limited. The thickness is preferably 5 to 200 μm and more preferably 10 to 80 μm. If thickness falls within the preferable range mentioned above, the oxygen-absorbing rate of layer A can be more enhanced; at the same time, the processability and economic aspect can be maintained at high levels, compared to the case where the thickness does not fall within the above range. In consideration of processability of the resultant oxygen-absorbing multilayer body, the thickness ratio of layer C and layer A is preferably 1:0.5 to 1:3 and more preferably 1:1.5 to 1:2.5.

[Gas Barrier Layer (Layer D)]

The gas barrier layer (layer D) of the oxygen-absorbing multilayer body of the embodiment contains a gas barrier substance. The oxygen transmission rate of layer D measured in the case of a film having a thickness of 20 μm at 23° C. under the conditions of a relative humidity of 60% is preferably 100 mL/(m²·day·atm) or less, more preferably 80 mL/(m²·day·atm) or less and further preferably 50 mL/(m²·day·atm) or less.

As the gas barrier substance to be used in layer D of the oxygen-absorbing multilayer body of the embodiment, a gas barrier thermoplastic resin, a gas barrier thermosetting resin, a silica, alumina, aluminum, etc. (used in the form of a vapor deposition film) and a metal such as aluminum (used in the form of foil) can be used. Examples of the gas barrier thermoplastic resin include an ethylene-vinyl alcohol copolymer, MXD6 and a poly(vinylidene chloride). Examples of the gas barrier thermosetting resin include gas barrier epoxy resin such as "MAXIVE" manufactured by Mitsubishi Gas Chemical Company, Inc.

When a thermoplastic resin is used as a gas barrier substance, the thickness of the gas barrier layer (layer D) is preferably 5 to 200 µm and more preferably 10 to 100 µm. When a thermosetting resin such as an amine-epoxy hardening agent is used as a gas barrier substance or in a gas barrier adhesive layer, the thickness of layer D is preferably 0.1 to 100 µm and more preferably 0.5 to 20 µm. If the thickness falls within the preferable range mentioned above, the gas barrier property tends to be more enhanced; at the same time, the processability and economic aspect can be maintained at high levels, compared to the case where the thickness does not fall within the aforementioned range.

Note that the oxygen-absorbing multilayer body of the embodiment may have one or more other layers such as a resin layer, a metal foil layer or an adhesive layer between layer C and layer A, between layer A and layer D or as an outer layer of layer C or as an outer layer of layer D. For example, to prevent breakage of layer D and formation of a pin hole, a protecting layer formed of a thermoplastic resin can be provided inside or outside layer D. Examples of the resin to be used in the protecting layer include polyethylenes such as a high-density polyethylene; polypropylenes such as a propylene homo polymer, a propylene-ethylene random copolymer and a propylene-ethylene block copolymer; polyamides such as nylon 6 and nylon 6,6; polyesters such as PET; and combinations of these.

In consideration of processability, the oxygen-absorbing multilayer body of the embodiment preferably has an intermediate layer formed of a polyolefin resin interposed between layer D and layer A. The thickness of the intermediate layer is preferably substantially the same as the thickness of layer C in view of processability. Note that herein, in consideration of variation by processing, if a thickness ratio of the layers falls within ±10%, the thicknesses of the layers are regarded as being substantially same.

The oxygen-absorbing multilayer body of the embodiment can be manufactured by using a known method such as a coextrusion method, a laminating method and a coating method, which varies depending upon e.g., the properties of the material, processing purpose and processing step. The manufacturing method is not particularly limited. For example, a general method for laminating packaging materials such as a wet lamination process, a dry lamination process, a dry lamination process in the absence of a solvent, an extrusion lamination process, a T die coextrusion molding method, a coextrusion lamination process and an inflation process can be applied. For example, for molding a film or a sheet, a method of extruding a molten resin composition from an extruder provided with a T die, a circular die, etc., and a method of applying an adhesive to an oxygen-absorbing film or sheet separately formed and attaching it to another film or sheet are known. If necessary, for example, a pretreatment such as a corona treatment and an ozone treatment can be applied to a film etc. Furthermore, a known anchor coating agent, an adhesive, etc. can also be used. Examples of the anchor coating agent include isocyanate (urethane), polyethylene imine, polybutadiene and organic titanium. Examples of the adhesive include polyurethane, polyacrylate, polyester, epoxy, poly(vinyl acetate), cellulose and other adhesives for lamination.

Usage of the oxygen-absorbing multilayer body of the embodiment and the shape thereof are not particularly limited and can be appropriately specified depending upon the article to be contained and stored. For example, the multilayer body is manufactured as a film, which is further processed into a bag-form and a cover material and then put in use. Alternatively, a paper base material is laminated as an outer layer of layer D and the resultant laminate can be used as an oxygen-absorbing paper base material or as an oxygen-absorbing paper container. In view of maintaining processability in manufacturing a paper container by laminating with a paper base material at a high level, the total thickness of the layers present inside layer D is preferably 100 µm or less and more preferably 80 µm or less.

[Oxygen-Absorbing Multilayer Container]

The oxygen-absorbing multilayer container of the embodiment has an oxygen-absorbing multilayer body as mentioned above in whole or in part thereof.

Usage of the oxygen-absorbing multilayer container of the embodiment and the shape thereof are not particularly limited and can be appropriately specified depending upon the article to be contained and stored. For example, a film-form or sheet-form oxygen-absorbing multilayer body as mentioned above is subjected to molding such as vacuum molding, air-pressure forming and plug assist molding, if necessary, while applying heat to manufacture an oxygen-absorbing multilayer container having a predetermined shape such as a tray, a cup, a bottle, a tube and PTP (press-through pack). Furthermore, if thermoforming is applied, a container of any shape can be manufactured. Alternatively, if molten resins are simultaneously injected or sequentially injected through multi-layered multiple dies into an injection mold by use of an injector, a multilayer container having a predetermined shape can be formed at a time. Moreover, the oxygen-absorbing multilayer body and container of the embodiment, if an open hole for releasing vapor during microwave cooking is provided, can be preferably used as a pouch for microwave cooking provided with a hole for easily releasing water vapor during microwave cooking.

(Fourth Embodiment)

Now, the fourth embodiment of the present invention will be described below. Note that repetition of explanation with respect to the same content as in the first to third embodiments is avoided herein.

[Oxygen-Absorbing Multilayer Body]

The oxygen-absorbing multilayer body of the embodiment is obtained by laminating at least three layers, i.e., a sealant layer (layer C) containing a thermoplastic resin, an oxygen-absorbing layer (layer A) formed of an oxygen-absorbing resin composition containing a tetralin ring-containing polyester compound, a transition metal catalyst and a polyolefin resin, and a gas barrier layer (layer D) containing a gas barrier substance, in this order. Similarly to the first to third embodiments, the oxygen-absorbing multilayer body of the embodiment may have a layer other than these three layers in any position, if necessary.

By using the oxygen-absorbing multilayer body of the embodiment in part or in whole of an packaging container for sealing such that layer C faces inside, oxygen within the container can be absorbed (even if the amount of oxygen transmitting or coming into the container from the outside through the wall of the container is small, transmitting or incoming oxygen is also absorbed) to prevent deterioration etc. of the content (article to be packaged) stored therein by oxygen.

[Sealant Layer (Layer C)]

The sealant layer (layer C) of the oxygen-absorbing multilayer body of the embodiment contains a thermoplastic resin. The sealant layer (layer C) of the oxygen-absorbing multilayer body of the embodiment and the thermoplastic resin are the same as described in the third embodiment.

[Oxygen-Absorbing Layer (Layer A)]

The oxygen-absorbing layer (layer A) of the oxygen-absorbing multilayer body of the embodiment is formed of an oxygen-absorbing resin composition containing at least one tetralin ring-containing polyester compound selected from the group consisting of the constituent units represented by the above general formulas (1) to (4), a transition metal catalyst and a polyolefin resin. The oxygen-absorbing resin composition used herein is the same as that described in the first embodiment. Furthermore, the oxygen-absorbing layer (layer A) is the same as that described in the third embodiment except the matters specifically described below.

In the oxygen-absorbing layer (layer A) of the oxygen-absorbing multilayer body of the embodiment, the content rate of the tetralin ring-containing polyester compound is preferably 10 to 90 parts by mass based on the total (100 parts by mass) of the tetralin ring-containing polyester compound and the polyolefin resin, more preferably 20 to 80 parts by mass and further preferably 30 to 70 parts by mass. If the content rate of the tetralin ring-containing polyester compound falls within the preferable range, the oxygen-absorbing performance can be more enhanced, compared to the case where the content rate does not fall within the above range. In addition, high moldability can be maintained.

[Gas Barrier Layer (Layer D)]

The gas barrier layer (layer D) of the oxygen-absorbing multilayer body of the embodiment contains a gas barrier substance. The gas barrier layer (layer D) and gas barrier substance are the same as described in the third embodiment.

Note that the oxygen-absorbing multilayer body of the embodiment may have one or more other layers such as a resin layer, a metal foil layer or an adhesive layer between layer C and layer A, between layer A and layer D or as an outer layer of layer C or as an outer layer of layer D. These optional layers are the same as described in the third embodiment.

The method for manufacturing an oxygen-absorbing multilayer body of the embodiment is the same as that described in the third embodiment.

[Oxygen-Absorbing Multilayer Container]

The oxygen-absorbing multilayer container of the embodiment has the aforementioned oxygen-absorbing multilayer body in whole or in part thereof.

Usage of the oxygen-absorbing multilayer body of the embodiment and the shape thereof are not particularly limited and can be appropriately specified depending upon the article to be contained and stored. Details of these are the same as described in the third embodiment.

(Fifth Embodiment)

The fifth embodiment of the present invention will be described below. Note that repetition of explanation with respect to the same content as in the first to fourth embodiments is avoided herein.

[Oxygen-Absorbing Paper Container and Oxygen-Absorbing Multilayer Body]

The oxygen-absorbing paper container of the embodiment is a paper container obtained by forming an oxygen-absorbing multilayer body into a carton. To describe more specifically, the oxygen-absorbing multilayer body constituting a paper container is obtained by laminating at least four layers, i.e., an isolation layer (layer F) containing a thermoplastic resin, an oxygen-absorbing layer (layer A) formed of a polyester compound and a transition metal catalyst, a gas barrier layer (layer D) containing a gas barrier substance and a paper substrate layer (layer E), in this order. Similarly to the first to fourth embodiments, the oxygen-absorbing multilayer body of the embodiment may have, if necessary, a layer other than these four layers at any position.

By use of the oxygen-absorbing multilayer body in part or in whole of an packaging container for sealing such that layer F faces inside, the oxygen-absorbing paper container of the embodiment can absorb oxygen within the container (even if the amount of oxygen transmitting or coming into the container from the outside through the wall of the container is small, transmitting or incoming oxygen is also absorbed) to prevent deterioration etc. of the content (article to be packaged) stored therein by oxygen.

[Isolation Layer Containing a Thermoplastic Resin (Layer F)]

In the embodiment, the isolation layer (layer F) of the oxygen-absorbing multilayer body contains a thermoplastic resin. Layer F has a role in transmitting oxygen in the container up to an oxygen-absorbing layer (layer A); at the same time, isolating the content (article to be packaged) from the oxygen-absorbing layer (layer A) (inhibiting physical contact between layer A and an article to be packaged). Furthermore, when the container is formed by molding the oxygen-absorbing multilayer body into a carton, layer F can serve as a sealant for sealing the paper container by mutually fusing by application of heat.

As a thermoplastic resin having the thermal adhesiveness which can be used in layer F, thermoplastic resins such as polyolefin resins capable of melting by heat and mutually adhere are exemplified. Specific examples thereof include acid modified polyolefin resins obtained by modifying a polyolefin resin such as a low-density polyethylene, a medium-density polyethylene, a high-density polyethylene, straight (linear) low-density polyethylene, an ethylene-α-olefin copolymer obtained by polymerization in the presence of a metallocene catalyst, polypropylene, an ethylene-vinyl acetate copolymer, an ionomer resin, an ethylene-acrylic acid copolymer, an ethylene-ethyl acrylate copolymer, an ethylene-methacrylate copolymer, an ethylene-propylene copolymer, a methylpentene polymer, a polybutene polymer, a poly(vinyl acetate) resin, a poly(meth)acrylate resin, a poly(vinyl chloride) resin, a polyethylene or a polypropylene with an unsaturated carboxylic acid such as acrylic acid, methacrylic acid, maleic acid, maleic anhydride, fumaric acid or itaconic acid. These can be used alone or in combination with two or more. Of them, in view of molding processability, sanitation, odor, etc., a low-density polyethylene, a medium-density polyethylene, a high-density polyethylene, a straight (linear) low-density polyethylene and an ethylene-α-olefin copolymer obtained by polymerization in the presence of a metallocene catalyst are preferable.

The content rate of the thermoplastic resin in layer F, which can be appropriately specified, is not particularly limited. The content rate is preferably 70 to 100 mass % based on the total amount of layer F, more preferably 80 to 100 mass % and further preferably 90 to 100 mass %. The thermoplastic resin to be used in layer F of the embodiment preferably contains a thermoplastic resin other than a tetralin ring-containing polyester compound as described in the first embodiment in an amount of 50 to 100 mass % based on the total amount of layer F, more preferably 70 to 100 mass % and further preferably 90 to 100 mass %.

Layer F may contain additives known in the art other than the thermoplastic resins as mentioned above. Examples of such optional components include, but not particularly limited to, additives such as a drying agent, a pigment such as titanium oxide, a dye, an antioxidant, a slipping agent, an antistatic agent, plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant to layer F.

Furthermore, in the oxygen-absorbing multilayer body of the embodiment, the thickness of the isolation layer (layer F), which can be appropriately specified depending upon the use and desired performance, is not particularly limited. The thickness is preferably 5 to 50 μm and more preferably 10 to 40 μm. If the thickness falls within the preferable range mentioned above, the rate of absorbing oxygen by the oxygen-absorbing layer can be more enhanced; at the same time, the processability and economic aspect can be maintained at high levels, compared to the case where the thickness does not fall the above range.

[Oxygen-Absorbing Layer (Layer A)]

In the embodiment, the oxygen-absorbing layer (layer A) of the oxygen-absorbing multilayer body is formed of an oxygen-absorbing resin composition containing at least one tetralin ring-containing polyester compound selected from the group consisting of the constituent units represented by the above general formulas (1) to (4) and a transition metal catalyst. The oxygen-absorbing resin composition used herein is the same as that described in the first embodiment. Furthermore, the oxygen-absorbing layer (layer A) is the same as that described in the third embodiment except the matters specifically described below.

In the oxygen-absorbing multilayer body of the embodiment, the thickness of the oxygen-absorbing layer (layer A), which can be appropriately specified depending upon use and desired performance, is not particularly limited. The thickness is preferably 5 to 50 μm and more preferably 10 to 40 μm. If the thickness falls within the preferable range mentioned above, the performance of the oxygen-absorbing layer to absorb oxygen can be more enhanced; at the same time, the processability and economic aspect can be maintained at high levels, compared to the case where the thickness does not fall the above range.

[Gas Barrier Layer (Layer D)]

In the embodiment, the gas barrier layer (layer D) of the oxygen-absorbing multilayer body contains a gas barrier substance. The gas barrier substance and the gas barrier layer (layer D) used herein are the same as described in the third embodiment.

[Paper Substrate Layer (Layer E)]

In the embodiment, the paper substrate layer (layer E), since it serves as a base material constituting a container, is preferably excellent in shaping property, flex resistance, rigidity, elasticity, strength, etc. As the paper base material constituting layer E, various types of paper base materials such as bleached or unbleached paper base material extremely stable in size, snow-white roll, craft paper, cardboard, processed paper and others can be used. The basis weight of layer E, which can be appropriately specified, is not particularly limited. The basis weight preferably falls within the range of about 80 to 600 g/m² and more preferably within the range of 100 to 450 g/m². Note that, in the embodiment, on the paper substrate layer, for example, letters, figures, pictures, symbols and other desired pictures may be optionally printed by a conventional printing system.

Note that the oxygen-absorbing multilayer body of the embodiment may have one or more other layers such as a resin layer, a metal foil layer or an adhesive layer between layer F and layer A, between layer A and layer D, between layer D and layer E or as an outer layer of layer F or as an outer layer of layer E. The details of these optional layers are the same as described in the third embodiment.

As the outer layer of the paper substrate layer (layer E), if necessary, an outer layer formed of a thermoplastic resin may be provided. When such a thermoplastic resin outer layer is provided, if the same thermoplastic resin as used in the aforementioned isolation layer (layer F) is used, layer F and the thermoplastic resin outer layer can be heat-sealed airtight.

In consideration of processability, an intermediate layer formed of a polyolefin resin can be interposed between layer A and layer D. It is preferable that the thickness of the intermediate layer is substantially the same as the thickness of layer F, in view of processability. Note that herein, in consideration of variation by processing, if a thickness ratio of the layers falls within ±10%, the thicknesses of the layers are regarded as being substantially same.

The method for manufacturing the oxygen-absorbing multilayer body of the embodiment is the same as described in the third embodiment.

[Oxygen-Absorbing Paper Container]

The oxygen-absorbing paper container of the embodiment employs the aforementioned oxygen-absorbing multilayer body in part or in whole of the structure. Note that a paper container fully formed of an oxygen-absorbing multilayer body refers to a paper container formed only of the oxygen-absorbing multilayer body. A paper container partly formed of an oxygen-absorbing multilayer body refers to a paper container, which has a part formed of the oxygen-absorbing multilayer body and the other part formed of another material. Examples of the latter container include a paper container having a part formed of a transparent material (for example, a material formed of the oxygen-absorbing multilayer body layer without using a paper base material) so as to see an article (article to be packaged) contained in the container from the outside.

Usage of the oxygen-absorbing paper container of the embodiment and the shape thereof are not particularly limited and can be appropriately specified depending upon the article to be contained and stored. The details of these are the same as described in the third embodiment. Note that the oxygen-absorbing paper container of the embodiment can be molded into various shapes such as a gable-top type, a brick type and a flat top.

In the oxygen-absorbing paper container of the embodiment, examples of the particularly preferable article to be packaged include, but not particularly limited to, beverages such as cow milk, juice, coffee, tea and alcohol beverage; liquid seasonings such as source, soy sauce, noodle broth and dressing; chemical products such as an adhesive, a gluing agent, an agrichemical and a pesticide; medicinal products; sundry articles such as cosmetic, shampoo, conditioner and detergent; and other various articles. Particularly, the oxygen-absorbing paper container of the embodiment is suitable for packaging an article to be packaged easily degrading in the presence of oxygen. Examples of such an article to be packaged include beverages such as beer, wine, Japanese sake, shochu, fruit juice beverage, fruit juice, vegetable juice, carbonate soft drink, coffee, tea, mayonnaise, ketchup, edible oil, dressing and source.

(Sixth Embodiment)

Now, the sixth embodiment of the present invention will be described below. Note that repetition of explanation with respect to the same content as in the first to fifth embodiments is avoided herein.

[Oxygen-Absorbing Injection-Molded Article]

The oxygen-absorbing injection-molded article of the embodiment is obtained by injection molding of the oxygen-absorbing resin composition of the first embodiment. By constituting an oxygen-absorbing injection-molded article from the oxygen-absorbing resin composition of the first embodiment in this way, excellent oxygen-absorbing performance can be delivered. Note that the oxygen-absorbing resin composition used herein is the same as that described in the first embodiment.

In particular, of the oxygen-absorbing resin compositions of the first embodiment, if an oxygen-absorbing resin composition at least containing a tetralin ring-containing polyester compound, a transition metal catalyst and a thermoplastic resin is used to constitute the oxygen-absorbing injection-molded article of the embodiment, excellent oxygen-absorbing performance and oxygen barrier performance can be delivered. The thermoplastic resin to be used in the preferred aspect of the embodiment is preferably at least one selected from the group containing a polyolefin, a polyester, a polyamide and a vegetable-derived resin. In view of effectively exerting an oxygen absorption effect, a resin having high oxygen barrier property, such as a polyester and a polyamide, is more preferable. Specific examples of these resins preferably used include thermoplastic resins exemplified as those preferably used in layer B of the oxygen-absorbing multilayer body of the second embodiment.

As a method for manufacturing the oxygen-absorbing injection-molded article of the embodiment, a known method, which varies depending upon the properties of materials, a desired shape, etc., can be applied. Thus, the manufacturing method is not particularly limited. An injection-molded article can be manufactured by applying various injection molding methods. For example, an oxygen-absorbing resin composition as mentioned above is injected from an injection cylinder through a mold hot runner into a mold cavity by use of a molding machine provided with an injector and an injection mold. In this manner, an injection-molded article having a shape in accordance with the cavity shape of the injection mold can be manufactured. To add heat resistance to the neck portion of the obtained molded article, a heat treatment may be applied to the neck portion in this stage to perform crystallization. In this case, the degree of crystallization, which may be appropriately specified depending upon the type of resin to be used and desired performance, is not particularly limited. Generally, the degree of crystallization is preferably about 30 to 50% and more preferably 35 to 45%. Note that the crystallization of the neck portion of a molded article may be performed after a secondary processing (described later) is applied.

The shape of the oxygen-absorbing injection-molded article of the embodiment may be appropriately specified depending upon the use and is not particularly limited. When injection molding using a mold is performed as described above, any shape can be obtained corresponding to the shape of cavity of the mold.

The thickness of the oxygen-absorbing injection-molded article of the embodiment is not particularly limited. In view of enhancing oxygen-absorbing performance; at the same time, ensuring physical properties such as flexibility, required for an injection-molded article, the thickness is preferably 3 to 5000 μm, more preferably, 5 to 4500 μm and further preferably 10 to 4000 μm.

By using the oxygen-absorbing injection-molded article of the embodiment as a part of the structure of a sealing container, oxygen within the container can be absorbed (even if the amount of oxygen transmitting or coming into the container from the outside through the wall of the container is small, transmitting or incoming oxygen is also absorbed) to prevent deterioration etc. of the content (article to be packaged) to be stored by oxygen. At this time, the injection-molded article of the embodiment itself may be molded in the shape of the container. In consideration that the oxygen-absorbing injection-molded article of the embodiment delivers oxygen-absorbing performance, the molded article is preferably a preservation container such as a cup container (injection cup) and a bottle container.

The injection-molded article of the embodiment can be molded into a container by applying a secondary processing (described later). For example, when a secondary processing is applied to form a PET bottle, the injection-molded article of the embodiment is preferably a test tube preform (parison). The container obtained by a secondary processing of the oxygen-absorbing injection-molded article of the embodiment can also absorb oxygen within the container (even if the amount of oxygen transmitting or coming into the container from the outside through the wall of the container is small, transmitting or incoming oxygen is also absorbed) to prevent deterioration etc. of the content (article to be packaged) stored therein by oxygen. Note that examples of the shape of a container after secondary processing include a bottle and a cup.

As a method for secondary processing the oxygen-absorbing injection-molded article of the embodiment, for example, blow-molding and stretch blow-molding are mentioned but not particularly limited to these and a known molding method can be applied.

For example, in the injection blow-molding, first, a preform (parison) in the form of a test tube is molded as the oxygen-absorbing injection-molded article of the embodiment. Then, the preform is heated and allowed to fit into a final-form mold with the mouth portion thereof immobilized by a jig. Thereafter, air is fed from the mouth portion to swollen the preform, with the result that the preform comes into contact with the mold. Then, the preform is cooled and solidified to mold a bottle.

For example, in the injection stretch blow-molding, first, a preform (parison) in the form of a test tube is molded as the oxygen-absorbing injection-molded article of the embodiment. Then, the preform is heated and allowed to fit into a final-form mold with the mouth portion thereof immobilized by a jig. Thereafter, air is fed from the mouth portion while stretching by a stretching rod to perform blow-drawing of the preform to allow the preform in contact with the mold. Then, the preform is cooled and solidified to mold a bottle.

The injection stretch blow-molding methods herein are in general roughly divided into a hot parison system and a cold parison system. In the former one, a preform is not completely cooled and a preform in a soft condition is blow-molded. In contrast, in the latter one, a preform (with a bottom) having a size considerably smaller than the size of a final shape and formed of an amorphous resin in a super cooling condition is formed, and the preform is pre-heated to a drawing temperature and molded in the axis direction by tensile stretching in a final-shape mold; at the same time, molded in the circumference direction by stretch blowing. Because of this, the latter one is suitable for large scale production. In either method, a preform is heated to a drawing temperature of a glass transition point (Tg) or more and thereafter stretched in the longitudinal direction by a stretching rod in a final-shape mold heated to a heat treatment (heat set) temperature; at the same time, stretched in the transverse direction by air blow. Herein, the draw ratio of final blow-molded article is not particularly limited; however, the draw ratio is preferably 1.2 to 6 times in the longitudinal direction and 1.2 to 4.5 times in the transverse direction.

Note that in the injection blow-molding, as a general technique, the final-shape mold is heated to a temperature at which crystallization of a resin is accelerated, for example, 120 to 230° C. and preferably 130 to 210° C. in the case of a PET resin. Thereafter, in the blowing step, a heat treatment is performed by bringing the outside wall of a molded article (container) into contact with the inner surface of the mold in a predetermined time. After the heat treatment is performed in a predetermined time, a fluid for blowing is changed to an internal cooling fluid to cool the inner layer. The heat treatment time at this time varies depending upon the thickness and temperature of a blow-molded article. The heat treatment time in the case of a PET resin, is generally 1.5 to 30 seconds and preferably 2 to 20 seconds. Whereas, the cooling time also varies depending upon the heat treatment temperature and the type of cooling fluid; however, the cooling time is generally 0.1 to 30 seconds and preferably 0.2 to 20 seconds. Owing to the heat treatment, each portions of the molded article is crystallized.

As the cooling fluid, air of normal temperature, cooled gases such as nitrogen, air, and carbon dioxide gas of −40° C. to +10° C. are used. Other than these, a chemically inactive liquefied gas such as liquefied nitrogen gas, liquefied carbonate gas, liquefied trichlorofluoromethane gas, liquefied dichlorodifluoromethane gas and other liquefied aliphatic hydrocarbon gases can be used. The cooling fluid may be used in combination with liquid mist requiring high heat of vaporization such as water. By using such a cooling fluid, significant cooling temperature can be provided. In stretch blow-molding, two molds are used. In the first mold, a heat treatment may be performed within a predetermined temperature and time and then the blow-molded article may be transferred to the second mold for cooling. The blow-molded article may be blow-molded again, simultaneously with being cooled. The outer layer of the blow-molded article taken out from the mold is allowed to stand still to cool it or cold air can be applied to cool the outer layer of the blow-molded article.

As another blow-molding method, a two-step blow-molding is exemplified, in which the aforementioned preform is processed into a primary blow-molded article, which is larger in size than a final blow-molded article, by use of a primary stretch-blow mold, and subsequently, the primary blow-molded article is heated to shrink, and then, processed into a final blow-molded article by stretch blow-molding using a secondary mold. According to the blow-molding method, the bottom of the blow-molded article is sufficiently stretched to reduce in thickness, with the result that a blow molded article with the bottom, which is rarely deformed during hot charging and heat sterilization and having excellent impact resistance can be obtained.

Note that the oxygen-absorbing injection-molded article of the embodiment and the container obtained by subjecting it to secondary processing may be coated with e.g., a vapor deposition film of an inorganic compound or an inorganic oxide or an amorphous carbon film.

Examples of the inorganic compound or inorganic oxide of the vapor deposition film include, but not particularly limited to, aluminum, alumina and silicon oxide. By virtue of the coating with a vapor deposition film of an inorganic compound or an inorganic oxide, it is possible to block elution of a low molecular weight organic compound from the injection-molded article of the embodiment and the container obtained by secondary processing of the article. Examples of the method for forming a vapor deposition film include a physical vapor deposition method such as a vacuum vapor deposition method, a sputtering method and an ion plating method, and chemical vapor deposition methods such as PECVD. However, the method for forming a vapor deposition film is not particularly limited to these and known methods can be applied. Note that the thickness of the vapor deposition film is not particularly limited; however, in view of gas barrier property, light-blocking property, flex resistance, etc., the thickness is preferably 5 to 500 nm and more preferable 5 to 200 nm.

An amorphous carbon film, which is known as a diamond carbon film, is a hard carbon film also called as an i-carbon film or a hydrogenated amorphous carbon film. Examples of a method for forming such an amorphous carbon film include, but not particularly limited to, a method in which the interior portion of a hollow molded article is exhausted to a vacuum, and then a carbon source gas is supplied and energy for generating a plasma is supplied to convert the carbon source gas into a plasma. In this manner, an amorphous carbon film is formed on the inner surface of the container. Owing to the coating with an amorphous carbon film, the transmission rate of a low molecular weight inorganic gas such as oxygen and carbon dioxide can be significantly reduced as well as adsorption of low molecular weight organic compounds having odor to an oxygen-absorbing injection-molded article can be suppressed. Note that the thickness of such an amorphous carbon film is not particularly limited; however, in view of effect of suppressing adsorption of a low molecular weight organic compound, effect of improving a gas barrier property, adhesion property to a plastic, durability, transparency, etc., the thickness is preferably 50 to 5000 nm.

(Seventh Embodiment)

Now, the seventh embodiment of the present invention will be described below. Note that repetition of explanation with respect to the same content as in the first to sixth embodiments is avoided herein.

[Oxygen-Absorbing Multilayer Injection-Molded Article]

The oxygen-absorbing multilayer injection-molded article of the embodiment at least has an oxygen-absorbing layer (layer A) formed of an oxygen-absorbing resin composition and a resin layer (layer B) containing a thermoplastic resin.

The oxygen-absorbing multilayer injection-molded article of the embodiment and a container obtained by secondary processing of the article can be applied to the same usage and use as described in the sixth embodiment. Oxygen within a container can be absorbed (even if the amount of oxygen transmitting or coming into the container from the outside through the wall of the container is small, transmitting or incoming oxygen is also absorbed) to prevent deterioration etc. of the content (article to be packaged) stored therein by oxygen.

In the oxygen-absorbing multilayer injection-molded article of the embodiment, the layer constitution is not particularly limited and the numbers and types of oxygen-absorbing layers (layer A) and resin layers (layer B) are not particularly limited. For example, an A/B, constitution, which is formed of one layer A and one layer B and a three-layer (B/A/B) constitution, which is formed of one layer A and two layers B, are acceptable. A five-layer (B1/B2/A/B2/B1) constitution, which is formed of one layer A and two layers B1 and two layers B2 is acceptable. The multilayer injection-molded article of the embodiment may have an optional layer such as an adhesion layer (layer AD), if necessary, and may be constituted of a seven-layers (e.g., B1/AD/B2/A/B2/AD/B1).

[Oxygen-Absorbing Layer (Layer A)]

In the oxygen-absorbing multilayer injection-molded article of the embodiment, the oxygen-absorbing layer (layer A) is formed of an oxygen-absorbing resin composition containing a polyester compound containing at least one constituent unit having a tetralin ring selected from the group consisting of the constituent units represented by the above general formulas (1) to (4) and a transition metal catalyst. The oxygen-absorbing resin composition used herein is the same as that described in the first embodiment. The oxygen-absorbing layer (layer A) is the same as described in the second embodiment.

[Resin Layer (Layer B)]

In the oxygen-absorbing multilayer injection-molded article of the embodiment, the resin layer (layer B) is a layer containing a thermoplastic resin. The content rate of the thermoplastic resin in layer B, which can be appropriately specified, is not particularly limited; however, the content rate is preferably 70 to 100 mass % based on the total amount of layer B, more preferably 80 to 100 mass % and further preferably 90 to 100 mass %.

The oxygen-absorbing multilayer injection-molded article of the embodiment may have a plurality of layers B. The constitution of the plural layers B may be the same or different. The thickness of layer B, which can be appropriately determined depending upon the use, is not particularly limited. In view of ensuring physical properties required for a multilayer injection-molded article such as strength including drop resistance and flexibility, the thickness is preferably 5 to 1000 μm, more preferably 10 to 800 μm and further preferably 20 to 500 μm.

As the thermoplastic resin to be used in layer B, any thermoplastic resin can be used and is not particularly limited. Specifically, thermoplastic resins as mentioned in the first embodiment are mentioned. In particular, the thermoplastic resin to be used in layer B of the embodiment is preferably at least one selected from the group consisting of a polyolefin, a polyester, a polyamide, an ethylene-vinyl alcohol copolymer, a vegetable-derived resin and a chlorine resin. Specific examples of these resins preferably used include the thermoplastic resins mentioned as those preferably used in layer B of an oxygen-absorbing multilayer body of the second embodiment. The thermoplastic resin to be used in layer B of the embodiment preferably contains a thermoplastic resin other than a tetralin ring-containing polyester compound as described in the first embodiment, in an amount of 50 to 100 mass % based on the total amount of layer B, more preferably 70 to 100 mass % and further preferably 90 to 100 mass %.

The oxygen-absorbing multilayer injection-molded article of the embodiment may have an optional layer, which varies depending upon desired performance etc. other than the aforementioned oxygen-absorbing layer (layer A) and resin layer (layer B). As such an optional layer, for example, an adhesion layer, is mentioned. The details of such an optional layer are the same as described in the second and the third embodiments.

As a method for manufacturing the oxygen-absorbing multilayer injection-molded article of the embodiment, a known method, which varies depending upon the properties of materials, a desired shape, etc., can be applied. Thus, the manufacturing method is not particularly limited. Various types of injection molding methods can be used for manufacturing the multilayer injection-molded article. Note that repetition of explanation with respect to general injection molding, which is the same as described in the sixth embodiment, is avoided herein and injection molding of a multilayer body will be generally described below.

For example, using a molding machine having 2 or more injectors and an injection mold, a material for constituting layer A and a material for constituting layer B are injected from respective injection cylinders through a mold hot runner into a cavity. In this manner, a multilayer injection-molded article of a two-layer (A/B) structure having a shape in accordance with the cavity shape of the injection mold can be manufactured. Furthermore, first, a material for constituting layer B is injected from the injection cylinder, and then, a material for constituting layer A is injected from another injection cylinder simultaneously with a resin for constituting layer B, subsequently, the resin for constituting layer B is injected in a necessary amount to fill the cavity to manufacture a multilayer injection-molded article constituted of three layers (B/A/B). Furthermore, first, a material for constituting layer B is injected, then a material for constituting layer A is solely injected, and finally the material for constituting layer B is injected in a necessary amount to fill the cavity to manufacture a multilayer injection-molded article constituted of five layers (B/A/B/A/B). Moreover, first, a material for constituting layer B1 is injected from an injection cylinder and then a material for constituting layer B2 is injected from another injection cylinder simultaneously with a resin for constituting layer B1, subsequently a resin for constituting layer A is injected simultaneously with resins for constituting layer B1 and layer B2 and thereafter the resin for constituting layer B1 is injected in a necessary amount to fill the cavity to manufacture a multilayer injection-molded article constituted of five layers (B1/B2/A/B2/B1).

The shape and thickness of the oxygen-absorbing multilayer injection-molded article of the embodiment are the same as those described as to the oxygen-absorbing injection-molded article of the sixth embodiment.

Usage of the oxygen-absorbing multilayer injection-molded article of the embodiment is the same as those described as to the oxygen-absorbing injection-molded article of the sixth embodiment. Furthermore, a method for secondary processing the oxygen-absorbing multilayer injection-molded article of the embodiment and the shape and usage of a container obtained by the secondary processing are the same as described in the sixth embodiment.

The oxygen-absorbing multilayer injection-molded article of the embodiment and the container obtained by secondary processing of the article may be coated with a vapor deposition film of an inorganic compound or an inorganic oxide or with an amorphous carbon film, etc. The details of these are the same as described in the sixth embodiment.

(Eighth Embodiment)

Now, the eighth embodiment of the present invention will be described below. Note that repetition of explanation with respect to the same content as in the first to seventh embodiments is avoided herein.

[Oxygen-Absorbing Multilayer Injection-Molded Article]

The oxygen-absorbing multilayer injection-molded article of the embodiment at least has an oxygen-absorbing layer (layer A) formed of an oxygen-absorbing resin composition and a resin layer (layer B) containing a thermoplastic resin (b).

The oxygen-absorbing multilayer injection-molded article of the embodiment and a container obtained by secondary processing of the article can be applied to the same usage and use as described in the sixth and seventh embodiments. Oxygen within a container can be absorbed (even if the amount of oxygen transmitting or coming into the container from the outside through the wall of the container is small, transmitting or incoming oxygen is also absorbed) to prevent deterioration etc. of the content (article to be packaged) stored therein by oxygen.

In the oxygen-absorbing multilayer injection-molded article of the embodiment, the layer constitution is not particularly limited and the numbers and types of oxygen-absorbing layers (layer A) and resin layers (layer B) are not particularly limited. For example, an A/B, constitution, which is formed of a single-layer A and a single-layer B and a three-layer (B/A/B) constitution, which is formed of a single-layer A and two layer-B, are acceptable. A five-layer (B1/B2/A/B2/B1) constitution, which is formed of a single-layer A and two B1 layers and two B2 layers is acceptable. The multilayer injection-molded article of the embodiment may have an optional layer such as an adhesion layer (layer AD), if necessary, and may be constituted of seven layers (e.g., B1/AD/B2/A/B2/AD/B1).

[Oxygen-Absorbing Layer (Layer A)]

In the oxygen-absorbing multilayer injection-molded article of the embodiment, oxygen-absorbing layer (layer A) is formed of an oxygen-absorbing resin composition containing a polyester compound, which contains at least one constituent unit having a tetralin ring selected from the group consisting of the constituent units represented by the above general formulas (1) to (4), a transition metal catalyst and a thermoplastic resin (a). The oxygen-absorbing resin composition is the same as described in the first embodiment as mentioned above except the following matter particularly described. Furthermore, the oxygen-absorbing layer (layer A) is the same as described in the second embodiment except the following matter particularly described.

In the oxygen-absorbing multilayer injection-molded article of the embodiment, as the thermoplastic resin (a) of the oxygen-absorbing layer (layer A), a known resin can be appropriately used and is not particularly limited. The thermoplastic resin (a) is preferably at least one selected from the group consisting of a polyolefin, a polyester, a polyamide and a vegetable-derived resin. Of these, in view of effectively exerting an oxygen absorption effect, a polyester, a polyamide, etc. are more preferable. As specific examples of these resins preferably used, the thermoplastic resins preferably used in layer B of the oxygen-absorbing multilayer body in the second embodiment are mentioned.

[Resin Layer (Layer B)]

In the oxygen-absorbing multilayer injection-molded article of the embodiment, the resin layer (layer B) is a layer containing a thermoplastic resin (b). The content rate of the thermoplastic resin (b) in layer B, which can be appropriately specified, is not particularly limited. The content rate is preferably 70 to 100 mass % based on the total amount of layer B, more preferably 80 to 100 mass % and further preferably 90 to 100 mass %.

The oxygen-absorbing multilayer injection-molded article of the embodiment may have a plurality of layers B and the constitution of plural layers B may be the same or different. The thickness of layer B is the same as described in the seventh embodiment.

As the thermoplastic resin (b) to be used in layer B, any thermoplastic resin can be used and is not particularly limited. Specific examples and preferable aspects of the thermoplastic resin (b) to be used in layer B are the same as thermoplastic resins to be used in layer B described in the seventh embodiment.

The oxygen-absorbing multilayer injection-molded article of the embodiment may have an optional layer, which varies depending upon desired performance etc., other than the aforementioned oxygen-absorbing layer (layer A) and resin layer (layer B). Examples of such an optional layer include an adhesion layer. The details of such an optional layer are the same as described in the second and third embodiments.

As a method for manufacturing the oxygen-absorbing multilayer injection-molded article of the embodiment, a known method, which varies depending upon the properties of materials, a desired shape, etc., can be applied. Thus, the manufacturing method is not particularly limited. A multilayer injection-molded article can be manufactured by applying various injection molding methods. Note that the details of general injection molding are the same as described in the sixth embodiment and the details of general injection molding of a multilayer body are the same as described in the seventh embodiment and repetition of explanation is avoided herein.

The shape and thickness of the oxygen-absorbing multilayer injection-molded article of the embodiment are the same as described in the oxygen-absorbing injection-molded article in the sixth embodiment.

Usage of the oxygen-absorbing multilayer injection-molded article of the embodiment is the same as described in the oxygen-absorbing injection-molded article in the sixth embodiment. In addition, a method for secondary processing of the oxygen-absorbing multilayer injection-molded article of the embodiment and the shape, usage, etc. of the container obtained by secondary processing are the same as described in the sixth embodiment.

The oxygen-absorbing multilayer injection-molded article of the embodiment and the container obtained by secondary processing it may be coated with a vapor deposition film of an inorganic compound or an inorganic oxide or an amorphous carbon film, etc. The details of these are the same as described in the sixth embodiment.

(Ninth Embodiment)

Now, the ninth embodiment of the present invention will be described below. Note that repetition of explanation with respect to the same content as in the first to eighth embodiments is avoided herein.

The oxygen-absorbing medical multilayer molded container of the embodiment has at least three layers, i.e., a first resin layer (layer B) at least containing a thermoplastic resin, an oxygen-absorbing layer (layer A) formed of an oxygen-absorbing resin composition, a second resin layer (layer B) at least containing a thermoplastic resin, in this order.

The oxygen-absorbing medical multilayer molded container of the embodiment can absorb oxygen within the container (even if the amount of oxygen transmitting or coming into the container from the outside through the wall of the container is small, transmitting or incoming oxygen is also absorbed) to prevent deterioration etc. of the content (article to be packaged) stored therein by oxygen.

The layer constitution of the oxygen-absorbing medical multilayer molded container of the embodiment is not particularly limited. More specifically, the numbers and types of oxygen-absorbing layers (layer A) and resin layers (layer B) are not particularly limited as long as these layers are arranged in the order of B/A/B. For example, a five-layer (B1/B2/A/B2/B1) structure, which is constituted of one layer A and two layers B1 and two layers B2, may be acceptable. Furthermore, the oxygen-absorbing medical multilayer molded container of the embodiment, may have an optional layer, if necessary, such as an adhesion layer (layer AD). For example, seven-layer (B1/AD/B2/A/B2/AD/B1) structure is acceptable.

[Oxygen-Absorbing Layer (Layer A)]

In the oxygen-absorbing medical multilayer molded container of the embodiment, the oxygen-absorbing layer (layer A) is formed of an oxygen-absorbing resin composition containing at least one tetralin ring-containing polyester compound selected from the group consisting of the constituent units represented by the above general formulas (1) to (4) and a transition metal catalyst. The oxygen-absorbing resin composition is the same as that described in the first embodiment except the following matters particularly described. Furthermore, the oxygen-absorbing layer (layer A) is the same as that described in the second embodiment except the following matters particularly described.

In the oxygen-absorbing medical multilayer molded container of the embodiment, the thickness of the oxygen-absorbing layer (layer A), which can be appropriately specified depending upon use and desired performance, is not particularly limited. In view of having high oxygen-absorbing performance and ensuring physical properties required for a medical multilayer molded container, the thickness is preferably 1 to 1000 μm, more preferably 50 to 900 μm and further preferably 100 to 800 μm.

[Resin Layer (Layer B) Containing a Thermoplastic Resin]

In the oxygen-absorbing medical multilayer molded container of the embodiment, the resin layer (layer B) is a layer containing a thermoplastic resin. The content rate of the thermoplastic resin in layer B, which can be appropriately specified, is not particularly limited. The content rate is preferably 70 to 100 mass % based on the total amount of layer B, more preferably 80 to 100 mass % and further preferably 90 to 100 mass %.

The oxygen-absorbing medical multilayer molded container of the embodiment may have a plurality of layers B. The constitution of the plural layers B may be the same or different. The thickness of layer B, which can be appropriately determined depending upon the use, is not particularly limited. In view of ensuring physical properties required for a medical multilayer molded container, the thickness is preferably 50 to 10000 μm, more preferably 100 to 7000 μm and further preferably 300 to 5000 μm.

As thermoplastic resin to be used in layer B of the embodiment, any thermoplastic resin can be used and is not particularly limited. Specifically, thermoplastic resins described in the first embodiment are mentioned. In particular, the thermoplastic resin to be used in layer B of the embodiment is preferably at least one selected from the group consisting of a polyolefin, a polyester, a polyamide, an ethylene-vinyl alcohol copolymer, a vegetable-derived resin and a chlorine resin. Note that the thermoplastic resin to be used in layer B of the embodiment preferably contains a thermoplastic resin except the tetralin ring-containing polyester compound according to the first embodiment in an amount of 50 to 100 mass %, more preferably 70 to 100 mass % and particularly preferably 90 to 100 mass %.

<Polyolefin>

Specific examples of the polyolefin to be used in layer B of the embodiment include, but not particularly limited to, polyethylenes (low-density polyethylene, medium-density polyethylene, high-density polyethylene, straight (linear) low-density polyethylene), polypropylenes, polybutene-1, poly-4-methylpentene-1, a copolymer between ethylene and an α-olefin, a copolymer between a propylene and an α-olefin, a copolymer between ethylene and an α,β-unsaturated carboxylic acid, and a copolymer between ethylene and an α,β-unsaturated carboxylic acid ester. As specific examples of these polyolefins, the thermoplastic resins preferably used in layer B of an oxygen-absorbing multilayer body in the second embodiment are mentioned. In particular, a ring opened polymer of a cycloolefin such as norbornene or tetracyclododecene or a derivatives thereof and a hydrogenated product thereof; and a copolymer (resin) having a cyclopentyl residue or a substituted cyclopentyl residue inserted in a molecular chain by polymerization between a cycloolefin such as norbornene or tetracyclododecene, or a derivative thereof and ethylene or propylene, are more preferable. Examples of the cycloolefin herein include monocyclic olefins and polycyclic olefins. Furthermore, a thermoplastic norbornene resin or a thermoplastic tetracyclododecene resin is one of more preferable resins. Examples of the thermoplastic norbornene resin include a ring opened polymer of a norbornene monomer and a hydrogenated product thereof; an addition polymer of a norbornene monomer; and an addition polymer of a norbornene monomer and an olefin. Examples of the thermoplastic tetracyclododecene resin include a ring opened polymer of a tetracyclododecene monomer and a hydrogenated product thereof; an addition polymer of a tetracyclododecene monomer; and an addition polymer of a tetracyclododecene monomer and an olefin. The thermoplastic norbornene resins are, for example, described in Japanese Patent Laid-Open No. 3-14882, Japanese Patent Laid-Open No. 3-122137, Japanese Patent Laid-Open No. 4-63807, etc.

Particularly preferable ones are a copolymer using norbornene and an olefin such as ethylene as raw materials and a cycloolefin copolymer (COC), which is a copolymer using tetracyclododecene and an olefin such as ethylene as raw materials. Furthermore, a cycloolefin polymer (COP), which is a polymer obtained by ring opening polymerization of a norbornene, followed by hydrogenating it, is particularly preferable. Such a COC and COP are, for example, described in Japanese Patent Laid-Open No. 5-300939 or Japanese Patent Laid-Open No. 5-317411.

COC is commercially available, for example, as APEL (registered trade mark) manufactured by Mitsui Chemicals Inc., whereas COP is commercially available, for example, as ZEONEX (registered trade mark) or ZEONOR (registered trade mark) manufactured by ZEON Corporation and as Dalkyo Resin CZ (registered trade mark) manufactured by Dalkyo Seko, Ltd. COC and COP exhibit chemical properties such as heat resistance and light resistance, chemical resistance (which are the feature derived from a polyolefin resin), and physical properties such as mechanical properties, fusion characteristics, flow properties and dimension accuracy (which are features derived from an amorphous resin). For this reason, the quality of COC and COP are most preferable.

<Polyester>

The polyester to be used in layer B of the embodiment does not contain a tetralin ring-containing polyester compound described in the first embodiment. More specifically, the polyester compound (b) to be used in layer B of the embodiment is a polyester compound that does not contain a constituent unit having a tetralin ring selected from the group consisting of the constituent units represented by the above general formulas (1) to (4). In the embodiment, the polyester compound (b) refers to a compound formed of at least one selected from polyvalent carboxylic acids containing a dicarboxylic acid having no tetralin ring and ester-forming derivatives of these and at least one selected from polyhydric alcohols containing glycol having no tetralin ring, a compound formed of a hydroxy carboxylic acid having no tetralin ring and an ester-forming derivative thereof, or a compound formed of a cyclic ester containing no tetralin ring. As specific examples of the polyester to be used in layer B of the embodiment, thermoplastic resins preferably used in layer B of the oxygen-absorbing multilayer body in the second embodiment are mentioned.

In particular, as the polyester to be used in layer B of the embodiment, a polyester containing terephthalic acid or an ester-forming derivative thereof or a naphthalene dicarboxylic acid or an ester-forming derivative thereof as a main acid component and containing an alkylene glycol as a main glycol component, is preferable. Of the aforementioned dicarboxylic acids, particularly, use of terephthalic acid, isophthalic acid, 1,3-naphthalene dicarboxylic acid, 1,4-naphthalene dicarboxylic acid, 1,5-naphthalene dicarboxylic acid, 2,6-naphthalene dicarboxylic acid or 2,7-naphthalene dicarboxylic acid is preferable in view of physical properties etc. of the resultant polyester. These are preferably contained in an amount of 70 mole % or more. Of these dicarboxylic acids, particularly terephthalic acid and/or 2,6-naphthalene dicarboxylic acid are preferable. Furthermore, terephthalic acid and/or 2,6-naphthalene dicarboxylic acid are preferably contained in an amount of 70 mole % or more in view of physical properties etc., and more preferably in an amount of 90 mole % or more. If necessary, another dicarboxylic acid may be copolymerized. Furthermore, use of at least one copolymer component selected from the group consisting of isophthalic acid, diethylene glycol, neo-pentyl glycol, 1,4-cyclohexane dimethanol, 1,2-propanediol, 1,3-propanediol and 2-methyl-1,3-propanediol is preferable in view of obtaining transparency and moldability at the same time, particularly at least one selected from the group consisting of isophthalic acid, diethylene glycol, neopentyl glycol and 1,4-cyclohexanedimethanol is more preferable.

<Polyamide>

As specific examples of the polyamide to be used in layer B of the embodiment, the thermoplastic resins preferably used in layer B of the oxygen-absorbing multilayer body in the second embodiment are mentioned.

<Ethylene-Vinyl Alcohol Copolymer>

As specific examples of the ethylene-vinyl alcohol copolymer to be used in layer B of the embodiment, the thermoplastic resins preferably used in layer B of the oxygen-absorbing multilayer body in the second embodiment are mentioned.

<Vegetable-Derived Resin>

As specific examples of the vegetable-derived resin to be used in layer B of the embodiment, the thermoplastic resins preferably used in layer B of the oxygen-absorbing multilayer body in the second embodiment are mentioned.

<Chlorine Resin>

As specific examples of the vegetable-derived resin to be used in layer B of the embodiment, the thermoplastic resins preferably used in layer B of the oxygen-absorbing multilayer body in the second embodiment are mentioned.

As a preferable aspect of the oxygen-absorbing medical multilayer molded container of the embodiment, an aspect where the thermoplastic resin of the first resin layer (layer B) and the second thermoplastic resin both are polyolefins; and an aspect where the thermoplastic resin of the first resin layer (layer B) and the second thermoplastic resin both are polyesters and containing no tetralin ring-containing polyester compound described in the first embodiment are mentioned.

The oxygen-absorbing medical multilayer molded container of the embodiment may have an optional layer, which varies depending upon desired performance etc., other than the aforementioned oxygen-absorbing layer (layer A) and resin layer (layer B) containing a thermoplastic resin. As such an optional layer, for example, an adhesion layer is mentioned. The details of such an optional layer are the same as described in the second and third embodiments.

As a method for manufacturing the oxygen-absorbing medical multilayer molded container of the embodiment, a known method varying depending upon the properties of materials, a desired shape, etc. can be applied, but is not particularly limited. For example, a multilayer molded container can be manufactured by applying various types of injection molding methods. Note that the details of general injection molding are the same as described in the sixth embodiment, and the details of general injection molding of the multilayer body are the same as described in the seventh embodiment, thus repetition of explanation is avoided herein.

A multilayer molded article can be obtained by a method other than the injection molding method, for example, a compression molding method. To the resultant multilayer molded article, secondary processing is applied to mold the article into a container having a desired shape. For example, in a thermoplastic resin melt, an oxygen-absorbing resin composition is provided and a molten lump is supplied to a positive die and simultaneously compressed by a negative die and then compression molded product is cooled and solidified. In this manner, a multilayer molded article can be obtained. As the secondary processing, for example, extrusion molding, compression molding (sheet molding, blow-molding), etc. are applicable.

Usage of the oxygen-absorbing medical multilayer molded container of the embodiment is not particularly limited. The container can be used for various uses and in various forms. Examples of preferable usage thereof include, but not particularly limited to, vials, ampules, prefilled syringes and vacuum blood collection tubes. Now, preferable usage will be described in detail, below.

[Vial]

The oxygen-absorbing medical multilayer molded container of the embodiment can be used as a vial.

Generally, a vial is constituted of a bottle, a rubber tap and a cap. The bottle is filled with a drug solution, stoppered by the rubber tap and further capped to hermetically close the bottle. The oxygen-absorbing medical multilayer molded container of the embodiment can be used as the bottle portion of the vial.

As a method for molding the oxygen-absorbing medical multilayer molded container of the embodiment into a bottle portion of a vial, for example, injection blow-molding and extrusion blow-molding are preferable. As a specific example thereof, an injection blow-molding method will be described below. For example, using a molding machine having two or more injectors and an injection mold, a material for constituting layer A and a material for constituting layer B are separately injected from respective injection cylinders through a mold hot runner into the cavity of the injection mold to manufacture a multilayer injection-molded article constituted of three layers (B/A/B) having a shape in accordance with a cavity shape of the injection mold. Furthermore, first, a material for constituting layer B is injected from the injection cylinder, and then, a material for constituting layer A is injected from another injection cylinder simultaneously with a resin for constituting layer B, subsequently, the resin for constituting layer B is injected in a necessary amount to fill the cavity to manufacture a multilayer injection-molded article constituted of three layers (B/A/B). Furthermore, first, a material for constituting layer B is injected, then a material for constituting layer A is solely injected, and finally the material for constituting layer B is injected in a necessary amount to fill the mold cavity to manufacture a multilayer injection-molded article constituted of five layers (B/A/B/A/B). Moreover, first, a material for constituting layer B1 is injected from an injection cylinder and then a material for constituting layer B2 is injected from another injection cylinder simultaneously with a resin for constituting layer B1, subsequently a resin for constituting layer A is injected simultaneously with resins for constituting layer B1 and layer B2 and thereafter the resin for constituting layer B1 is injected in a necessary amount to fill the cavity to manufacture a multilayer injection-molded article constituted of five layers (B1/B2/A/B2/B1). In the injection blow-molding, the multilayer injection-molded article obtained by the above method is heated to some extent. While keeping this state, the article is fit in a final-shape mold (blow mold) and air is fed to swollen the article, with the result that the article comes into contact with the mold. Then, the article was cooled and solidified to mold a bottle.

[Ampule]

The oxygen-absorbing medical multilayer molded container of the embodiment can be used as an ampule. Generally, an ampule is constituted of a small container having a narrow neck. The container is filled with a drug solution and the tip of the neck portion is welded to hermetically close the container. The oxygen-absorbing medical multilayer molded container of the embodiment can be used as the ampule (small container). As a method for molding the oxygen-absorbing medical multilayer molded container of the embodiment into an ampule, for example, injection blow-molding and extrusion blow-molding are preferred.

[Prefilled Syringe]

The oxygen-absorbing medical multilayer molded container of the embodiment can be used as a prefilled syringe. Generally, a prefilled syringe is at least constituted of a barrel to be filled with drug solution, a joint portion for joining an injection needle at an end of the barrel and a plunger for pushing the drug solution at the time of use. This is a syringe constituted in such a manner that a drug solution is stored in advance in a sealed condition in the barrel and the tip portion of the barrel is opened and an injection needle is fit to the barrel at the time of use. Owing to its convenience, prefilled syringe is widely used. The oxygen-absorbing medical multilayer molded container of the embodiment can be used as the barrel.

As a method for molding the oxygen-absorbing medical multilayer molded container of the embodiment into a barrel of the prefilled syringe, for example, an injection molding method is preferred. To describe more specifically, first, a resin for constituting layer B is injected into the cavity of an injection mold in a predetermined amount. Then, a resin for constituting layer A is injected in a predetermined amount and the resin for constituting layer B is again injected in a predetermined amount to manufacture a multilayer injection-molded article serving as a barrel. Note that the barrel and the joint portion can be integrally molded or they are separately molded and then joined. After the barrel is filled with a drug solution, the tip portion of the joint portion must be sealed. As the sealing method, which is not particularly limited, a known method can be employed. For example, the resin of the joint tip portion is heated, melted and clipped by a pincher etc. to fuse.

The thickness of the barrel container of the prefilled syringe, which can be appropriately specified depending upon the purpose of use and size, is not particularly limited. Generally, in view of long-term storage stability of a drug solution, moldability and operability of the syringe, the thickness is preferably about 0.5 to 20 mm and more preferably about 0.5 to 5 mm. The thickness may be uniform or nonuniform. For the purpose of long-term storage stability, another gas barrier film and light blocking film may be further formed on the barrel surface. These optional films and a method for forming them are described, for example, in Japanese Patent Laid-Open No. 2004-323058.

[Vacuum Blood Collection Tube]

The oxygen-absorbing medical multilayer molded container of the embodiment can be used as a vacuum blood collection tube. Generally, a vacuum blood collection tube is constituted of a tubular body and a tap. The oxygen-absorbing medical multilayer molded container of the embodiment can be used as the tubular body.

As a method for molding the oxygen-absorbing medical multilayer molded container of the embodiment into a tubular body of a vacuum blood collection tube, for example, an injection molding method is preferred. To describe more specifically, first, a resin for constituting layer B is injected into the cavity of an injection mold in a predetermined amount and then a resin for constituting layer A is injected in a predetermined amount, and then, the resin for constituting layer B is injected again in a predetermined amount to manufacture a multilayer injection-molded article serving as the tubular body.

[Article to be Packaged]

Examples of the article to be packaged (filler) that is to be packed in the oxygen-absorbing medical multilayer molded container of the embodiment include, but not particularly limited to, arbitrary natural substances and compounds including vitamins such as vitamin A, vitamin B2, vitamin B12, vitamin C, vitamin D, vitamin E and vitamin K; alkaloids such as atropine; hormones such as adrenaline and insulin; sugars such as glucose and maltose; antibiotics such as ceftriaxone, cephalosporin and cyclosporine; and benzodiazepine medicinal agents such as oxazolam, flunitrazepam, clotiazepam and clobazam. When these natural substances and compounds each are packed in the oxygen-absorbing medical multilayer molded container of the embodiment, the amount of natural substances and compounds adsorbed is small and deterioration of these by oxidation can be suppressed. In addition, evaporation of a solvent (for example moisture content) can be suppressed.

[Biopharmaceutical]

The oxygen-absorbing medical multilayer molded container of the embodiment can be preferably used as a storage container for biopharmaceutical. In view of the effect of the embodiment, as a biopharmaceutical that can be preferably used include protein preparations and nucleic acid pharmaceutical preparations. Specific examples thereof include, but not particularly limited to, monoclonal antibodies, vaccines, interferon, insulin, growth hormone, erythropoietin, colony stimulating factor, TPA, interleukin, blood coagulation factor VIII, blood coagulation factor IX, sodium diuresis hormone, somatomedin, glucagon, serum albumin, calcitonin, growth hormone-releasing factor, digestive enzymes, inflammation enzymes, antibiotics, antisense nucleic acids, antigene nucleic acids, decoy nucleic acids, aptamers, siRNA and microRNA. When these biopharmaceuticals each are packed in a medical multilayer container, the amount of these biopharmaceuticals adsorbed is small and deterioration of these medicines by oxidation and reduction of drug efficacy can be suppressed. In addition, evaporation of a solvent (for example moisture content) can be suppressed.

Note that, before and after packing of these articles to be packaged, sterilization treatment can be applied to medical multilayer containers and the articles to be packaged by a method suitable for the articles to be packaged. Examples of a sterilization method include a hot water treatment performed at 100° C. or less, a hot water treatment under application of pressure performed at 100° C. or more, thermal sterilization performed at a temperature as high as 121° C. or more, sterilization by electromagnetic wave such as UV ray, microwave and gamma ray, a treatment with a gas such as ethylene oxide and sterilization with a chemical agent such as hydrogen peroxide and hypochlorite.

(Tenth Embodiment)

Now, the tenth embodiment of the present invention will be described below. Note that repetition of explanation with respect to the same content as in the first to eighth embodiments is avoided herein.

The embodiment relates to a method for storing an alcohol beverage; more specifically, a method for storing an alcohol beverage in an oxygen-absorbing multilayer container using an oxygen-absorbing multilayer body at least having an oxygen-absorbing layer (layer A) formed of an oxygen-absorbing resin composition at least containing at least one tetralin ring-containing polyester compound selected from the group consisting of the constituent units represented by the above general formulas (1) to (4) and a transition metal catalyst, and a resin layer (layer B) containing a thermoplastic resin, in whole or in part.

[Alcohol Beverage]

The alcohol beverage to be stored is not particularly limited as long as it is a beverage containing ethyl alcohol, and the concentration of alcohol is not particularly limited. Specific examples thereof include, but not particularly limited to, low alcohol beverages such as cocktails; distilled alcoholic beverages (whiskey, rum, cachaca, vodka, gin, tequila, brandy, raki, arrack, ouzo, white sake, shochu, Okinawan millet brandy); brewages (wine, beer, fruit wine, Chinese rice wine, Japanese sake); mixed liquors (liqueur, sweet sake), and beverages containing these.

The oxygen-absorbing resin composition, oxygen-absorbing multilayer body and oxygen-absorbing multilayer container to be used in the store method of the embodiment can be appropriately selected from those described in the first to eighth embodiments depending upon use and the desired performance and put in use.

In the store method of the embodiment, an alcohol beverage is stored by use of the oxygen-absorbing multilayer container according to any one of the first to eighth embodiments, more specifically, containers having excellent oxygen-absorbing performance, satisfactory oxygen barrier property, generating no odor after absorption of oxygen and having excellent strength after long-term storage. Therefore, oxygen within the container is absorbed (even if the amount of oxygen transmitting or coming into the container from the outside through the wall of the container is small, transmitting or incoming oxygen is also absorbed). Thus, the taste and flavor of the alcohol beverage is satisfactorily and stably maintained for a long term. In addition, since the oxygen-absorbing multilayer containers according to the first to eighth embodiments each require no iron-based oxygen absorbent, reduction of taste and flavor due to the reaction between iron and an alcohol can be prevented. Furthermore, a metal detector for inspecting foreign matter can be applied. Moreover, light weight and reduction of non-combustible waste can be attained by alternation of metal cans and glass bottles.

(Eleventh Embodiment)

Now, the eleventh embodiment of the present invention will be described below. Note that repetition of explanation with respect to the same contents as in the first to eighth embodiments is avoided herein.

The embodiment relates to a method for storing a fruit juice and/or a vegetable juice; more specifically, a method for storing a fruit juice and/or a vegetable juice in an oxygen-absorbing multilayer container using an oxygen-absorbing multilayer body at least having an oxygen-absorbing layer (layer A) formed of an oxygen-absorbing resin composition at least containing at least one tetralin ring-containing polyester compound selected from the group consisting of the constituent units represented by the above general formulas (1) to (4) and a transition metal catalyst, and a resin layer (layer B) containing a thermoplastic resin, in whole or in part.

The oxygen-absorbing resin composition, oxygen-absorbing multilayer body and oxygen-absorbing multilayer container to be used in the store method of the embodiment can be appropriately selected from those described in the first to eighth embodiments depending upon use and the desired performance and put in use.

[Fruit Juice, Vegetable Juice]

The fruit juice and/or vegetable juice to be stored is not particularly limited as long as it contains a liquid obtained from a raw material fruit and/or vegetable. Fruit juice and vegetable juice can be obtained by grinding or squeezing fruit or vegetable. Such fruit juice and vegetable juice may contain solid substances and insoluble components of the raw materials. Examples of raw-material fruit and/or vegetables include, but not particularly limited to, fruit vegetables such as orange, mandarin orange, apple, peach, pear, grape, blueberry, grapefruit, pineapple, Citrus depressa, guava, acerola, prune, papaya, mango, melon, kiwi fruit, candleberry, banana, citron, citrus lemon, tomato, eggplant, pumpkin, green pepper, bitter gourd, sponge gourd, wax gourd, okra, green soybean, snow peas, green bean, fava bean, red pepper, corn and cucumber; root vegetables such as carrot, burdock, onion, bamboo shoot, lotus root, radish, Japanese radish, potato, sweet potato, taro, rakkyo, garlic and ginger; and leaf vegetables such as molokheiya, asparagus, celery, kale, qing-geng-cai, spinach, Chinese cabbage, cabbage, lettuce, napa, broccoli, cauliflower, honewort, parsley, leek, crown daisy and Chinese leek. Furthermore, fruit juices and/or vegetable juices, which are obtained by a heat treatment such as boiling, baking, warming and steaming these raw materials and obtained by applying a non-heat treatment such as sufficient washing with water, immersing in water, treatment with a chemical agent, before and after squeezing, are applicable. Furthermore, the fruit juices and/or vegetable juices, from which predetermined components are removed by passing the fruit juices and/or vegetable juices through a predetermined resin, are applicable. Note that these fruit juices and vegetable juices can be used alone or in combination with two or more.

The fruit juices and/or vegetable juices may contain additives including sugars and sweeteners such as sugar, glucose, fructose, fructose glucose liquid sugar syrup, glucose fructose liquid sugar syrup, high-fructose liquid sugar syrup, oligosaccharide, trehalose, xylitol, sucralose, stevia extract, sorbitol, sweetroot extract and Momordica grosvenori extract; thickening stabilizers such as pectin, gelatin, collagen, agar, carrageenan, sodium alginate, soybean polysaccharide, gum Arabic, guar gum, xanthan gum, Tamarindus seed gum and gellan gum; acidulants such as citric acid, malic acid, tartaric acid, lactic acid and gluconic acid; antioxidants such as L-ascorbic acid, sodium L-ascorbate; pH moderators such as sodium hydrogen carbonate; emulsifiers such as glycerin fatty acid ester and sucrose fatty acid ester; nutritional enhancements such as dietary fiber, calcium salt, magnesium salt, niacin and pantothenic acid; spice such as turmeric; and flavoring.

In the store method of the embodiment, fruit juice and/or vegetable juice is stored by use of the oxygen-absorbing multilayer container according to any one of the first to eighth embodiments, more specifically, a container having excellent oxygen-absorbing performance, a satisfactory oxygen barrier property, generating no odor after absorption of oxygen, and having excellent strength after long-term storage. Therefore, oxygen within the container is absorbed (even if the amount of oxygen transmitting or coming into the container from the outside through the wall of the container is small, transmitting or incoming oxygen is also absorbed). Thus taste and flavor and color tone of the fruit juice and/or vegetable juice are satisfactorily and stably maintained for a long term. In addition, since the oxygen-absorbing multilayer containers according to the first to eighth embodiments each require no iron-based oxygen absorbent, a metal detector for inspecting foreign matter can be applied. Moreover, light weight and reduction of non-combustible waste can be attained by alternation of metal cans and glass bottles.

Note that fruit juice and/or vegetable juice is rich in components, whose taste and flavor and color tone are significantly changed by oxygen oxidation, such as flavor components, sugars and vitamins. More specifically, as the flavor components of fruit juice and/or vegetable juice, for example, terpenes such as d-limonene, γ-terpinene, myrcene, α-pinene, β-pinene, citronellol and linalool and aldehydes such as n-octylaldehyde and n-decylaldehyde are contained in citrus fruit juices; esters such as amyl butyrate and amyl acetate and aldehydes such as hexanal and trans-2-hexanal are contained in apple juices; esters such as methyl anthranilate and ethyl crotonate and terpenes such as linalool and geraniol are contained in grape juices; and terpenes such as α-pinene, myrcene and d-limonene and aldehydes such as hexanal and heptanal are contained in vegetable juices using tomato as a raw material. However, in the store method of the embodiment, oxidation of these flavor components etc. by oxygen can be suppressed without fail, compared to conventional methods. Thus, the taste and flavor and color tone of fruit juices and/or vegetable juices are maintained well for a long term.

(Twelfth Embodiment)

Now, the twelfth embodiment of the present invention will be described below. Note that repetition of explanation with respect to the same contents as in the first to eighth embodiments is avoided herein.

The embodiment relates to a method for storing broths. More specifically, a method for storing a broth in an oxygen-absorbing multilayer container using an oxygen-absorbing multilayer body at least having an oxygen-absorbing layer (layer A) formed of an oxygen-absorbing resin composition at least containing at least one tetralin ring-containing polyester compound selected from the group consisting of the constituent units represented by the above general formulas (1) to (4) and a transition metal catalyst, and a resin layer (layer B) containing a thermoplastic resin, in whole or in part.

[Oxygen-Absorbing Multilayer Containers]

The oxygen-absorbing resin composition, oxygen-absorbing multilayer body and oxygen-absorbing multilayer container to be used in the store method of the embodiment can be appropriately selected from those described in the first to eighth embodiments depending upon use and the desired performance and put in use.

[Broths]

In the specification, broth refers to a product obtained by blending seasonings such as soy sauce, sweet sake, sugar and glutaminic acid and extracts with soup stock extracted from dried bonito, seaweeds, etc. Specific examples thereof include noodle broth, tempura broth and broth for simmered dish. Broth is used in wide variety of usage. Broth is poured in noodles, used as a seasoning for simmered dishes and as soup for Japanese nabe, used as a soak for tempra, poured on chilled tofu and grated radish and processed into dressings, Japanese sources, etc. in combination with other seasonings.

The broths may contain additives including sugars and sweeteners such as sugar, glucose, fructose, fructose glucose liquid sugar syrup, glucose fructose liquid sugar syrup, high-fructose liquid sugar syrup, oligosaccharide, trehalose, xylitol, sucralose, stevia extract, sorbitol, sweetroot extract and Momordica grosvenori extract; thickening stabilizers such as pectin, gelatin, collagen, agar, carrageenan, sodium alginate, soybean polysaccharide, gum Arabic, guar gum, xanthan gum, Tamarindus seed gum and gellan gum; acidulants such as citric acid, malic acid, tartaric acid, lactic acid and gluconic acid; antioxidants such as L-ascorbic acid and sodium L-ascorbate; pH moderators such as sodium hydrogen carbonate; emulsifiers such as glycerin fatty acid ester and sucrose fatty acid ester; nutritional enhancements such as dietary fiber, calcium salt, magnesium salt, niacin and pantothenic acid; spice such as turmeric; and flavoring.

In the store method of the embodiment, broth is stored by use of the oxygen-absorbing multilayer container according to any one of the first to eighth embodiments, more specifically a container having excellent oxygen-absorbing performance, a satisfactory oxygen barrier property, generating no odor after absorption of oxygen, and having excellent strength after long-term storage. Therefore, oxygen within the container is absorbed (even if the amount of oxygen transmitting or coming into the container from the outside through the wall of the container is small, transmitting or incoming oxygen is also absorbed). Thus taste and flavor and color tone of the broth are satisfactorily and stably maintained for a long term. In addition, since the oxygen-absorbing multilayer containers according to the first to eighth embodiments each require no iron-based oxygen absorbent, a metal detector for inspecting foreign matter can be applied. Moreover, light weight and reduction of non-combustible waste can be attained by alternation of metal cans and glass bottles.

Note that broths are rich in components, whose taste and flavor and color tone are changed by oxygen oxidation, such as various seasonings and extracts. In particular, when soy sauce and sugar are oxidized by oxygen, problems of taste and flavor change, reduction of storage stability and color change to brown easily occur. However, in the store method of the embodiment, oxidation of these seasonings etc. by oxygen can be suppressed without fail, compared to conventional methods. Thus, the taste and flavor and color tone of broths are satisfactorily maintained for a long term.

(Thirteenth Embodiment)

Now, the thirteenth embodiment of the present invention will be described below. Note that repetition of explanation with respect to the same contents as in the first to eighth embodiments is avoided herein.

The embodiment relates to a method for storing a liquid-state tea or a paste-state tea. More specifically, a method for storing a liquid-state tea or a paste-state tea in an oxygen-absorbing multilayer container using an oxygen-absorbing multilayer body at least having an oxygen-absorbing layer (layer A) formed of an oxygen-absorbing resin composition at least containing at least one tetralin ring-containing polyester compound selected from the group consisting of the constituent units represented by the above general formulas (1) to (4) and a transition metal catalyst, and a resin layer (layer B) containing a thermoplastic resin, in whole or in part.

[Oxygen-Absorbing Multilayer Containers]

The oxygen-absorbing resin composition, oxygen-absorbing multilayer body and oxygen-absorbing multilayer container to be used in the store method of the embodiment can be appropriately selected from those described in the first to eighth embodiments depending upon use and the desired performance and put in use.

[Liquid-State Tea or Paste-State Tea]

In the specification, the liquid-state tea refers to a liquid-state tea beverage obtained by extracting tea as it is or ground tea powder with hot water and refers to concentrated tea liquid obtained by treating such a tea beverage by a known method such as vacuum concentration. The paste-state tea refers to tea obtained by blending powdered tea obtained by grinding tea with a fat and oil and/or water. Herein, as tea serving as a raw material, non-fermented tea (green tea), half fermented tea or fermented tea is mentioned. Examples of the non-fermented tea include green teas such as high-quality green tea, powdered green tea, green tea of medium quality, green tea of ordinary quality, sweet tea and curled leaf tea, and roasted teas obtained by roasting green teas. Examples of the half-fermented tea include oolong tea and Pouchong tea. Examples of the fermented tea include red tea.

The fat and oil that may be contained in paste-state tea, which can be appropriately selected from known fats and oils and put in use, is not particularly limited. In view of a liquid state at normal temperature and easiness in blending with powdered tea, for example, vegetable oils such as cotton seed oil, sesame oil, olive oil, camellia oil, palm oil, corn oil, bean oil, rapeseed oil, sunflower oil and coconut oil; and oil mixtures containing two or more oils selected from these are preferred. In view of not damaging color, taste and flavor, and scent of tea, fat and oil having no taste, no odor and no color is preferable. To obtain paste-state tea, an emulsifier may be appropriately added. If an emulsifier is added, water soluble paste-state tea can be easily obtained, which can be used, for example, in processed foods such as a soft cream. Furthermore, depending upon the use, a seasoning such as a sweetener may be appropriately added in advance. Moreover, a nutrient such as ascorbic acid may be appropriately added.

These liquid-state tea beverage, concentrated tea and paste-state tea may be treated with heat. The temperature and time of the heat treatment, which can be specified in accordance with a conventional method, are not particularly limited. For example, conditions where a coliform group cannot survive and conditions where other general viable bacteria cannot survive, are particularly mentioned.

In the store method of the embodiment, liquid-state tea or paste-state tea is stored by use of the oxygen-absorbing multilayer container according to any one of the first to eighth embodiments, more specifically, a container having excellent oxygen-absorbing performance, a satisfactory oxygen barrier property, generating no odor after absorption of oxygen, and having excellent strength after long-term storage. Therefore, oxygen within the container is absorbed (even if the amount of oxygen transmitting or coming into the container from the outside through the wall of the container is small, transmitting or incoming oxygen is also absorbed). Thus, taste and flavor and color tone of the liquid-state tea or paste-state tea are satisfactorily and stably maintained for a long term. In addition, since the oxygen-absorbing multilayer containers according to the first to eighth embodiments each require no iron-based oxygen absorbent, a metal detector for inspecting foreign matter can be applied. Furthermore, light weight and reduction of non-combustible waste can be attained by alternation of metal cans and glass bottles.

Although already known well, natural tea is a healthy food rich in vitamins and fibers and has been long and widely used in dietary life. Furthermore, scent and flavor and taste of natural tea component are generally appreciated and natural teas having such features are not only taken as a tea beverage by being brewed with hot water but also recently used in processed foods taking advantages of the features of tea, such as mousse and ice cream. However, natural tea easily deteriorates by the effect of a moisture content and oxidation and color, taste and flavor, scent, etc. of tea degrade. Such degradation occurs not only in dried tea but also in tea beverage and concentrated tea liquid, which are obtained by treating natural tea with hot water and stored. Furthermore, such degradation occurs when natural green tea is ground and the resultant powder is blended with water and a fat and oil and used in processed food etc. as a paste-state tea. Separately from these, when a liquid-state tea beverage and a concentrated tea liquid are stored, chlorophyll, catechinic acid, vitamin C and unsaturated fatty acid are oxidized by the effect of dissolved oxygen in the liquid, with the result that the color of a tea beverage changes (to brown) and the taste and flavor thereof reduces in some cases. Because of this, when a tea beverage and a concentrated tea liquid are stored, a large amount of vitamin C must be added and storage temperature, etc. must be considered. In the case where a paste-state tea to be used in processed foods is stored, it is considered to mix a liquid-state fat and oil to powdered green tea, as described, for example, in Japanese Patent Laid-Open No. 7-079702. However, in this case, another problem newly occurs in that taste and flavor is reduced by oxidation of the fat and oil added. In contrast, in the store method of the embodiment, since oxidation of these products by oxygen is suppressed without fail, compared to conventional methods, taste and flavor and color tone of liquid-state tea or paste-state tea are satisfactorily maintained for a long term.

EXAMPLES

The present invention will be more specifically described by use of Examples and Comparative Examples, below; however, the present invention is not limited by these. Unless otherwise specified, NMR measurement was performed at room temperature. In Examples and Comparative Examples, physical property values were obtained by the following measurement methods and measurement apparatuses.

(Method for Measuring Glass Transition Temperature)

Glass transition temperature was measured in accordance with JIS K7122. As a measurement apparatus, "DSC-60", manufactured by Shimadzu Corporation was used.

(Method for Measuring Melting Point)

As the melting point, a DSC melting point peak temperature was measured in accordance with ISO11357. As a measurement apparatus, "DSC-60", manufactured by Shimadzu Corporation was used.

(Method for Determining Weight Average Molecular Weight and Number Average Molecular Weight)

The weight average molecular weight and number average molecular weight were measured by GPC-LALLS. As a measurement apparatus, "HLC-8320GPC", manufactured by Tosoh Corporation was used.

Synthesis Example 1 of Monomer

Synthesis Example 1-1

To an autoclave of 18 L (inner volume), dimethyl naphthalene-2,6-dicarboxylate (2.20 kg), 2-propanol (11.0 kg) and a catalyst (350 g containing 50 wt % of water) of 5% palladium immobilized on active carbon were supplied. Subsequently, the air within the autoclave was replaced with nitrogen and the nitrogen was further replaced with hydrogen. Thereafter, hydrogen was supplied until the interior pressure of the autoclave reached 0.8 MPa. Next, a stirrer was driven and a rotation speed was adjusted to be 500 rpm. After the interior temperature was increased up to 100° C. over 30 minutes, hydrogen was further supplied to set a pressure at 1 MPa. After that, hydrogen was continuously supplied in accordance with a reduction of pressure with the progression of a reaction so as to maintain 1 MPa. Seven hours later, since pressure reduction was stopped, the autoclave was cooled and unreacted residual hydrogen was released, and then the reaction solution was taken out from the autoclave. After the reaction solution was filtered and the catalyst was removed, 2-propanol was distilled away from the separated filtrate by an evaporator. To the crude product obtained, 2-propanol (4.40 kg) was added. Dimethyl tetralin-2,6-dicarboxylate was purified by recrystallization in a yield of 80%. Note that NMR analysis results are as follows. $^1$H-NMR (400 MHz CDCl$_3$) δ7.76-7.96 (2H m), 7.15 (1H d), 3.89 (3H s), 3.70 (3H s), 2.70-3.09 (5H m), 1.80-1.95 (1H m).

Synthesis Example 1-2

To an autoclave of 18 L (inner volume), naphthalene-1,8-dicarboxylic acid anhydride (1.90 kg), ethyl acetate (10.0 kg) and a catalyst (300 g containing 50 wt % of water) of 5% palladium immobilized on active carbon were supplied. Subsequently, the air within the autoclave was replaced with nitrogen and the nitrogen was further replaced with hydrogen. Thereafter, hydrogen was supplied until the interior pressure of the autoclave reached 3.0 MPa. Next, a stirrer was driven and a rotation speed was adjusted to be 500 rpm. After the interior temperature was increased up to 80° C. over 30 minutes, hydrogen was continuously supplied in accordance with a reduction of pressure with the progression of a reaction so as to maintain 3.0 MPa. Three hours later, since pressure reduction was stopped, the autoclave was cooled and unreacted residual hydrogen was released, and then the reaction solution was taken out from the autoclave. After the reaction solution was filtered, ethanol (40.0 kg) was added to the residue (a mixture of a precipitated crude product and a catalyst) filtered out, and stirred at 75° C. After the crude product was dissolved, the ethanol solution was filtered to remove the catalyst. The reaction solution recovered and the ethanol solution were mixed and then ethyl acetate and ethanol were distilled away by an evaporator. The crude product obtained was washed with acetone to obtain tetralin-1,8-dicarboxylic acid in a yield of 51%. Note that NMR analysis results are as follows. $^1$H-NMR (400 MHz CD$_3$OD) δ 7.82 (1H d), 7.20-38 (2H m), 4.51-4.59 (1H m), 2.80-2.97 (2H m), 2.22-2.32 (1H m), 1.93-2.04 (1H m), 1.75-1.88 (2H m).

Subsequently, a 5 L flask was charged with the obtained tetralin-1,8-dicarboxylic acid (300 g), methanol (3.0 kg) and concentrated sulfuric acid (50 g). The mixture was refluxed at 65° C. for 35 hours to perform esterification. Thereafter, the reaction solution was neutralized with sodium hydrogen carbonate and the precipitated crude product was separated by filtration. To the crude product, 2-propanol was then added and the mixture was subjected to purification by recrystallization to obtain dimethyl tetralin-1,8-dicarboxylate in a yield of 86%. Note that NMR analysis results are as follows. $^1$H-NMR (400 MHz CDCl$_3$) δ 7.76-7.82 (1H d), 7.20-7.30 (2H m), 4.42-4.48 (1H m), 3.82 (3H s), 3.69 (3H s), 2.78-2.96 (2H m), 2.21-2.28 (1H m), 1.90-1.99 (1H m), 1.70-1.84 (2H m).

Production Example 1 of Polymer

Production Example 1-1

To a polyester resin manufacturing apparatus equipped with a packed tower system rectifier, a partial condenser, a total condenser, a cold trap, a stirrer, a heating unit and a nitrogen inlet tube, dimethyl tetralin-2,6-dicarboxylate (543 g) obtained in Synthesis Example 1-1, 1,4-butanediol (315 g) and tetrabutyl titanate (0.171 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (0.171 g) was added. The temperature was gradually increased and pressure was gradually decreased and then polycondensation was performed at 245° C. and 133 Pa or less to obtain a tetralin ring-containing polyester compound (1-1).

The weight average molecular weight and number average molecular weight of the obtained polyester compound (1-1) were determined by GPC (gel permeation chromatography). As a result, the polystyrene-equivalent weight average molecular weight was $8.7 \times 10^4$ and the number average molecular weight thereof was $3.1 \times 10^4$. The glass transition temperature and melting point were measured by DSC. As a result, the glass transition temperature was 36° C. and the melting point was 145° C.

Production Example 1-2

A tetralin ring-containing polyester compound (1-2) was synthesized in the same manner as in Production Example 1-1 except that ethylene glycol (217 g) was used in place of 1,4-butanediol of Production Example 1-1. The polystyrene-equivalent weight average molecular weight of the polyester compound (1-2) was $8.5 \times 10^4$ and the number average molecular weight thereof was $3.0 \times 10^4$. The glass transition Production Example 1-3

A tetralin ring-containing polyester compound (1-3) was synthesized in the same manner as in Production Example 1-1 except that 1,6-hexanediol (413 g) was used in place of 1,4-butanediol of Production Example 1-1. The polystyrene-equivalent weight average molecular weight of the polyester compound (1-3) was $8.9\times10^4$ and the number average molecular weight thereof was $3.3\times10^4$. The glass transition temperature was 16° C. and the melting point was 137° C.

Production Example 1-4

A tetralin ring containing polyester compound (1-4) containing ethylene glycol and 1,4-butanediol in a molar ratio of 10:90 was synthesized in the same manner as in Production Example 1-1 except that the starting amount of 1,4-butanediol of Production Example 1-1 was changed to 227 g and further ethylene glycol (52 g) was used. The polystyrene-equivalent weight average molecular weight of the polyester compound (1-4) was $1.1\times10^5$ and the number average molecular weight thereof was $4.0\times10^4$. The glass transition temperature was 38° C. and the meeting point was 135° C.

Production Example 1-5

A tetralin ring-containing polyester compound (1-5) was synthesized in the same manner as in Production Example 1-1 except that dimethyl tetralin-1,8-dicarboxylate obtained in Synthesis Example 1-2 was used in place of dimethyl tetralin-2,6-dicarboxylate of Production Example 1-1. The polystyrene-equivalent weight average molecular weight of the polyester compound (1-5) was $8.3\times10^4$ and the number average molecular weight thereof was $2.8\times10^4$. The glass transition temperature was 35° C. and the melting point was not determined because of amorphous crystal.

Example 1-1

With a polyester compound (1-1) (100 parts by mass), cobalt stearate (II) (0.02 parts by mass in terms of cobalt) was dry-blended. The obtained oxygen-absorbing resin composition was formed into a film by use of a double-screw extruder having two screws of 20 mm in diameter at an extrusion temperature of 220° C., a screw rotation number of 60 rpm, a feed screw rotation number of 16 rpm and a haul-off speed of 1.3 m/min. In this manner, an oxygen-absorbing film having a width of 130 mm and a thickness of 95 to 105 μm was manufactured.

Next, two gas barrier bags formed of an aluminum foil laminate film were prepared. Two test pieces (100 mm in length×100 mm in width) of the obtained oxygen-absorbing film were put in the two gas barrier bags together with 500 cc of air. The relative humidity in one of the bags was adjusted to be 100%; whereas the relative humidity of the other bag was adjusted to be 30% and then the bags were separately sealed. The sealed bags thus obtained were stored at 40° C. for 14 days. The total amount of oxygen absorbed during this period was measured. Similarly, sealed bags were manufactured so as to have a relative humidity of 100% and stored at 40° C. and under a relative humidity of 100% for one month. The appearance of the film after the storage of one month was visually checked and odor after the bag was opened was checked. These results are shown in Table 1.

Example 1-2

An oxygen-absorbing film was manufactured in the same manner as in Example 1-1 except that a polyester compound (1-2) was used in place of the polyester compound (1-1). The amount of oxygen absorbed of the film was measured; appearance of the film was visually observed; and odor was checked. These results are shown in Table 1.

Example 1-3

An oxygen-absorbing film was manufactured in the same manner as in Example 1-1 except that a polyester compound (1-3) was used in place of the polyester compound (1-1). The amount of oxygen absorbed of the film was measured; appearance of the film was visually evaluated; and odor was checked. These results are shown in Table 1.

Example 1-4

An oxygen-absorbing film was manufactured in the same manner as in Example 1-1 except that a polyester compound (1-4) was used in place of the polyester compound (1-1). The amount of oxygen absorbed of the film was measured; appearance of the film was visually evaluated; and odor was checked. These results are shown in Table 1.

Example 1-5

An oxygen-absorbing film was manufactured in the same manner as in Example 1-1 except that a polyester compound (1-5) was used in place of the polyester compound (1-1). The amount of oxygen absorbed of the film was measured; appearance of the film was visually evaluated; and odor was checked. These results are shown in Table 1.

Comparative Example 1-1

An oxygen-absorbing film was manufactured in the same manner as in Example 1-1 except that N-MXD6 (trade name: MX nylon S6011, manufactured by Mitsubishi Gas Chemical Company Inc.) was used in place of the polyester compound (1-1). The amount of oxygen absorbed of the film was measured, appearance of the film was visually observed, and odor was checked. These results are shown in Table 1.

TABLE 1

| | Resin used in oxygen-absorbing resin composition | Amount of oxygen absorbed[1] | | Appearance[2] | Odor[2] |
|---|---|---|---|---|---|
| | | Humidity 30% | Humidity 100% | | |
| Example 1-1 | Polyester compound (1-1) | 21 cc | 17 cc | Shape was maintained | None |
| Example 1-2 | Polyester compound (1-2) | 14 cc | 20 cc | Shape was maintained | None |
| Example 1-3 | Polyester compound (1-3) | 27 cc | 32 cc | Shape was maintained | None |

TABLE 1-continued

| | Resin used in oxygen-absorbing resin composition | Amount of oxygen absorbed[1] | | Appearance[2] | Odor[2] |
|---|---|---|---|---|---|
| | | Humidity 30% | Humidity 100% | | |
| Example 1-4 | Polyester compound (1-4) | 20 cc | 18 cc | Shape was maintained | None |
| Example 1-5 | Polyester compound (1-5) | 22 cc | 20 cc | Shape was maintained | None |
| Comparative Example 1-1 | N-MXD6 | 10 cc | 2 cc | Collapsed | None |

[1]Total amount of oxygen absorbed during 14 days from initiation of test
[2]Evaluated after one-month storage at 40° C. and a humidity of 100%

As is apparent from Table 1, the oxygen-absorbing resin compositions of the present invention delivered satisfactory oxygen-absorbing performance both in high humidity and low humidity conditions and the shapes of films were maintained even after absorption of oxygen without collapse and no odor was sensed.

Production Example 2 of Polymer

Production Example 2-1

To a polyester resin manufacturing apparatus equipped with a packed tower system rectifier, a partial condenser, a total condenser, a cold trap, a stirrer, a heating unit and a nitrogen inlet tube, dimethyl tetralin-2,6-dicarboxylate (543 g) obtained in Synthesis Example 1-1, 1,4-butanediol (315 g) and tetrabutyl titanate (0.050 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (0.050 g) was added. The temperature was gradually increased and pressure was gradually decreased and then polycondensation was performed at 250° C. and 133 Pa or less to obtain a tetralin ring-containing polyester compound (2-1).

The weight average molecular weight and number average molecular weight of the obtained polyester compound (2-1) were determined by GPC (gel permeation chromatography). As a result, the polystyrene-equivalent weight average molecular weight was $8.7 \times 10^4$ and the number average molecular weight thereof was $3.1 \times 10^4$. The glass transition temperature and melting point were measured by DSC. As a result, the glass transition temperature was 36° C. and the melting point was 145° C.

Production Example 2-2

To a polyester resin manufacturing apparatus used in Production Example 2-1, dimethyl tetralin-2,6-dicarboxylate (543 g) obtained in Synthesis Example 1-1, ethylene glycol (217 g), magnesium acetate tetra hydrates (0.268 g) and calcium acetate mono hydrate (0.085 g) were supplied. The temperature of the mixture was raised up to 230° C. under a nitrogen atmosphere to perform a transesterification reaction. After the reaction conversion rate of the dicarboxylate component reached 90% or more, triethyl phosphate (0.080 g) and antimony trioxide (0.108 g) were added. The temperature was gradually increased and pressure was gradually decreased and then polycondensation was performed at 250° C. and 133 Pa or less to obtain a tetralin ring-containing polyester compound (2-2). The polystyrene-equivalent weight average molecular weight of the polyester compound (2-2) was $8.5 \times 10^4$ and the number average molecular weight thereof was $3.0 \times 10^4$. The glass transition temperature was 68° C. and the melting point was not determined because of amorphous crystal.

Production Example 2-3

A tetralin ring-containing polyester compound (2-3) was synthesized in the same manner as in Production Example 2-1 except that 1,6-hexanediol (413 g) was used in place of 1,4-butanediol of Production Example 2-1. The weight average molecular weight of the polyester compound (2-3) was $8.9 \times 10^4$ and the number average molecular weight thereof was $3.3 \times 10^4$. The glass transition temperature was 16° C. and the melting point was 137° C.

Production Example 2-4

To a polyester resin manufacturing apparatus used in Production Example 2-1, dimethyl tetralin-2,6-dicarboxylate (554 g) obtained in Synthesis Example 1-1, ethylene glycol (52 g), 1,4-butanediol (227 g) and tetrabutyl titanate (0.050 g) were supplied. The temperature of the mixture was raised up to 220° C. under a nitrogen atmosphere to perform a transesterification reaction. After the reaction conversion rate of the dicarboxylate component reached 85% or more, tetrabutyl titanate (0.050 g) was added. The temperature was gradually increased and pressure was gradually decreased and then polycondensation was performed at 250° C. and 133 Pa or less to obtain a tetralin ring-containing polyester compound (2-4) containing ethylene glycol and 1,4-butanediol in a molar ratio of 10:90. The polystyrene-equivalent weight average molecular weight of the polyester compound (2-4) was $1.1 \times 10^5$ and the number average molecular weight thereof was $4.0 \times 10^4$. The glass transition temperature was 38° C. and the melting point was 135° C.

(Method for Evaluating Film Thickness Deviation)

Film thickness was measured at 5 points, the following value was obtained in accordance with the expression: [(maximum film thickness value−minimum film thickness value)/average thickness value]×100

If the value was 0 or more to less than 10, thickness deviation was evaluated as good, 10 or more to 20 or less as fair and beyond 20 as poor.

Example 2-1

A polyester compound (2-1) (30 parts by mass), cobalt stearate (II) (0.02 parts by mass in terms of cobalt) and a polyolefin resin (product name: "UMERIT 4040F", manufactured by UBE-MARUZEN POLYETHYLENE Co., Ltd., MFR: 4.0 g/10 minutes (measured in accordance with JIS K7210), MFR at 240° C.: 7.9 g/10 minutes, MFR at 250° C.: 8.7 g/10 minutes (hereinafter referred to also as "LLDPE") (70 parts by weight) were dry-blended. The obtained oxygen-absorbing resin composition 2-1 was supplied to a double-screw extruder having two screws of 37 mm in diameter, at a rate of 15 kg/h and formed into a film by melting and kneading at a cylinder temperature of 240° C. In this manner, a single-layer oxygen-absorbing film formed of the oxygen-absorbing resin composition and having a thickness of 50 μm was manufactured. The appearance of the film was satisfactory and the film thickness deviation was evaluated as "good".

Next, two gas barrier bags formed of an aluminum foil laminate film were prepared. Two test pieces (10 cm in length×10 cm in width) of the obtained oxygen-absorbing film were put in the two gas barrier bags together with 500 cc of air. The relative humidity of one of the bags was adjusted to be 100%; whereas the relative humidity of the other bag was adjusted to be 30% and then the bags were separately sealed. The sealed bags thus obtained were stored at 40° C. for 7 days. The total amount of oxygen absorbed during this period was measured. These results are shown in Table 2.

Example (2-2

An oxygen-absorbing film was manufactured in the same manner as in Example 2-1 except that the starting amount of polyester compound (2-1) was changed to 20 parts by mass and the starting amount of polyolefin resin was changed to 80 parts by mass. Observation of appearance of the film, evaluation of thickness deviation and measurement of the amount of oxygen absorbed were performed. These results are shown in Table 2.

Example 2-3

An oxygen-absorbing film was manufactured in the same manner as in Example 2-1 except that the starting amount of polyester compound (2-1) was changed to 50 parts by mass and the starting amount of polyolefin resin was changed to 50 parts by mass. Observation of appearance of the film, evaluation of thickness deviation and measurement of the amount of oxygen absorbed were performed. These results are shown in Table 2.

Example 2-4

An oxygen-absorbing film was manufactured in the same manner as in Example 2-1 except that a polyester compound (2-2) was used in place of the polyester compound (2-1). Observation of appearance of the film, evaluation of thickness deviation and measurement of the amount of oxygen absorbed were performed. These results are shown in Table 2.

Example 2-5

An oxygen-absorbing film was manufactured in the same manner as in Example 2-1 except that a polyester compound (2-3) was used in place of the polyester compound (2-1). Observation of appearance of the film, evaluation of thickness deviation and measurement of the amount of oxygen absorbed were performed. These results are shown in Table 2.

Example 2-6

An oxygen-absorbing film was manufactured in the same manner as in Example 2-1 except that a polyester compound (2-4) was used in place of the polyester compound (2-1). Observation of appearance of the film, evaluation of thickness deviation and measurement of the amount of oxygen absorbed were performed. These results are shown in Table 2.

Example 2-7

An oxygen-absorbing film was manufactured in the same manner as in Example 2-1 except that the starting amount of polyester compound (2-1) was changed to 80 parts by mass and the starting amount of polyolefin resin was changed to 20 parts by mass. Observation of appearance of the film, evaluation of thickness deviation and measurement of the amount of oxygen absorbed were performed. These results are shown in Table 2.

Example 2-8

An oxygen-absorbing film was manufactured in the same manner as in Example 2-1 except that the starting amount of polyester compound (2-1) was changed to 10 parts by mass and the starting amount of polyolefin resin was changed to 90 parts by mass. Observation of appearance of the film, evaluation of thickness deviation and measurement of the amount of oxygen absorbed were performed. These results are shown in Table 2.

TABLE 2

| | Oxygen-absorbing resin composition | | | | Film | |
|---|---|---|---|---|---|---|
| | | | | | Amount of oxygen absorbed[3] | |
| | Polyester compound | Melting/ kneading ratio[1] | Appearance | Thickness deviation [2] | Humidity 100% | Humidity 30% |
| Example 2-1 | Polyester compound (2-1) | 30:70 | Satisfactory | good | 15 cc | 14 cc |
| Example 2-2 | Polyester compound (2-1) | 50:50 | Satisfactory | good | 20 cc | 18 cc |
| Example 2-3 | Polyester compound (2-1) | 20:80 | Satisfactory | good | 12 cc | 11 cc |
| Example 2-4 | Polyester compound (2-2) | 30:70 | Satisfactory | good | 8 cc | 10 cc |
| Example 2-5 | Polyester compound (2-3) | 30:70 | Satisfactory | good | 14 cc | 15 cc |

TABLE 2-continued

| | Oxygen-absorbing resin composition | | | Film | | |
|---|---|---|---|---|---|---|
| | | | | | Amount of oxygen absorbed[3] | |
| | Polyester compound | Melting/ kneading ratio[1] | Appearance | Thickness deviation [2] | Humidity 100% | Humidity 30% |
| Example 2-6 | Polyester compound (2-4) | 30:70 | Satisfactory | good | 16 cc | 16 cc |
| Example 2-7 | Polyester compound (2-1) | 80:20 | Slightly unsatisfactory | fair | 15 cc | 14 cc |
| Example 2-8 | Polyester compound (2-1) | 10:90 | Satisfactory | good | 3 cc | 2 cc |

[1] Mass ratio of polyester compound: polyolefin resin
[2] If the value computationally obtained in accordance with [(maximum film thickness value − minimum film thickness value)/average thickness value] × 100 is 0 or more to less than 10, thickness deviation was evaluated as good, 10 or more to 20 or less as fair and beyond 20 as poor.
[3] The total amount of oxygen absorbed during 7 days from initiation of test As is apparent from Table 2, the oxygen-absorbing resin compositions of the present invention delivered satisfactory oxygen-absorbing performance under both high humidity and low humidity conditions.

Example 2-9

Using a multilayer film manufacturing apparatus equipped with two extruders, a feed block, a T die, a cooling roll, a corona discharge unit, a winder, etc., LLDPE was extruded from a first extruder and the oxygen-absorbing resin composition 2-1 obtained in Example 2-1 was extruded from a second extruder to manufacture a three-layer film 2-1 (thickness: 10 μm/20 μm/10 μm) of 800 mm in width formed of two types of materials (having a core layer formed of oxygen-absorbing resin composition 2-1 and the two skin layers formed of LLDPE and respectively arranged on both surface sides of the core layer). Thereafter, one of the surfaces of the film was treated with corona discharge at a rate of 60 m/minute. The appearance of the obtained film was satisfactory and HAZE was 25%.

Next, an oxygen-absorbing multilayer film, which was constituted of PET (product name: "E5100", manufactured by Toyobo Co., Ltd., 12 μm)/adhesive (3 μm)/aluminum foil (9 μm)/adhesive (3 μm)/nylon 6 film A (product name: "N1202", manufactured by Toyobo Co., Ltd., 15 μm)/adhesive (3 μm)/LLDPE (10 μm)/oxygen-absorbing resin composition 2-1 (20 μm)/LLDPE (10 μm), was obtained by using a urethane dry-lamination adhesive (product name: "AD817/CAT-RT86L-60", manufactured by Toyo-Morton, Ltd.) as the adhesive to be applied to the corona treated surface in accordance with dry lamination. Note that the numeric character within parentheses refers to the thickness (unit: μm) of each layer. The same description is employed in the following Examples, unless otherwise specified.

Next, a three-side sealed bag of 3 cm×3 cm was manufactured from the obtained oxygen-absorbing multilayer film and filled with vitamin C powder having a water activity of 0.35 (10 g) and then sealed. The sealed bag thus obtained was stored at 23° C. for one month. After storage for one month, the oxygen concentration in the bag was measured and appearance of the vitamin C powder was visually observed. As a result, the oxygen concentration in the bag was 0.1 vol % or less and the color tone of the vitamin C powder was satisfactorily maintained.

Example 2-10

An oxygen-absorbing multilayer paper base material, which was constituted of a bleached craft paper (basis weight: 340 g/m²)/urethane dry-lamination adhesive (product name: "AD817/CAT-RT86L-60", manufactured by Toyo-Morton, Ltd., 3 μm)/alumina vapor deposition PET film (product name: "GL-AEH", manufactured by Toppan Printing Co., Ltd., 12 μm)/urethane anchor coating agent ("EL-557A/B", manufactured by Toyo-Morton, Ltd., 0.5 μm)/low-density polyethylene (product name: "Mirason 18SP", manufactured by Mitsui Chemicals Inc., 20 μm)/LLDPE (10 μm)/oxygen-absorbing resin composition 2-1 (20 μm)/LLDPE (10 μm), was obtained by using the three-layer film 2-1 formed of two types of materials and manufactured in Example 2-9, in accordance with extrusion lamination.

The obtained oxygen-absorbing multilayer paper base material was molded into a 1-liter gable-top paper container. The moldability of the container was satisfactory. The paper container was filled with Japanese sake and then sealed. The sealed container thus obtained was stored at 23° C. for one month. After storage for one month, the oxygen concentration in the paper container was 0.1 vol % or less and the taste and flavor of the Japanese sake was satisfactorily maintained.

Example 2-11

Oxygen-absorbing resin composition 2-2 was obtained in the same manner as in Example 2-1 except that an ethylene-propylene block copolymer (product name: "NOVATEC FG3DC", manufactured by Japan Polypropylene Corporation, MFR at 230° C.: 9.5 g/10 minutes, MFR at 240° C.: 10.6 g/10 minutes (hereinafter referred to also as "PP-1") was used in place of LLDPE.

Subsequently, three-layer film 2-2 (thickness: 15 μm/30 μm/15 μm) formed of two types of materials was manufactured in the same manner as in Example 2-9 except that oxygen-absorbing resin composition 2-2 was used as a core layer and PP-1 was used as the skin layer in place of LLDPE. Appearance of the obtained film was satisfactory and HAZE was 64%.

Next, an oxygen-absorbing multilayer film, which was constituted of alumina vapor deposition PET (product name:

"GL-AEH", manufactured by Toppan Printing Co., Ltd., 12 μm)/adhesive (3 μm)/nylon 6 film A (product name: "N1202", manufactured by Toyobo Co., Ltd., 15 μm)/adhesive (3 μm)/PP-1 (15 μm)/oxygen-absorbing resin composition 2-2 (30 μm)/PP-1 (15 μm), was obtained by use of a urethane dry-lamination adhesive (product name: "AD817/CAT-RT86L-60", manufactured by Toyo-Morton, Ltd.) as the adhesive to be applied to the corona treated surface, in accordance with dry lamination.

A three-side sealed bag of 10 cm×20 cm was manufactured by use of the obtained oxygen-absorbing multilayer film and a circular fumarole (through-hole) of 2 mm in diameter was provided in a part of the three-side sealed bag and the fumarole was temporally sealed with a label. The three-side sealed bag was filled with cream stew containing carrot and meat and then sealed. The sealed container thus obtained (pouch with a fumarole) was transparent and thus the stew within the bag was able to be visually observed. The sealed container was sterilized by heating at 124° C. for 30 minutes in accordance with retort treatment. After the retort treatment, the sealed container was stored at 23° C. for one month. After storage for one month, the bag was directly heated by a microwave oven. It was confirmed that the bag was swollen about 3 minutes later and the label temporally sealed was peeled off and vapor came out from the fumarole. After completion of heat treatment, the color tone of carrot and the taste and flavor of the cream stew were checked. As a result, the appearance of the carrot was satisfactorily maintained and the taste and flavor of the cream stew was satisfactory.

Comparative Example 2-1

An iron powder having an average particle diameter of 20 μm and calcium chloride were mixed in a mass ratio of 100:1. The mixture and LLDPE were kneaded in a weight ratio of 30:70 to obtain iron based oxygen-absorbing resin composition 2-3. We tried to manufacture a three-layer film formed of two types of materials in the same manner as in Example 2-9 except that iron based oxygen-absorbing resin composition 2-3 was used as a core layer; however, a film having smooth surface that can be sufficiently subjected to further studies could not be obtained since convexoconcave portions were produced in the surface of the obtained film due to iron powder. Because of this, on the LLDPE film of 40 μm in thickness, a film of iron based oxygen-absorbing resin composition 2-3 of 20 μm in thickness was stacked in accordance with extrusion lamination as an oxygen-absorbing layer to manufacture a laminate film constituted of iron based oxygen-absorbing resin composition 2-3 (20 μm)/LLDPE (40 μm). Thereafter, the surface of the oxygen-absorbing layer was treated with corona discharge.

Next, an oxygen-absorbing multilayer paper base material, which was constituted of a bleached craft paper (basis weight: 340 g/m²)/urethane dry-lamination adhesive (product name: "AD817/CAT-RT86L-60", manufactured by Toyo-Morton, Ltd., 3 μm)/alumina vapor deposition PET film (product name: "GL-AEH", manufactured by Toppan Printing Co., Ltd., 12 μm)/urethane anchor coating agent ("EL-557A/B", manufactured by Toyo-Morton, Ltd., 0.5 μm)/low-density polyethylene (product name: "Mirason 18SP", manufactured by Mitsui Chemicals Inc., 20 μm)/iron based oxygen-absorbing resin composition 2-3 (20 μm)/LLDPE (40 μm), was obtained in the same manner as in Example 2-10 except that the laminate film obtained above was used, in accordance with extrusion lamination.

We tried to manufacture a 1-liter gable-top paper container from the obtained oxygen-absorbing multilayer paper base material in the same manner as in Example 2-10; however, it was difficult to form corners of the paper container. Then, we tried to manufacture a paper container by lowering a speed of manufacturing a container. As a result, the paper container was finally obtained with a large number of defective products (that were eliminated). Using the obtained paper container, a storage test of Japanese sake was performed in the same manner as in Example 2-10. After one month, the container was opened. As a result, aldehyde odor generated and the taste and flavor significantly reduced.

Comparative Example 2-2

Iron based oxygen-absorbing resin composition 2-4 was obtained in the same manner as in Comparative Example 2-1 except that PP-1 was used in place of LLDPE. Then, a laminate film of iron based oxygen-absorbing resin composition 2-4 (20 μm)/PP-1 (40 μm) was manufactured in the same manner as in Comparative Example 2-1 except that iron based oxygen-absorbing resin composition 2-4 was used in place of iron based oxygen-absorbing resin composition 2-3 and PP-1 was used in place of LLDPE. Thereafter, the surface of the oxygen-absorbing layer was treated with corona discharge.

Next, an oxygen-absorbing multilayer film, which was constituted of alumina vapor deposition PET (product name: "GL-AEH", manufactured by Toppan Printing Co., Ltd., 12 μm)/adhesive (3 μm)/nylon 6 film A (product name: "N1202", manufactured by Toyobo Co., Ltd., 15 μm)/adhesive (3 μm)/iron based oxygen-absorbing resin composition 2-4 (20 μm)/PP-1 (40 μm), was obtained in the same manner as in Example 2-11 except that the laminate film obtained above was used, in accordance with dry lamination.

A three-side sealed bag of having a fumarole was manufactured by use of the obtained oxygen-absorbing multilayer film in the same manner as in Example 2-11 and subjected to the same test as in Example 2-11. As a result, the taste and flavor of cream stew was satisfactorily maintained; however, the film was opaque so that the content could not be visually observed from the outside. In addition, during microwave heating, air bubbles were partly generated in the surface of the three-side sealed bag.

As is apparent from Examples 2-9 to 2-11, it was confirmed that the oxygen-absorbing resin composition of the present invention is excellent in processability to a paper container and storage property of an alcohol beverage, and a satisfactory storage container even if a fumarole for microwave cooking was provided. In addition, it was confirmed that the composition is excellent also in transparency (visibility of a content) and the color tone etc. of the content can be checked from the outside.

Example 3-1

With polyester compound (1-1) (100 parts by mass), cobalt stearate (II) (0.02 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition.

Subsequently, using a multilayer sheet manufacturing apparatus equipped with three extruders, a feed block, a T die, a cooling roll, a winder, etc., polyethylene terephthalate (trade name: Unipet RT553C, (hereinafter referred to also as "PET") manufactured by Japan Unipet) was extruded from first and third extruders, whereas the oxygen-absorbing resin composition obtained above was extruded from a second extruder and passed through the feed block to manufacture a multilayer sheet of a three-layer structure using two types of materials, i.e., constituted of PET (100 μm)/an oxygen-absorbing resin composition (300 μm)/PET (100 μm).

Subsequently, the oxygen transmission coefficient of the obtained multilayer sheet was measured at 23° C., under atmospheres having a relative humidity 60% and a relative humidity 90%. The oxygen transmission coefficient 30 days after initiation of measurement is shown in Table 3. Note that oxygen transmission coefficient was measured by use of an oxygen transmission rate measurement apparatus (trade name: OX-TRAN 2-61 manufactured by MOCON). The lower the measurement value, the more satisfactory the oxygen barrier property. After measurement of the oxygen transmission coefficient, odor of the multilayer sheet was checked. The results are shown in Table 3.

Example 3-2

A multilayer sheet was manufactured in the same manner as in Example 3-1 except that a polyester compound (1-2) was used in place of the polyester compound (1-1). The oxygen transmission coefficient of the multilayer sheet was measured and odor was checked in the same manner as in Example 3-1. The evaluation results are shown in Table 3.

Example 3-3

A multilayer sheet was manufactured in the same manner as in Example 3-1 except that a polyester compound (1-3) was used in place of the polyester compound (1-1). The oxygen transmission coefficient of the multilayer sheet was measured and odor was checked in the same manner as in Example 3-1. The evaluation results are shown in Table 3.

Comparative Example 3-1

A single-layer sheet of 500 μm in thickness was manufactured by use of polyethylene terephthalate (trade name: Unipet RT553C manufactured by Japan Unipet). The oxygen transmission coefficient of the multilayer sheet was measured and odor was checked in the same manner as in Example 3-1. The evaluation results are shown in Table 3.

TABLE 3

| | Resin used in oxygen-absorbing resin composition | Oxygen transmission coefficient/30th day (cc · mm/m² · day · atm) | |
|---|---|---|---|
| | | Relative humidity 60% | Relative humidity 90% |
| Example 3-1 | Polyester compound (1-1) | 0.045 | 0.048 |
| Example 3-2 | Polyester compound (1-2) | 0.055 | 0.052 |
| Example 3-3 | Polyester compound (1-3) | 0.043 | 0.043 |
| Comparative Example 3-1 | (Polyethylene terephthalate single-layer sheet) | 3.8 | 3.8 |

As is apparent from Table 3, it was confirmed that the multilayer sheets of Examples 3-1 to 3-3, since oxygen is satisfactorily absorbed by an oxygen-absorbing layer, are low in oxygen transmission coefficient and excellent in oxygen barrier property both under high humidity or low humidity conditions, compared to Comparative Example 3-1.

Example 4-1

With polyester compound (1-1) (100 parts by mass), cobalt stearate (II) (0.05 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition. Subsequently, a film of 200 mm in width and 50 μm in thickness was manufactured by use of the obtained oxygen-absorbing resin composition and by means of a single screw extruder equipped with a T die and having a screw of 25 mm in diameter. Both surfaces of the obtained film were treated with corona discharge to manufacture an oxygen-absorbing film.

Next, using a urethane dry-lamination adhesive (trade name: AD-817/CAT-RT86L-60 manufactured by Toyo Ink Co., Ltd.), an alumina vapor deposition PET film (trade name: GL-ARH-F, manufactured by Toppan Printing Co., Ltd.) and a linear low-density polyethylene film (trade name: Tohcello T. U. X HC (hereinafter referred to also as "LLDPE") manufactured by Tohcello Inc.) were laminated in accordance with dry lamination to obtain an oxygen-absorbing multilayer film, i.e., constituted of the alumina vapor deposition PET film (12 μm)/adhesive (3 μm)/oxygen-absorbing resin composition (50 μm)/adhesive (3 μm)/LLDPE (30 μm).

A three-side sealed bag of 10 cm×10 cm was manufactured from the obtained oxygen-absorbing multilayer film such that the LLDPE layer faced inside. The three-side sealed bag was filled with powder seasoning "instant bouillon" (50 g) having a water activity of 0.35 and then sealed. The sealed bag thus obtained was stored at 40° C. under a condition of 50% RH. The oxygen concentration in the bag was measured after storage of 14 days and storage of 2 months. The sealed bag after 2 month storage was opened, and the taste and flavor of the powder seasoning was checked. These results are shown in Table 4.

Example 4-2

An oxygen-absorbing resin composition, an oxygen-absorbing multilayer film and a three-side sealed bag were manufactured in the same manner as in Example 4-1 except that a polyester compound (1-2) was used in place of the polyester compound (1-1), and oxygen concentration measurement and a storage test were performed in the same manner as in Example 4-1. These results are shown in Table 4.

Example 4-3

An oxygen-absorbing resin composition, an oxygen-absorbing multilayer film and a three-side sealed bag were manufactured in the same manner as in Example 4-1 except that a polyester compound (1-3) was used in place of the polyester compound (1-1), and oxygen concentration measurement and a storage test were performed in the same manner as in Example 4-1. These results are shown in Table 4.

Comparative Example 4-1)

A multilayer film was manufactured in the same manner as in Example 4-1 except that cobalt stearate (II) was not added. Thereafter, a three-side sealed bag was manufactured and oxygen concentration measurement and a storage test were performed in the same manner as in Example 4-1. These results are shown in Table 4.

Comparative Example 4-2

An oxygen-absorbing resin composition and an oxygen-absorbing multilayer film were manufactured in the same manner as in Example 4-1 except that N-MXD6 (trade name: MX nylon 56011, manufactured by Mitsubishi Gas Chemical Company Inc.) was used in place of the polyester compound (1-1). Thereafter a three-side sealed bag was manufactured. Oxygen concentration measurement and a storage test were performed in the same manner as in Example 4-1. These results are shown in Table 4.

TABLE 4

| | Resin used in oxygen-absorbing resin composition | Transition metal | Oxygen concentration (vol %) | | Taste and Flavor after 2 months |
|---|---|---|---|---|---|
| | | | After 14 days | After 2 months | |
| Example 4-1 | Polyester compound (1-1) | Cobalt[1] 0.05 parts by mass | 4.1 | 0.1 or less | Satisfactory |
| Example 4-2 | Polyester compound (1-2) | Cobalt[1] 0.05 parts by mass | 4.8 | 0.1 or less | Satisfactory |
| Example 4-3 | Polyester compound (1-3) | Cobalt[1] 0.05 parts by mass | 3.2 | 0.1 or less | Satisfactory |
| Comparative Example 4-1 | Polyester compound (1-1) | None | 20.1 | 16.9 | Reduced |
| Comparative Example 4-2 | N-MXD6 | Cobalt[1] 0.05 parts by mass | 20.3 | 17.2 | Reduced |

[1]Cobalt stearate is used

As is apparent from Table 4, it was confirmed that the oxygen-absorbing multilayer bodies of Examples 4-1 to 4-3 deliver satisfactory oxygen-absorbing performance under low humidity conditions and the taste and flavor of the content is satisfactorily maintained.

Example 4-4

Using a multilayer sheet manufacturing apparatus equipped with four extruders, a feed block, a T die, a cooling roll, a winder, etc., a polypropylene (trade name: NOVATEC PPFY6 (hereinafter referred to also as "PP-2") manufactured by Japan Polypropylene Corporation) was extruded from a first extruder; an adhesive resin (trade name: MODIC F532, manufactured by Mitsubishi Chemical Corporation) was extruded from a second extruder; the oxygen-absorbing resin composition obtained in Example 41 was extruded from a third extruder; and an ethylene-vinyl alcohol copolymer (trade name: EVAL F101B (hereinafter referred to also as "EVOH") manufactured by Kuraray Co., Ltd.) was extruded from a fourth extruder and passed through the feed block to manufacture an oxygen-absorbing multilayer sheet having a seven-layer structure formed of four types of materials, i.e., constituted of PP-2 (100 µm)/adhesive resin (15 µm)/oxygen-absorbing resin composition (100 µm)/adhesive resin (15 µm)/EVOH (30 µm)/adhesive resin (15 µm)/PP-2 (250 µm).

Subsequently, the obtained oxygen-absorbing multilayer sheet was formed into a cup-form container (inner volume: 100 cc, surface area: 96 cm$^2$) by use of a vacuum molding machine in accordance with hot molding such that the inner layer (PP-2 of 100 µm) of the multilayer sheet faced inside. The container thus obtained was filled with fruits dipped in syrup containing mandarin orange (40 g) and fruit syrup liquid (40 g) and the opening was sealed with a top film. The top film used herein was a gas barrier film (constituted of silica vapor deposition PET film (12 µm)/adhesive (3 µm)/nylon 6 film A (15 µm)/adhesive (3 µm)/non-stretched polypropylene film (50 µm)), which was manufactured by stacking a silica vapor deposition PET film (trade name: TECHBARRIER TXR, manufactured by Mitsubishi Plastics Inc.,), nylon 6 film A (trade name: N1202, manufactured by Toyobo Co., Ltd.) and a non-stretched polypropylene film (trade name: aroma-ET, manufactured by OKAMOTO) in accordance with dry lamination with the application of a urethane dry-lamination adhesive (trade name: A-525/A-532, manufactured by Mitsui Chemicals Inc.). The sealed container filled with the fruit syrup was sterilized by boiling at 90° C. and then stored under conditions of 40° C. and 90% RH. The oxygen concentration in the container was measured after storage of 14 days and storage of 2 months. The sealed container after 2 month storage was opened the color tone of the mandarin orange was checked. These results are shown in Table 5.

Example 4-5

An oxygen-absorbing resin composition, an oxygen-absorbing multilayer sheet and a cup-form container were manufactured in the same manner as in Example 4-4 except that a polyester compound (1-2) was used in place of the polyester compound (1-1), and oxygen concentration measurement and a storage test were performed in the same manner as in Example 4-4. These results are shown in Table 5.

Example 4-6

An oxygen-absorbing resin composition, an oxygen-absorbing multilayer sheet and a cup-form container were manufactured in the same manner as in Example 4-4 except that a polyester compound (1-3) was used in place of the polyester compound (1-1), and oxygen concentration measurement and a storage test were performed in the same manner as in Example 4-4. These results are shown in Table 5.

Comparative Example 4-3

A multilayer sheet and a cup-form container were manufactured in the same manner as in Example 4-4 except that the oxygen-absorbing resin composition was not used and an oxygen absorbing layer was not formed. Oxygen concentration measurement and a storage test were performed in the same manner as in Example 4-4. These results are shown in Table 5.

TABLE 5

| | Resin used in oxygen-absorbing resin composition | Transition metal | Oxygen concentration (vol %) | | Color tone after 2 months |
|---|---|---|---|---|---|
| | | | After 14 days | After 2 months | |
| Example 4-4 | Polyester compound (1-1) | Cobalt[1] 0.05 parts by mass | 0.9 | 0.1 or less | Satisfactory |
| Example 4-5 | Polyester compound (1-2) | Cobalt[1] 0.05 parts by mass | 1.5 | 0.1 or less | Satisfactory |
| Example 4-6 | Polyester compound (1-3) | Cobalt[1] 0.05 parts by mass | 0.8 | 0.1 or less | Satisfactory |
| Comparative Example 4-3 | None | — | 20.0 | 19.9 | Reduced |

[1]Cobalt stearate is used

As is apparent from Table 5, it was confirmed that the oxygen-absorbing multilayer bodies of Examples 4-4 to 4-6 deliver satisfactory oxygen-absorbing performance under high humidity conditions and the color tone of the content is satisfactorily maintained.

Production Example of Polymer

Production Example 5-1

To a polyester resin manufacturing apparatus equipped with a packed tower system rectifier, a partial condenser, a total condenser, a cold trap, a stirrer, a heating unit and a nitrogen inlet tube, dimethyl tetralin-2,6-dicarboxylate (543 g) obtained in Synthesis Example 1-1, 1,4-butanediol (315 g) and tetrabutyl titanate (0.050 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (0.050 g) was added. The temperature was gradually increased and pressure was gradually decreased and then polycondensation was performed at 250° C. and 133 Pa or less to obtain a tetralin ring-containing polyester compound (5-1).

The weight average molecular weight and number average molecular weight of the obtained polyester compound (5-1) were determined by GPC (gel permeation chromatography). As a result, the polystyrene-equivalent weight average molecular weight was $8.7 \times 10^4$ and the number average molecular weight thereof was $3.1 \times 10^4$. The glass transition temperature and melting point were measured by DSC. As a result, the glass transition temperature was 36° C. and the melting point was 145° C.

Production Example 5-2

In the same manner as in Production Example 5-1, dimethyl tetralin-2,6-dicarboxylate (543 g), ethylene glycol (217 g), magnesium acetate tetrahydrate (0.268 g) and calcium acetate mono hydrate (0.085 g) were supplied and a transesterification reaction was performed under a nitrogen atmosphere by increasing the temperature of the mixture up to 230° C. After the reaction conversion rate of the dicarboxylate component reached 90% or more, triethyl phosphate (0.080 g) and antimony trioxide (0.108 g) were added. The temperature was gradually increased and pressure was gradually decreased and then polycondensation was performed at 250° C. and 133 Pa or less to obtain a tetralin ring-containing polyester compound (5-2). The polystyrene-equivalent weight average molecular weight of the obtained polyester compound (5-2) was $8.5 \times 10^4$ and the number average molecular weight thereof was $3.1 \times 10^4$. The glass transition temperature was 68° C. and the melting point was not determined because of amorphous crystal.

Production Example 5-3

A tetralin ring-containing polyester compound (5-3) was synthesized in the same manner as in Production Example 5-1 except that 1,6-hexanediol (413 g) was used in place of 1,4-butanediol of Production Example 5-1. The weight average molecular weight of the obtained polyester compound (5-3) was $8.9 \times 10^4$ and the number average molecular weight thereof was $3.3 \times 10^4$. The glass transition temperature was 16° C. and the melting point was 137° C.

Production Example 5-4

In the same manner as in Production Example 5-1, dimethyl tetralin-2,6-dicarboxylate (554 g), ethylene glycol (52 g), 1,4-butanediol (227 g) and tetrabutyl titanate (0.050 g) were supplied. The temperature of the mixture was raised up to 220° C. under a nitrogen atmosphere and a transesterification reaction was performed. After the reaction conversion rate of the dicarboxylate component reached 85% or more, tetrabutyl titanate (0.050 g) was added. The temperature was gradually increased and pressure was gradually decreased and polycondensation was performed at 250° C. and 133 Pa or less to obtain a tetralin ring-containing polyester compound (5-4) containing ethylene glycol and 1,4-butanediol in a molar ratio of 10:90. The polystyrene-equivalent weight average molecular weight of the obtained polyester compound (5-4) was $1.1 \times 10^5$ and the number average molecular weight thereof was $4.0 \times 10^4$. The glass transition temperature was 38° C. and the melting point was 135° C.

Example 5-1

A polyester compound (5-1) (30 parts by mass), cobalt stearate (II) (0.02 parts by mass in terms of cobalt) and a polyolefin resin (product name: "UMERIT 4040F", manufactured by UBE-MARUZEN POLYETHYLENE, MFR: 4.0 g/10 minutes (measured in accordance with JIS K7210), MFR at 240° C.: 7.9 g/10 minutes, MFR at 250° C.: 8.7 g/10 minutes (hereinafter referred to also as "LLDPE 1")) (70 parts by weight) were dry-blended to obtain oxygen-absorbing resin composition 5-1.

Subsequently, using a multilayer film manufacturing apparatus equipped with two extruders, a feed block, a T die, a cooling roll, a corona discharge apparatus, a winder, etc., oxygen-absorbing resin composition 5-1 was extruded from a first extruder and a linear low-density polyethylene (product name: "NOVATEC LLUF641", manufactured by Japan Polyethylene Corporation, MFR: 2.1 g/10 minutes (measured in accordance with JIS K7210), MFR at 240° C.: 4.4 g/10 minutes, MFR at 250° C.: 5.2 g/10 minutes, (hereinafter referred to also as "LLDPE2")) was extruded from a second extruder to manufacture a two-layer film formed of two types of materials (thickness: oxygen-absorbing layer 20 μm/sealant layer 20 μm) of 800 mm in width, i.e., constituted of an oxygen-absorbing layer formed of the oxygen-absorbing resin composition 5-1 and a sealant layer formed of LLDPE 2. Thereafter, the surface of the oxygen-absorbing layer was treated with corona discharge at a rate of 100 m/minute to manufacture a film roll (original roll). When the obtained film roll was observed, thickness deviation such as bumps was not seen. When the obtained film was observed, the appearance of the film was satisfactory and a HAZE of the film was 20%.

Next, nylon 6 film A (product name: "N1202", manufactured by Toyobo Co., Ltd.), an aluminum foil and a PET film (product name: "E5102", manufactured by Toyobo Co., Ltd.) were stacked in accordance with dry lamination with the application of a urethane dry-lamination adhesive (product name: "TM-320/CAT-13B", manufactured by Toyo-Morton, Ltd.) to the corona treated surface to obtain an oxygen-absorbing multilayer film constituted of the PET film (12 µm)/adhesive (3 µm)/aluminum foil (9 µm)/adhesive (3 µm)/nylon 6 film A (15 µm)/adhesive (3 µm)/oxygen-absorbing resin composition 5-1 (20 µm)/LLDPE2 (20 µm).

A three-side sealed bag of 15 cm×20 cm was manufactured from the obtained oxygen-absorbing multilayer film such that the LLDPE 2 layer faced inside. The three-side sealed bag was filled with powder seasoning "instant bouillon" (200 g) having a water activity of 0.35 and then sealed. The sealed bag thus obtained was stored at 23° C. The oxygen concentration in the bag was measured after storage of 7 days and storage of one month. The sealed bag after one month storage was opened and the taste and flavor of the powder seasoning was checked. These results are shown in Table 6.

Example 5-2

A film roll and an oxygen-absorbing multilayer film were obtained in the same manner as in Example 5-1 except that the starting amount of polyester compound (5-1) was changed to 20 parts by mass and the starting amount of polyolefin resin was changed to 80 parts by mass. Thereafter, a three-side sealed bag was manufactured in the same manner as in Example 5-1 and the concentration of oxygen in the bag was measured and a storage test was performed in the same manner as in Example 5-1. These results are shown in Table 6.

Example 5-3

A film roll and an oxygen-absorbing multilayer film were obtained in the same manner as in Example 5-1 except that the starting amount of polyester compound (5-1) was changed to 50 parts by mass and the starting amount of polyolefin resin was changed to 50 parts by mass. Thereafter, a three-side sealed bag was manufactured in the same manner as in Example 5-1 and the concentration of oxygen in the bag was measured and a storage test was performed in the same manner as in Example 5-1. These results are shown in Table 6.

Example 5-4

A film roll and an oxygen-absorbing multilayer film were obtained in the same manner as in Example 5-1 except that a polyester compound (5-2) was used in place of the polyester compound (5-1). Thereafter, a three-side sealed bag was manufactured in the same manner as in Example 5-1 and the concentration of oxygen in the bag was measured and a storage test was performed in the same manner as in Example 5-1. These results are shown in Table 6.

Example 5-5

A film roll and an oxygen-absorbing multilayer film were obtained in the same manner as in Example 5-1 except that a polyester compound (5-3) was used in place of the polyester compound (5-1). Thereafter, a three-side sealed bag was manufactured in the same manner as in Example 5-1 and the concentration of oxygen in the bag was measured and a storage test was performed in the same manner as in Example 5-1. These results are shown in Table 6.

Example 5-6

A film roll and an oxygen-absorbing multilayer film were obtained in the same manner as in Example 5-1 except that a polyester compound (5-4) was used in place of the polyester compound (5-1). Thereafter, a three-side sealed bag was manufactured and the concentration of oxygen in the bag was measured and a storage test was performed. These results are shown in Table 6.

Example 5-7

A film roll and an oxygen-absorbing multilayer film were obtained in the same manner as in Example 5-1 except that the starting amount of polyester compound (5-1) was changed to 80 parts by mass and the starting amount of polyolefin resin was changed to 20 parts by mass. Thereafter, a three-side sealed bag was manufactured in the same manner as in Example 5-1 and the concentration of oxygen in the bag was measured and a storage test was performed in the same manner as in Example 5-1. These results are shown in Table 6.

TABLE 6

|  | Oxygen-absorbing resin composition | | | Oxygen concentration (vol %) | | Taste and flavor after one month |
|---|---|---|---|---|---|---|
|  | Polyester compound | Melting/ kneading ratio[1)] | Film-roll appearance | After 7 day | After one month |  |
| Example 5-1 | Polyester compound (5-1) | 30:70 | Satisfactory | 0.7 | 0.1 or less | Satisfactory |
| Example 5-2 | Polyester compound (5-1) | 50:50 | Satisfactory | 0.4 | 0.1 or less | Satisfactory |
| Example 5-3 | Polyester compound (5-1) | 20:80 | Satisfactory | 1.3 | 0.1 or less | Satisfactory |

TABLE 6-continued

| | Oxygen-absorbing resin composition | | | Oxygen concentration (vol %) | | |
| --- | --- | --- | --- | --- | --- | --- |
| | Polyester compound | Melting/ kneading ratio[1] | Film-roll appearance | After 7 day | After one month | Taste and flavor after one month |
| Example 5-4 | Polyester compound (5-2) | 30:70 | Satisfactory | 2.5 | 0.1 or less | Almost satisfactory |
| Example 5-5 | Polyester compound (5-3) | 30:70 | Satisfactory | 0.5 | 0.1 or less | Satisfactory |
| Example 5-6 | Polyester compound (5-4) | 30:70 | Satisfactory | 0.3 | 0.1 or less | Satisfactory |
| Example 5-7 | Polyester compound (5-1) | 80:20 | Slightly unsatisfactory | 0.8 | 0.1 or less | Satisfactory |

[1]Mass ratio of polyester compound: polyolefin resin

As is apparent from Table 6, the oxygen-absorbing multilayer bodies of Examples 5-1 to 5-7 delivered satisfactory oxygen-absorbing performance under low humidity conditions.

Example 5-8

Using a multilayer sheet manufacturing apparatus equipped with three extruders, a feed block, a T die, a cooling roll, a corona discharge apparatus, a winder, etc., LLDPE2 was extruded from first and third extruders and oxygen-absorbing resin composition 5-1 was extruded from a second extruder to manufacture a three-layer film formed of two types of materials (thickness: skin layer 10 µm/core layer 20 µm/skin layer 10 µm) of 800 mm in width, i.e., constituted of a core layer formed of oxygen-absorbing resin composition 5-1 and skin layers formed of LLDPE2 on both sides of the core layer. Thereafter, one of the surfaces thereof was treated with corona discharge at a rate of 120 m/minute. The appearance of the obtained film was satisfactory and a HAZE of the film was 25%.

An oxygen-absorbing multilayer film, which was constituted of a PET (product name: "E5100", manufactured by Toyobo Co., Ltd., 12 µm)/adhesive (3 µm)/aluminum foil (9 µm)/adhesive (3 µm)/nylon 6 film A (product name: "N1202", manufactured by Toyobo Co., Ltd., 15 µm)/adhesive (3 µm)/LLDPE2 (10 µm)/oxygen-absorbing resin composition 5-1 (20 µm)/LLDPE2 (10 µm), was obtained in accordance with dry lamination with the application of a urethane dry-lamination adhesive (product name: "AD817/CAT-RT86L-60", manufactured by Toyo-Morton, Ltd.) to the corona treated surface.

A self-supporting bag (standing pouch of 130 mm in side×175 mm in length×35 mm in bottom gore) with an open top was fabricated from the obtained oxygen-absorbing multilayer film, more specifically, by joining two side films and a single bottom-surface film by heat sealing such that the LLDPE 2 layer faces inside. As a result, the processability of the bag was satisfactory.

Next, the self-supporting bag was filled with cucumber (150 g) and 150 g of an acetic acid solution (acetic acid concentration: 10 mass %) at a rate of 40 bags/minute and then the top opening of the self-supporting bag was sealed by heat sealing. The degree of opening of the self-supporting bag was satisfactory and had no adverse effect on filling operation. Furthermore, the heat sealing of the opening of the self-supporting bag was performed without any problem. Subsequently, 100 sealed bags thus obtained were subjected to boiling treatment performed at 90° C. for 30 minutes and then stored at 23° C. After storage for one month, the color tone of cucumber in the self-supporting bags and the appearance of the self-supporting bags were observed. Furthermore, the sealed bags were opened and the taste and flavor of cucumber was checked. Since the sealed bags were transparent, cucumber was able to be visually observed from the outside of the bag without opening it. The color tone of cucumber was satisfactorily maintained and no abnormality was found in the appearance of the bags. The taste and flavor of cucumber was satisfactory.

Comparative Example 5-1

Iron powder having an average particle diameter of 20 µm and calcium chloride were mixed in a mass ratio of 100:1. The mixture and LLDPE 1 were kneaded in a mass ratio of 30:70 to obtain iron-based oxygen-absorbing resin composition 5-A. We tried to manufacture a three-layer film formed of two types of materials in the same manner as in Example 5-8 except that iron-based oxygen-absorbing resin composition 5-A was used as a core layer. However, convexoconcave portions due to iron powder were produced in the surface of the obtained film. Thus, a film having smooth surface that can be sufficiently subjected to further studies could not be obtained.

Comparative Example 5-2

To a linear low-density polyethylene film of 40 µm in thickness (product name: "Tohcello T. U. X HC", manufactured by Tohcello, Inc. (hereinafter referred to as "LLDPE3")), a film of iron-based oxygen-absorbing resin composition 5-A of 20 µm in thickness serving as an oxygen-absorbing layer was stacked in accordance with extrusion lamination to manufacture a laminate film constituted of iron-based oxygen-absorbing resin composition 5-A (20 µm)/LLDPE3 (40 µm). Thereafter, the oxygen-absorbing layer surface was treated with corona discharge.

An iron-based oxygen-absorbing multilayer film, which was constituted of PET (product name: "E5100", manufactured by Toyobo Co., Ltd., 12 µm)/adhesive (3 µm)/aluminum foil (9 µm)/adhesive (3 µm)/nylon 6 film A (15 µm)/adhesive (3 µm)/iron-based oxygen-absorbing resin 5-A (20 µm)/LLDPE3 (40 µm), was manufactured in the same manner as in Example 5-8 except that the laminate film obtained above was used in place of the three-layer film formed of two types of materials in Example 5-8. Thereafter, the multilayer film was processed into a self-supporting bag in the same manner as in Example 5-8.

Next, we tried to fill the self-supporting bag with cucumber (150 g) and 150 g of an acetic acid solution (acetic acid concentration: 10 mass %) in the same manner as in Example 5-8. However, since the degree of opening of the self-supporting bag was unsatisfactory, the content spilled out and filling could not successfully be made. Such a defective product was frequently produced and the rate of defective products reached 30%. Self-supporting bags successfully filled were sealed, boiled and stored in the same manner as in Example 5-8, and thereafter appearance observation and a storage test were performed. Since the sealed bag was opaque, cucumber could not be visually observed from the outside of the bag. When the bag was opened and the state of cucumber was evaluated, the taste and flavor and color tone of cucumber were satisfactorily maintained; however, convexoconcave portions were observed in the appearance of the bag and delamination partly occurred.

Example 5-9

A three-layer film formed of two types of materials was manufactured in the same manner as in Example 5-8. Using this, a low-density polyethylene (product name: "Mirason 18SP", manufactured by Mitsui Chemicals Inc.) was stacked in accordance with extrusion lamination to obtain an oxygen-absorbing multilayer paper base material, i.e., constituted of a bleached craft paper (basis weight: 340 g/m$^2$)/urethane dry-lamination adhesive (product name: "AD817/CAT-RT86L-60", manufactured by Toyo-Morton, Ltd., 3 μm)/alumina vapor deposition PET film (product name: "GL-AEH", manufactured by Toppan Printing Co., Ltd., 12 μm)/urethane anchor coating agent ("EL-557A/B", manufactured by Toyo-Morton, Ltd., 0.5 μm)/low-density polyethylene (20 μm)/LLDPE2 (10 μm)/oxygen-absorbing resin composition 5-1 (20 μm)/LLDPE2 (10 μm).

The oxygen-absorbing multilayer paper base material thus obtained was molded into a 1-liter gable-top paper container. The moldability of the container was satisfactory. The paper container was filled with Japanese sake and then sealed. The sealed container thus obtained was stored at 23° C. for one month. After storage for one month, the oxygen concentration in the paper container was 0.1 vol % or less and the taste and flavor of the Japanese sake was satisfactorily maintained.

Example 5-10

Oxygen-absorbing resin composition 5-2 was obtained in the same manner as in Example 5-1 except that an ethylene-propylene random copolymer (product name: "NOVATEC PP FW4BT", manufactured by Japan Polypropylene Corporation, MFR at 230° C.: 6.5 g/10 minutes, MFR at 240° C.: 8.3 g/10 minutes (hereinafter referred to also as "PP-3")) was used in place of LLDPE 1. Subsequently, oxygen-absorbing resin composition 5-2 was extruded from a first extruder and an olefin based polymer alloy (product name: "VMX X270F", manufactured by Mitsubishi Chemical Corporation, MFR at 190° C.: 6.5 g/10 minutes) was extruded from a second extruder in the same manner as in Example 5-1 to manufacture a two-layer film formed of two types of materials, i.e., constituted by laminating the oxygen-absorbing layer (30 μm) formed of oxygen-absorbing resin composition 5-2 and a sealant layer (30 μm) formed of the olefin-based polymer alloy. Thereafter, corona discharge treatment was performed in the same manner.

Subsequently, an ethylene-vinyl alcohol copolymer film (product name: "EVAL F104B", manufactured by Kuraray Co., Ltd.) (15 μm) and a nylon 6 film B (product name: "N1202", manufactured by Toyobo Co., Ltd.) layer (15 μm) were stacked in accordance with dry lamination with the application of a urethane dry-lamination adhesive to the corona treated surface to obtain an oxygen-absorbing multilayer film, i.e., constituted of nylon 6 film B (15 μm)/adhesive for lamination (3 μm)/ethylene-vinyl alcohol copolymer film (15 μm)/adhesive for lamination (3 μm)/oxygen-absorbing resin composition 5-2 (30 μm)/olefin-based polymer alloy (30 μm). The appearance of the obtained oxygen-absorbing multilayer film was satisfactory.

Separately from this, using an ethylene-propylene random copolymer (product name: "NOVATEC PP EG7F", manufactured by Japan Polypropylene Corporation, MFR 1.3 g/10 minutes (measured in accordance with JIS K7210), MFR at 240° C.: 8.2 g/10 minutes, MFR at 250° C.: 9.8 g/10 minutes (hereinafter referred to also as "PP-4")), a multilayer sheet, which was constituted of PP-4 (400 μm)/maleic anhydride modified polypropylene (product name: "ADMER QF500", manufactured by Mitsui Chemicals Inc., 15 μm)/ethylene-vinyl alcohol copolymer A (product name: "EVAL L104B", manufactured by Kuraray Co., Ltd., 40 μm)/maleic anhydride modified polypropylene (product name: the same as above, 15 μm)/PP-4 (400 μm), was manufactured and this was drawn at a drawing ratio of 2.5 and molded into a 70 cc cup.

The cup was filled up with orange jelly and sealed with the oxygen-absorbing multilayer film, which was manufactured as mentioned above such that the nylon 6 film B layer faced outside and used as a cover. In the sealed container thus obtained, the color tone of the content was able to be visually observed through the cover. Subsequently, the sealed container was subjected to heat treatment performed at 85° C. for 30 minutes and then stored at 23° C. for one month. After storage of one month, the container was opened. As a result, the openability was satisfactory without forming a double cover. The taste and flavor and color tone of the content were satisfactorily maintained.

Example 5-11

The oxygen-absorbing multilayer film obtained in the same manner as in Example 5-10 and a 70 cc cup were sterilized with hydrogen peroxide by soaking. No abnormality was found in the oxygen-absorbing multilayer film at the time of sterilization.

Subsequently, the cup was filled with hot orange jam maintained at a temperature of 80° C. and sealed with the oxygen-absorbing multilayer film used as a cover such that the nylon 6 film B layer faces outside. The sealed container thus obtained was stored at 23° C. for one month. After storage for one month, the content was visually observed through the cover. As a result, the color tone of the content was satisfactorily maintained. When the sealed container was opened, openability was satisfactory without forming a double cover. The taste and flavor of the content was satisfactorily maintained.

Comparative Example 5-3

When the laminate film having iron-based oxygen-absorbing resin composition 5-A obtained in the same manner as in Comparative Example 5-2 was sterilized with hydrogen peroxide in the same manner as in Example 5-11, air bubbles were generated in hydrogen peroxide and sterilization was not able to continue.

From the foregoing, it was demonstrated that the oxygen-absorbing multilayer bodies and containers of Examples 5-8 to 5-11 are excellent in oxygen-absorbing performance, processability and strength. In addition, it was confirmed that they can be treated with heat and can be used for food etc. which cannot be stored by an iron-based oxygen-absorbing multilayer body using an iron-based oxygen-absorbing resin composition and can be sterilized with hydrogen peroxide. Besides this, since they also have excellent visibility of a content and the color tone etc. of the content can be checked from the outside, it was confirmed that they can be suitably used for container covers requiring such performance.

Example 5-12

Using a multilayer sheet molding apparatus for forming a six-layer film of four types of materials, equipped with first to fourth extruders, a feed block, a T die, a cooling roll and a sheet winder, PP2 was extruded from the first extruder; oxygen-absorbing resin composition 5-1 from the second extruder; ethylene-vinyl alcohol copolymer B (product name: "EVAL L 171B", manufactured by Kuraray Co., Ltd.) from the third extruder; and a polypropylene adhesive resin (product name: "MODIC AP P604V", manufactured by Mitsubishi Chemical Corporation) from the fourth extruder to obtain an oxygen-absorbing multilayer sheet. The multilayer sheet was constituted of PP2 (80 µm)/oxygen-absorbing resin composition 5-1 (100 µm)/adhesion layer (15 µm)/ethylene-vinyl alcohol copolymer B (30 µm)/adhesion layer (15 µm)/PP2 (250 µm) in the order from the inside. Furthermore, the oxygen-absorbing multilayer sheet obtained by the coextrusion above had satisfactory appearance without thickness deviation etc.

Subsequently, the obtained oxygen-absorbing multilayer sheet was processed by thermoforming by use of a vacuum molding machine into a tray-form container (inner volume: 350 cc, surface area 200 cm$^2$) with an open top such that the inner layer (PP2 of 80 µm) faced inside. The obtained oxygen-absorbing multilayer container had satisfactory appearance without thickness variation etc. The container was sterilized by UV irradiation. In the container sterilized, aseptic steamed rice (200 g) was placed immediately upon cooking and the inner atmosphere of the container was replaced with nitrogen gas to control the oxygen concentration to be 0.5 vol %.

Separately from this, a PET film, an MXD6 multilayer coextrusion nylon film (product name: "SUPERNYL SP-R", manufactured by Mitsubishi Plastics Inc.) and a non-stretched polypropylene film (product name: "aroma-UT21", manufactured by OKAMOTO) were laminated in accordance with dry lamination with the application of an adhesive for lamination to manufacture a multilayer film, which was constituted of a gas barrier film (PET film (12 µm)/adhesive for lamination (3 µm)/MXD6 multilayer coextrusion nylon film (15 µm)/adhesive for lamination (3 µm)/ non-stretched polypropylene film (60 µm). Then, the multilayer film was sterilized with UV irradiation in the same manner as in the above container. Thereafter, the container was sealed with the multilayer film used as a top film and stored under the conditions of 23° C. and 50% RH. The oxygen concentration in the container was measured after 3 months from initiation of storage. After 3 month storage, the container was opened and the taste and flavor of the steamed rice and the strength of the oxygen-absorbing multilayer container were checked. These results are shown in Table 7.

Example 5-13

An oxygen-absorbing resin composition was obtained in the same manner as in Example 5-1 except that the starting amount of polyester compound (5-1) was changed to 20 parts by mass and the starting amount of polyolefin resin was changed to 80 parts by mass. Then, an oxygen-absorbing multilayer sheet and a tray-form container were manufactured in the same manner as in Example 5-12 except that the oxygen-absorbing resin composition was used. Measurement of oxygen concentration in the container, determination of strength and a storage test were performed in the same manner as in Example 5-12. These results are shown in Table 7.

Example 5-14

An oxygen-absorbing resin composition was obtained in the same manner as in Example 5-1 except that the starting amount of polyester compound (5-1) was changed to 50 parts by mass and the starting amount of polyolefin resin was changed to 50 parts by mass. Then, an oxygen-absorbing multilayer sheet and a tray-form container were manufactured in the same manner as in Example 5-12 except that the oxygen-absorbing resin composition was used. Measurement of oxygen concentration in the container, determination of strength and a storage test were performed in the same manner as in Example 5-12. These results are shown in Table 7.

Example 5-15

An oxygen-absorbing resin composition was obtained in the same manner as in Example 5-1 except that a polyester compound (5-2) was used in place of the polyester compound (5-1). Then, an oxygen-absorbing multilayer sheet and a tray-form container were manufactured in the same manner as in Example 5-12 except that the oxygen-absorbing resin composition was used. Measurement of oxygen concentration in the container, determination of strength and a storage test were performed in the same manner as in Example 5-12. These results are shown in Table 7.

Example 5-16

An oxygen-absorbing resin composition was obtained in the same manner as in Example 5-1 except that a polyester compound (5-3) was used in place of the polyester compound (5-1). Then, an oxygen-absorbing multilayer sheet and a tray-form container were manufactured in the same manner as in Example 5-12 except that the oxygen-absorbing resin composition was used. Measurement of oxygen concentration in the container, determination of strength and a storage test were performed in the same manner as in Example 5-12. These results are shown in Table 7.

Example 5-17

An oxygen-absorbing resin composition was obtained in the same manner as in Example 5-1 except that a polyester compound (5-4) was used in place of the polyester compound (5-1). Then, an oxygen-absorbing multilayer sheet and a tray-form container were manufactured in the same manner as in Example 5-12 except that the oxygen-absorbing resin composition was used. Measurement of oxygen concentration in the container, determination of strength and a storage test were performed in the same manner as in Example 5-12. These results are shown in Table 7.

Comparative Example 5-4

Iron powder having an average particle diameter of 20 μm and calcium chloride were mixed in a mass ratio of 100:1. The mixture and LLDPE 1 were kneaded in a mass ratio of 30:70 to obtain iron-based oxygen-absorbing resin composition B. Subsequently, an iron-based oxygen-absorbing multilayer sheet was manufactured in the same manner as in Example 5-12 except that the iron-based oxygen-absorbing resin composition B was used in place of oxygen-absorbing resin composition 5-1. The multilayer sheet was constituted of PP2 (80 μm)/iron-based oxygen-absorbing resin composition B (100 μm)/adhesion layer (15 μm)/ethylene-vinyl alcohol copolymer B (30 μm)/adhesion layer (15 μm)/PP2 (250 μm) in the order from the inside.

We tried to mold the obtained iron-based oxygen-absorbing multilayer sheet into a tray-form container by thermoforming in the same manner as in Example 5-12. However, it was difficult to process it since draw down occurred. The container thus manufactured was opaque since it contained iron powder. In addition, because of the presence of convexoconcave portions in the film surface due to the iron powder, appearance was unsatisfactory. Measurement of oxygen concentration in the container and determination of strength and a storage test were performed in the same manner as in Example 5-12 by use of containers having a barely acceptable appearance (just satisfy acceptable appearance). The results are shown in Table 7.

was dry-blended. The obtained mixture was supplied to a double-screw extruder having two screws of 37 mm in diameter, at a rate of 15 kg/h and melt-kneading was performed at a cylinder temperature of 240° C. and a strand was extruded from an extruder head. After cooling, the strand was pelletized to obtain oxygen-absorbing resin composition 6-1.

Subsequently, using a coextrusion apparatus equipped with first to third extruders, a feed block, a T die, a cooling roll and a winder, a low-density polyethylene (trade name: NOVATEC LD LC602A, manufactured by Japan Polyethylene Corporation (hereinafter referred to also as "LDPE")) was extruded from the first extruder, oxygen-absorbing resin composition 6-1 from the second extruder, and adhesive polyethylene (trade name: MODIC A515, manufactured by Mitsubishi Chemical Corporation, (hereinafter referred to also as "adhesive PE")) from the third extruder and passed through the feed block to manufacture an oxygen-absorbing multilayer film constituted of five layers of three types of materials and having a width of 800 mm, i.e., constituted of LDPE layer/adhesive PE layer/oxygen-absorbing layer/adhesive PE layer/LDPE layer. Thereafter, one of the surfaces of the multilayer film was treated with corona discharge at a rate of 60 m/minute.

Next, on the corona treated surface of the obtained oxygen-absorbing multilayer film, a multilayer paper base material was stacked by extrusion lamination of LDPE to obtain an oxygen-absorbing paper base material multilayer body (oxygen-absorbing multilayer body), which was constituted of a bleached craft paper (basis weight: 330 g/m²)/urethane dry-lamination adhesive (trade name: TM-250HV/CAT-RT86L-60, manufactured by Toyo-Morton, Ltd., 3 μm)/alumina vapor deposition PET film (trade name: GL-

TABLE 7

| | Oxygen-absorbing resin composition | | | | | Oxygen | |
| | | Melting/ kneading | Oxygen-absorbing container | | | concentration in container | Taste and flavor |
| | Polyester compound | ratio[1] | Moldability | Transparency | Strength | (vol %) | of steamed rice |
| Example 5-12 | Polyester compound (5-1) | 30:70 | Satisfactory | Satisfactory | Satisfactory | 0.1 or less | Satisfactory |
| Example 5-13 | Polyester compound (5-1) | 20:80 | Satisfactory | Satisfactory | Satisfactory | 0.1 or less | Satisfactory |
| Example 5-14 | Polyester compound (5-1) | 50:50 | Almost satisfactory | Almost satisfactory | Satisfactory | 0.1 or less | Satisfactory |
| Example 5-15 | Polyester compound (5-2) | 30:70 | Satisfactory | Satisfactory | Satisfactory | 0.1 or less | Satisfactory |
| Example 5-16 | Polyester compound (5-3) | 30:70 | Satisfactory | Satisfactory | Satisfactory | 0.1 or less | Satisfactory |
| Example 5-17 | Polyester compound (5-4) | 30:70 | Satisfactory | Satisfactory | Satisfactory | 0.1 or less | Satisfactory |
| Comparative Example 5-4 | | —[2] | Unsatisfactory | None | Satisfactory | 0.1 or less | Satisfactory |

[1]Mass ratio of polyester compound: polyolefin resin
[2]Iron based oxygen-absorbing resin composition B was used as an oxygen-absorbing resin composition As is apparent from Table 7, it was confirmed that the oxygen-absorbing multilayer containers of Examples 5-12 to 5-17 deliver satisfactory moldability and oxygen-absorbing performance and are transparent, and that strength of the containers can be maintained after absorption of oxygen.

Example 6-1

With a polyester compound (1-1) (100 parts by mass), cobalt stearate (II) (0.02 parts by mass in terms of cobalt)

AEH, manufactured by Toppan Printing Co., Ltd., 12 μm)/urethane anchor coating agent (trade name: EL-557A/B, manufactured by Toyo-Morton, Ltd., 0.5 μm)/LDPE (15 μm)/LDPE (15 μm/adhesive PE (10 μm)/oxygen-absorbing layer (20 μm/adhesive PE (10 μm)/LDPE (20 μm). The multilayer body was manufactured into a carton to obtain gable-top oxygen-absorbing paper container 6-1 (1000 mL) having a bottom of 7 cm squares. The moldability and processability of the paper container were satisfactory, in other words, the carton was easily manufactured.

Oxygen-absorbing paper container 6-1 was filled with 1000 mL of wine such that the amount of air in the head space was 20 cc, and then, the upper inner surfaces (LDPE) of the gable-top paper container were mutually sealed by heat sealing. The sealed paper container thus obtained was stored at 35° C. for one month. After storage for one month, the oxygen concentration (head-space oxygen concentration) in the paper container was measured and the taste and flavor of the wine was checked. Furthermore, the heat sealing strength of the upper portion of the gable-top paper container after one month storage was measured. These results are shown in Table 8.

Example 6-2

An oxygen-absorbing resin composition, an oxygen-absorbing multilayer film and a paper container were manufactured in the same manner as in Example 6-1 except that a polyester compound (1-2) was used in place of the polyester compound (1-1). Thereafter, the head-space oxygen concentration was measured, the taste and flavor of wine was checked and the heat sealing strength of upper portion of the paper container was measured in the same manner as in Example 6-1. These results are shown in Table 8.

Example 6-3

An oxygen-absorbing resin composition, an oxygen-absorbing multilayer film and a paper container were manufactured in the same manner as in Example 6-1 except that a polyester compound (1-3) was used in place of the polyester compound (1-1). Thereafter, the head-space oxygen concentration was measured, the taste and flavor of wine was checked and the heat sealing strength of upper portion of the paper container was measured in the same manner as in Example 6-1. These results are shown in Table 8.

Comparative Example 6-1

A single-layer film of LDPE (60 μm) was manufactured. An oxygen-absorbing multilayer film and a paper container were manufactured in the same manner as in Example 6-1 except that the single-layer film of LDPE was used in place of the oxygen-absorbing multilayer film constituted of five layers of three types of materials. Thereafter, the head-space oxygen concentration was measured, the taste and flavor of wine was checked and the heat sealing strength of upper portion of the paper container was measured in the same manner as in Example 6-1. These results are shown in Table 8.

Comparative Example 6-2

An oxygen-absorbing resin composition, an oxygen-absorbing multilayer film and a paper container were manufactured in the same manner as in Example 6-1 except that N-MXD6 (trade name: MX nylon 56011, manufactured by Mitsubishi Gas Chemical Company Inc.) was used in place of the polyester compound (1-1). Thereafter, the head-space oxygen concentration was measured, the taste and flavor of wine was checked and the heat sealing strength of the upper portion of the paper container was measured in the same manner as in Example 6-1. These results are shown in Table 8.

Comparative Example 6-3

Iron powder having an average particle diameter of 30 μm and calcium chloride were mixed in a mass ratio of 100:1. The mixture and LDPE were kneaded in a mass ratio of 30:70 to obtain an iron-based oxygen-absorbing resin composition 6-A. We tried to manufacture a five-layer film formed of three types of materials in the same manner as in Example 6-1 except that iron-based oxygen-absorbing resin composition 6-A was used in place of oxygen-absorbing resin composition 6-1; however, a film having smooth surface that can be sufficiently subjected to further studies was not able to be obtained because of the presence of convexoconcave portions produced in the surface of the film due to iron powder.

Comparative Example 6-4

On the LDPE film having a thickness 50 μm, a film (40 μm in thickness) of iron-based oxygen-absorbing resin composition 6-A obtained in Comparative Example 6-3 and serving as an oxygen-absorbing layer was stacked in accordance with extrusion lamination to manufacture a laminate film, which was constituted of iron-based oxygen-absorbing resin composition 6-A (40 μm)/LDPE (50 μm). Thereafter, the oxygen-absorbing layer surface was treated with corona discharge.

An oxygen-absorbing paper base material multilayer body, which was constituted of bleached craft paper (basis weight: 330 g/m$^2$)/urethane dry-lamination adhesive (3 μm)/alumina vapor deposition PET film (12 μm)/urethane anchor coating agent (0.5 μm)/LDPE (15 μm)/oxygen-absorbing layer (40 μm)/LDPE (50 μm), was manufactured by extrusion lamination of LDPE on a multilayer paper base material in the same manner as in Example 6-1 except that the laminate film obtained above was used in place of the oxygen-absorbing multilayer film constituted of five layers of three types of materials. Thereafter, we tried to manufacture a gable-top paper container from the multilayer body; however it was difficult to form the corners of the paper container. Then, we tried to manufacture a paper container by lowering a speed of manufacturing a container. As a result, the paper container was finally obtained with a large number of defective products (that were eliminated). Thereafter, the head-space oxygen concentration of the obtained paper container was measured, the taste and flavor of wine was checked and the heat sealing strength of the upper portion of the paper container was measured in the same manner as in Example 6-1. These results are shown in Table 8.

TABLE 8

| | | Oxygen concentration (vol %) | Taste and flavor | Strength of heat-sealing (kg) | |
|---|---|---|---|---|---|
| | Oxygen-absorbing layer | | | Before storage | After storage |
| Example 6-1 | Polyester (1-1) + cobalt stearate | 0.1 or less | Satisfactory | 3.9 | 3.8 |

TABLE 8-continued

|  | Oxygen-absorbing layer | Oxygen concentration (vol %) | Taste and flavor | Strength of heat-sealing (kg) Before storage | Strength of heat-sealing (kg) After storage |
|---|---|---|---|---|---|
| Example 6-2 | Polyester (1-2) + cobalt stearate | 0.1 or less | Satisfactory | 3.7 | 3.7 |
| Example 6-3 | Polyester (1-3) + cobalt stearate | 0.1 or less | Satisfactory | 3.7 | 3.5 |
| Comparative Example 6-1 | — | 13.3 | Reduced | 3.8 | 3.7 |
| Comparative Example 6-2 | N-MXD6 + cobalt stearate | 5.6 | Slightly Reduced | 3.7 | 0.9 |
| Comparative Example 6-4 | Iron-based oxygen-absorbing composition 6-A | 0.1 or less | Reduced[1] | 3.8 | 3.8 |

[1] having aldehyde odor

As is apparent from Table 8, it was confirmed that the paper containers of Examples 6-1 to 6-3 deliver satisfactory oxygen-absorbing performance, and that the taste and flavor of the content and container strength even after storage are maintained.

Production Example of Polymer

Production Example 7-1

To a polyester resin manufacturing apparatus equipped with a packed tower system rectifier, a partial condenser, a total condenser, a cold trap, a stirrer, a heating unit and a nitrogen inlet tube, dimethyl tetralin-2,6-dicarboxylate (543 g) obtained in Synthesis Example 1-1, 1,4-butanediol (315 g) and tetrabutyl titanate (0.050 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (0.050 g) was added. The temperature was gradually increased and pressure was gradually decreased and then polycondensation was performed at 245° C. and 133 Pa or less to obtain a tetralin ring-containing polyester compound (7-1).

The weight average molecular weight and number average molecular weight of the obtained polyester compound (7-1) were determined by GPC (gel permeation chromatography). As a result, the polystyrene-equivalent weight average molecular weight was $8.7 \times 10^4$ and the number average molecular weight thereof was $3.1 \times 10^4$. The glass transition temperature and melting point were measured by DSC. As a result, the glass transition temperature was 36° C. and the melting point was 145° C.

Production Example 7-2

In the same manner as in Production Example 7-1, dimethyl tetralin-2,6-dicarboxylate (543 g) obtained in Synthesis Example 1-1, ethylene glycol (217 g), magnesium acetate tetrahydrate (0.268 g) and calcium acetate mono hydrate (0.085 g) were supplied. The temperature of the mixture was raised up to 230° C. under a nitrogen atmosphere to perform a transesterification reaction. After the reaction conversion rate of the dicarboxylate component reached 90% or more, triethyl phosphate (0.080 g) and antimony trioxide (0.108 g) were added. The temperature was gradually increased and pressure was gradually decreased and then polycondensation was performed at 250° C. and 133 Pa or less to obtain a tetralin ring-containing polyester compound (7-2). The polystyrene-equivalent weight average molecular weight of the polyester compound (7-2) was $8.5 \times 10^4$ and the number average molecular weight thereof was $3.0 \times 10^4$. The glass transition temperature was 68° C. and the melting point was not determined because of amorphous crystal.

Production Example 7-3

A tetralin ring-containing polyester compound (7-3) was synthesized in the same manner as in Production Example 1 except that 1,6-hexanediol (413 g) was used in place of 1,4-butanediol of Production Example 7-1. The weight average molecular weight of the polyester compound (7-3) was $8.9 \times 10^4$ and the number average molecular weight thereof was $3.3 \times 10^4$. The glass transition temperature was 16° C. and the melting point was 137° C.

Production Example 7-4

In the same manner as in Production Example 7-1, dimethyl tetralin-2,6-dicarboxylate (554 g) obtained in Synthesis Example 1-1, ethylene glycol (44.3 g), 1,4-butanediol (258 g) and tetrabutyl titanate (0.050 g) were supplied. The temperature of the mixture was raised up to 220° C. under a nitrogen atmosphere and a transesterification reaction was performed. After the reaction conversion rate of the dicarboxylate component reached 85% or more, tetrabutyl titanate (0.050 g) was added. The temperature was gradually increased and pressure was gradually decreased and polycondensation was performed at 250° C. and 133 Pa or less to obtain a tetralin ring-containing polyester compound (7-4) containing ethylene glycol and 1,4-butanediol in a molar ratio of 8:92. The polystyrene-equivalent weight average molecular weight of the polyester compound (7-4) was $1.1 \times 10^5$ and the number average molecular weight thereof was $4.0 \times 10^4$. The glass transition temperature was 38° C. and the melting point was 135° C.

Example 7-1

The polyester compound (7-1) (20 parts by mass), cobalt stearate (II) (0.02 parts by mass in terms of cobalt) and a polyethylene terephthalate (trade name: BK-2180, manufactured by Japan Unipet) (80 parts by mass) were dry-blended. The obtained mixture was supplied to a double-screw extruder having two screws of 37 mm in diameter, at a rate of 15 kg/h. Melt-kneading was performed at a cylinder temperature of 260° C. and a strand was extruded from an extruder head. After cooling, the strand was pelletized to obtain an oxygen-absorbing resin composition.

Subsequently, a cavity was filled with the oxygen-absorbing resin composition, which was injected in a necessary amount from an injection cylinder under the following conditions to obtain test tube form injection-molded article (parison) (25 g). The obtained parison was cooled and then subjected to a secondary processing, in which the parison was heated and shaped by biaxial stretching blow molding to manufacture a single-layer bottle (oxygen-absorbing container).

(Shape of Parison)

The whole length of a parison was specified as 95 mm, the outer diameter as 22 mm and the film thickness as 2.7 mm. Note that a parison was manufactured by use of an injection molding machine (Type: M200, proving 4 parisons, manufactured by Meiki Co., Ltd.).

(Molding Conditions for Parison)
Temperature of injection cylinder: 280° C.
Temperature of resin flow channel in mold: 280° C.
Temperature of cooling water for mold: 20° C.

(Shape of Bottle Obtained by Secondary Processing)

The whole length of a bottle was specified as 160 mm, an outer diameter as 60 mm, an inner volume as 350 mL and a film thickness as 0.40 mm. The draw ratio was specified as 1.9 folds lengthwise and 2.7 folds widthwise. The shape of the bottom was a champagne-bottle type. The base of bottle has a dimple. Note that a blow molding machine (type: EFB 1000ET, manufactured by FRONTIER Inc.) was used for secondary processing.

(Secondary Processing Conditions)
Heating temperature of parison: 100° C.
Pressure of a stretching rod: 0.5 MPa
Primary blow pressure: 0.7 MPa
Secondary blow pressure: 2.5 MPa
Primary blow delayed time: 0.30 sec
Primary blow time: 0.30 sec
Secondary blow time: 2.0 sec
Blow discharge time: 0.6 sec
Mold temperature: 30° C.

Subsequently, the oxygen transmission rate of the obtained container was measured at 23° C. and under an atmosphere having a relative humidity of 50% (outside the container) and a relative humidity of 100% (inside the container). In the measurement herein, an oxygen transmission rate measurement apparatus (trade name: OX-TRAN 2-61, manufactured by MOCON) was used. The lower the measurement value, the more satisfactory oxygen barrier property. The oxygen transmission rate after 30 days from initiation of measurement is shown in Table 9.

Example 7-2

An oxygen-absorbing resin composition, a parison and a single-layer bottle were manufactured in the same manner as in Example 7-1 except that the staring amount of polyester compound (7-1) was changed to 50 parts by mass and the staring amount of polyethylene terephthalate was changed to 50 parts by mass. The oxygen transmission rate of the bottle was measured. The evaluation results are shown in Table 9.

Example 7-3

An oxygen-absorbing resin composition, a parison and a single-layer bottle were manufactured in the same manner as in Example 7-1 except that a polyester compound (7-2) was used in place of the polyester compound (7-1). The oxygen transmission rate of the bottle was measured. The evaluation results are shown in Table 9.

Example 7-4

An oxygen-absorbing resin composition, a parison and a single-layer bottle were manufactured in the same manner as in Example 7-1 except that a polyester compound (7-3) was used in place of the polyester compound (7-1). The oxygen transmission rate of the bottle was measured. The evaluation results are shown in Table 9.

Example 7-5

An oxygen-absorbing resin composition, a parison and a single-layer bottle were manufactured in the same manner as in Example 7-1 except that a polyester compound (7-4) was used in place of the polyester compound (7-1). The oxygen transmission rate of the bottle was measured. The evaluation results are shown in Table 9.

Example 7-6

An oxygen-absorbing resin composition, a parison and a single-layer bottle were manufactured in the same manner as in Example 7-1 except that the polyester compound (7-1) (18 parts by mass) and the polyester compound (7-2) (2 parts by mass) were used in place of the polyester compound (7-1) (20 parts by mass). The oxygen transmission rate of the bottle was measured. The evaluation results are shown in Table 9.

Comparative Example 7-1

A single-layer bottle having the same shape as in Example 7-1 was manufactured in the same manner as in Example 7-1 except that the polyester compound (7-1) and cobalt stearate (II) were not added, and polyethylene terephthalate (trade name: BK-2180, manufactured by Japan Unipet) (100 parts by mass) was used. The oxygen transmission rate of the single-layer bottle was measured in the same manner as in Example 7-1. The evaluation results are shown in Table 9.

TABLE 9

| | Oxygen-absorbing resin composition | | Oxygen transmission |
|---|---|---|---|
| | Polyester | Melting/ kneading ratio[1] | rate/30th day (cc/0.21 atm · day · package) |
| Example 7-1 | Polyester compound (7-1) | 20:80 | 0.010 |
| Example 7-2 | Polyester compound (7-1) | 50:50 | 0.002 |
| Example 7-3 | Polyester compound (7-2) | 20:80 | 0.012 |
| Example 7-4 | Polyester compound (7-3) | 20:80 | 0.006 |
| Example 7-5 | Polyester compound (7-4) | 20:80 | 0.008 |
| Example 7-6 | Polyester compound (7-1) + Polyester compound (7-2)[2] | 20:80 | 0.008 |
| Comparative Example 7-1 | (PET single layer) | — | 0.040 |

[1]Mass ratio of polyester compound: thermoplastic resin
[2]Mass ratio of polyester compound (7-1): polyester compound (7-2) = 90:10

As is apparent from Table 9, it was confirmed that the oxygen-absorbing containers of Examples 7-1 to 7-6, since oxygen is absorbed by the oxygen-absorbing layer, have low oxygen transmission rates compared to conventional PET bottle (Comparative Example 7-1) and thus these containers are excellent in oxygen barrier property.

Example 8-1

With the polyester compound (1-1) (100 parts by mass), cobalt acetate (II) (0.02 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition.

Subsequently, under the following conditions, the thermoplastic resin for constituting layer B was injected from an injection cylinder and then the resin composition for constituting layer A was injected from another injection cylinder simultaneously with the thermoplastic resin for constituting layer B. Subsequently, the thermoplastic resin for constituting layer B was injected in a necessary amount to fill a cavity to form an injection-molded article (test tube-form parison) of three layers, i.e., constituted of layer B/layer A/layer B. The total mass of the parison was specified as 25 g and the mass of layer A was specified as 10 mass % based on the total mass of the parison. Note that polyethylene terephthalate (trade name: BK-2180, manufactured by Japan Unipet) was used as the thermoplastic resin for constituting layer B, and the above oxygen-absorbing resin composition was used as the resin composition for constituting layer A.
(Shape of Parison)

The whole length of a parison was specified as 95 mm, the outer diameter as 22 mm and the film thickness as 2.7 mm. Note that a parison was manufactured by use of an injection molding machine (Type: M200, proving 4 parisons, manufactured by Meiki Co., Ltd.).
(Molding Conditions for Parison)
Temperature of injection cylinder for layer A: 250° C.
Temperature of injection cylinder for layer B: 280° C.
Temperature of resin flow channel in mold: 280° C.
Temperature of cooling water for mold: 15° C.

The obtained parison was cooled and then subjected to a secondary processing, in which the parison was heated and shaped by biaxial stretching blow molding to manufacture a multilayer bottle (oxygen-absorbing multilayer container).
(Shape of Bottle Obtained by Secondary Processing)

The whole length of a bottle was specified as 160 mm, an outer diameter as 60 mm, an inner volume as 350 mL and a film thickness as 0.28 mm. The draw ratio was specified as 1.9 folds lengthwise and 2.7 folds widthwise. The shape of the bottom was a champagne-bottle type. The base of bottle has a dimple. Note that a blow molding machine (type: EFB 1000ET, manufactured by FRONTIER Inc.) was used for secondary processing.
(Secondary Processing Conditions)
Heating temperature of parison: 100° C.
Pressure of a stretching rod: 0.5 MPa
Primary blow pressure: 0.7 MPa
Secondary blow pressure: 2.5 MPa
Primary blow delayed time: 0.33 sec
Primary blow time: 0.35 sec
Secondary blow time: 2.0 sec
Blow discharge time: 0.6 sec
Mold temperature: 30° C.

Subsequently, the oxygen transmission rate of the obtained container was measured at 23° C. and under an atmosphere having a relative humidity of 50%, which was measured outside the container and a relative humidity of 100%, which was measured within the container. Measurement herein was performed by use of an oxygen transmission rate measurement apparatus (trade name: OX-TRAN 2-61, manufactured by MOCON). The lower the measurement value, the more satisfactory oxygen barrier property. The oxygen transmission rate after 30 days from initiation of measurement is shown in Table 10.

Example 8-2

An oxygen-absorbing resin composition, a parison and a multilayer bottle were manufactured in the same manner as Example 8-1 except that a polyester compound (1-2) was used in place of the polyester compound (1-1). The oxygen transmission rate of the multilayer bottle was measured. The evaluation results are shown in Table 10.

Example 8-3

An oxygen-absorbing resin composition, a parison and a multilayer bottle were manufactured in the same manner as in Example 8-1 except that a polyester compound (1-3) was used in place of the polyester compound (1-1). The oxygen transmission rate of the multilayer bottle was measured. The evaluation results are shown in Table 10.

Comparative Example 8-1

A single-layer bottle having the same shape as in Example 8-1 was manufactured in the same manner as in Example 8-1 except that the polyester compound (7-1) and cobalt stearate (II) were not added and polyethylene terephthalate (trade name: BK-2180, manufactured by Japan Unipet) (100 parts by mass) was used. The oxygen transmission rate of the single-layer bottle was measured in the same manner as in Example 8-1. The evaluation results are shown in Table 10.

TABLE 10

| Resin used in Layer A | | Oxygen transmission rate/30th day mL/(0.21 atm · day · package) |
|---|---|---|
| Example 8-1 | Polycondensation product of dimethyl tetralin-2,6-dicarboxylate/1,4-butanediol | 0.005 |
| Example 8-2 | Polycondensation product of dimethyl tetralin-2,6-dicarboxylate/ethylene glycol | 0.006 |
| Example 8-3 | Polycondensation product of dimethyl tetralin-2,6-dicarboxylate/1,6-hexanediol | 0.005 |
| Comparative Example 8-1 | (Polyethylene terephthalate single-layer bottle) | 0.040 |

As is apparent from Table 10, it was confirmed that the oxygen-absorbing containers of Examples 8-1 to 8-3, since oxygen is absorbed by the oxygen-absorbing layer, have low oxygen transmission rates compared to conventional PET bottle (Comparative Example 8-1) and thus these containers are excellent in oxygen barrier property.

Example 9-1

The polyester compound (7-1) (50 parts by mass), cobalt stearate (II) (0.02 parts by mass in terms of cobalt) and a polyethylene terephthalate (trade name: BK-2180, manufactured by Japan Unipet) (50 parts by mass) were dry-blended. The obtained mixture was supplied to a double-screw extruder having two screws of 37 mm in diameter, at a rate of 15 kg/h. Melt-kneading was performed at a cylinder temperature of 260° C. and a strand was extruded from an extruder head. After cooling, the strand was pelletized to obtain an oxygen-absorbing resin composition.

Subsequently, under the following conditions, the thermoplastic resin (b) for constituting layer B was injected from an injection cylinder and then the resin composition for constituting layer A was injected from another injection cylinder simultaneously with the thermoplastic resin (b) for constituting layer B. Subsequently, the thermoplastic resin (b) for constituting layer B was injected in a necessary amount to fill a cavity to form an injection-molded article (test tube-form parison) of three layers, i.e., constituted of layer B/layer A/layer B. The total mass of the parison was specified as 25 g and the mass of layer A was specified as 10 mass % based on the total mass of the parison. Note that the above oxygen-absorbing resin composition was used as the resin composition for constituting the oxygen-absorbing layer (layer A), and a polyethylene terephthalate (trade name: BK-2180, manufactured by Japan Unipet) was used as the thermoplastic resin (b).
(Shape of Parison)

The whole length of a parison was specified as 95 mm, the outer diameter as 22 mm and the film thickness as 2.7 mm. Note that a parison was manufactured by use of an injection molding machine (Type: M200, proving 4 parisons, manufactured by Meiki Co., Ltd.).
(Molding Conditions for Parison)
Temperature of injection cylinder for layer A: 280° C.
Temperature of injection cylinder for layer B: 280° C.
Temperature of resin flow channel in mold: 280° C.
Temperature of cooling water for mold: 15° C.

The obtained parison was cooled and then subjected to a secondary processing, in which the parison was heated and shaped by biaxial stretching blow molding to manufacture a multilayer bottle (oxygen-absorbing multilayer container).
(Shape of Bottle Obtained by Secondary Processing)

The whole length of a bottle was specified as 160 mm, an outer diameter as 60 mm, an inner volume as 350 mL and a film thickness as 0.40 mm. The draw ratio was specified as 1.9 folds lengthwise and 2.7 folds widthwise. The shape of the bottom was a champagne-bottle type. The base of bottle has a dimple. Note that a blow molding machine (type: EFB 1000ET, manufactured by FRONTIER Inc.) was used for secondary processing.
(Secondary Processing Conditions)
Heating temperature of parison: 102° C.
Pressure of a stretching rod: 0.5 MPa
Primary blow pressure: 0.7 MPa
Secondary blow pressure: 2.5 MPa
Primary blow delayed time: 0.30 sec
Primary blow time: 0.30 sec
Secondary blow time: 2.0 sec
Blow discharge time: 0.6 sec
Mold temperature: 30° C.

Subsequently, the oxygen transmission rate of the obtained container was measured at 23° C. and under an atmosphere having a relative humidity of 50% (outside the container) and a relative humidity of 100% (inside the container). In the measurement herein, an oxygen transmission rate measurement apparatus (trade name: OX-TRAN 2-61, manufactured by MOCON) was used. The lower the measurement value, the more satisfactory oxygen barrier property. The oxygen transmission rate after 30 days from initiation of measurement is shown in Table 11.

Example 9-2

An oxygen-absorbing resin composition, a parison and a multilayer bottle were manufactured in the same manner as in Example 9-1 except that the staring amount of polyester compound (7-1) was changed to 20 parts by mass and the staring amount of polyethylene terephthalate was changed to 80 parts by mass. The oxygen transmission rate of the multilayer bottle was measured. The evaluation results are shown in Table 11.

Example 9-3

An oxygen-absorbing resin composition, a parison and a multilayer bottle were manufactured in the same manner as in Example 9-1 except that the staring amount of polyester compound (7-1) was changed to 80 parts by mass and the staring amount of polyethylene terephthalate was changed to 20 parts by mass. The oxygen transmission rate of the multilayer bottle was measured. The evaluation results are shown in Table 11.

Example 9-4

An oxygen-absorbing resin composition, a parison and a multilayer bottle were manufactured in the same manner as in Example 9-1 except that a polyester compound (7-2) was used in place of the polyester compound (7-1). The oxygen transmission rate of the multilayer bottle was measured. The evaluation results are shown in Table 11.

Example 9-5

An oxygen-absorbing resin composition, a parison and a multilayer bottle were manufactured in the same manner as in Example 9-1 except that a polyester compound (7-3) was used in place of the polyester compound (7-1). The oxygen transmission rate of the multilayer bottle was measured. The evaluation results are shown in Table 11.

Example 9-6

An oxygen-absorbing resin composition, a parison and a multilayer bottle were manufactured in the same manner as in Example 9-1 except that a polyester compound (7-4) was used in place of the polyester compound (7-1). The oxygen transmission rate of the multilayer bottle was measured. The evaluation results are shown in Table 11.

Example 9-7

An oxygen-absorbing resin composition, a parison and a multilayer bottle were manufactured in the same manner as in Example 9-1 except that the polyester compound (7-1) (45 parts by mass) and the polyester compound (7-2) (5 parts by mass) were used in place of the polyester compound (7-1) (50 parts by mass). The oxygen transmission rate of the multilayer bottle was measured. The evaluation results are shown in Table 11.

Comparative Example 9-1

A single-layer bottle having the same shape as in Example 9-1 was manufactured in the same manner as in Example 9-1 except that the polyester compound (7-1) and cobalt stearate (II) were not added and polyethylene terephthalate (trade name: BK-2180, manufactured by Japan Unipet) (100 parts by mass) was used. The oxygen transmission rate of the single-layer bottle was measured. The evaluation results are shown in Table 11.

TABLE 11

| | Oxygen-absorbing resin composition | | |
| --- | --- | --- | --- |
| | Polyester | Melting/ kneading ratio[1] | Oxygen transmission rate/30th day (cc/0.21 atm · day · package) |
| Example 9-1 | Polyester compound (7-1) | 50:50 | 0.008 |
| Example 9-2 | Polyester compound (7-1) | 20:80 | 0.012 |
| Example 9-3 | Polyester compound (7-1) | 80:20 | 0.004 |
| Example 9-4 | Polyester compound (7-2) | 50:50 | 0.010 |
| Example 9-5 | Polyester compound (7-3) | 50:50 | 0.007 |
| Example 9-6 | Polyester compound (7-4) | 50:50 | 0.008 |
| Example 9-7 | Polyester compound (7-1) + Polyester compound (7-2)[2] | 50:50 | 0.009 |
| Comparative Example 9-1 | (PET single-layer) | — | 0.040 |

[1]Mass ratio of polyester compound thermoplastic resin (a)
[2]Mass ratio of polyester compound (7-1): polyester compound (7-2) = 90:10

As is apparent from Table 11, it was confirmed that the oxygen-absorbing containers of Examples 9-1 to 9-7, since oxygen is absorbed by the oxygen-absorbing layer, have low oxygen transmission rates compared to conventional PET bottle (Comparative Example 9-1) and thus these containers are excellent in oxygen barrier property.

Now, the oxygen-absorbing medical multilayer molded container of the present invention will be more specifically described below by way of Examples and Comparative Examples; however, the present invention is not limited by these. Note that vials are taken as an example and demonstrated in the following Examples. As is described in the specification of the present application, since characteristics demanded for ampules and prefilled syringes are the same as for vials, the present invention is not particularly limited by the following Examples.

Production Example of Polymer

Production Example 10-1

To a polyester resin manufacturing apparatus equipped with a packed tower system rectifier, a partial condenser, a total condenser, a cold trap, a stirrer, a heating unit and a nitrogen inlet tube, dimethyl tetralin-2,6-dicarboxylate (543 g) obtained in Synthesis Example 1-1, 1,4-butanediol (315 g) and tetrabutyl titanate (0.171 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (0.171 g) was added. The temperature was gradually increased and pressure was gradually decreased and then polycondensation was performed at 245° C. and 133 Pa or less to obtain a tetralin ring-containing polyester compound (10-1).

The weight average molecular weight and number average molecular weight of the obtained polyester compound (10-1) were determined by GPC (gel permeation chromatography). As a result, the polystyrene-equivalent weight average molecular weight was $8.7 \times 10^4$ and the number average molecular weight thereof was $3.1 \times 10^4$. The glass transition temperature and melting point were measured by DSC. As a result, the glass transition temperature was 36° C. and the melting point was 145° C.

Production Example 10-2

A tetralin ring-containing polyester compound (10-2) was synthesized in the same manner as in Production Example 10-1 except that ethylene glycol (217 g) was used in place of 1,4-butanediol of Production Example 10-1. The polystyrene-equivalent weight average molecular weight of the polyester compound (10-2) was $8.5 \times 10^4$ and the number average molecular weight thereof was $3.0 \times 10^4$. The glass transition temperature was 67° C. and the melting point was not determined because of amorphous crystal.

Production Example 10-3

A tetralin ring-containing polyester compound (10-3) was synthesized in the same manner as in Production Example 10-1 except that 1,6-hexanediol (413 g) was used in place of 1,4-butanediol of Production Example 10-1. The polystyrene-equivalent weight average molecular weight of the polyester compound (10-3) was $8.9 \times 10^4$ and the number average molecular weight thereof was $3.3 \times 10^4$. The glass transition temperature was 16° C. and the melting point was 137° C.

Production Example 10-4

A tetralin ring-containing polyester compound (10-4) was synthesized in the same manner as in Production Example 10-1 except that 1,4-butanediol (258 g) and ethylene glycol (44 g) were used in place of 1,4-butanediol (315 g) of Production Example 10-1. The polystyrene-equivalent weight average molecular weight of the polyester compound (10-4) was $1.1 \times 10^5$ and the number average molecular weight thereof was $4.1 \times 10^4$. The glass transition temperature was 39° C. and the melting point was 135° C.

Example 10-1

With a polyester compound (10-1) (100 parts by mass), cobalt stearate (II) (0.02 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition (10-1). Subsequently, as shown below, a multilayer injection molded container, i.e., vial, was manufactured by using the oxygen-absorbing resin composition (10-1). Thereafter, performance of the obtained vial was evaluated as shown below. The evaluation results are shown in Table 12.

[Manufacturing of Vial]

Under the following conditions, the thermoplastic resin for constituting a resin layer (layer B) was injected from an injection cylinder and then the oxygen-absorbing resin composition (10-1) for constituting an oxygen-absorbing layer (layer A) was injected from another injection cylinder simultaneously with the thermoplastic resin for constituting layer B. Subsequently, a thermoplastic resin for constituting layer B was injected in a necessary amount to fill the cavity of an injection mold to obtain an injection molded article of a three-layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. A cycloolefin copolymer (trade name: TOPAS6013, manufactured by Ticona GmbH) was used as the thermoplastic resin for constituting layer B.
(Shape of Vial)

The whole length of a vial was specified as 89 mm, the outer diameter as 40 mmφ and the film thickness as 1.8 mm. Note that a vial was manufactured by use of an integrated injection blow molding machine (Type: IBS 85, proving 4 vials, manufactured by UNILOY).
(Molding Conditions for Vial)
Temperature of injection cylinder for layer A: 260° C.
Temperature of injection cylinder for layer B: 280° C.
Temperature of resin flow channel in injection mold: 280° C.
Blowing temperature: 150° C.
Temperature of cooling water for blow mold: 15° C.
[Performance Evaluation of Vial]

Measurement of oxygen transmission rate, evaluation of appearance after molding, drop test and elution test of the obtained vials were performed in accordance with the following methods and evaluation was made based on the following criteria.
(1) Oxygen Transmission Rate of Vial (OTR)

At the 30th day from initiation of measurement, the oxygen transmission rate was measured at 23° C. and under an atmosphere having a relative humidity of 50%, which was measured outside the molded article and a relative humidity of 100%, which was measured within the molded article. Measurement was performed by use of an oxygen transmission rate measurement apparatus (trade name: OX-TRAN 2-21ML, manufactured by MOCON). The lower the measurement value, the more satisfactory the oxygen barrier property. Note that detection lower limit of oxygen transmission rate measured is $5 \times 10^{-5}$ mL/(0.21 atm·day·package).
(2) Appearance after Molding Presence or absence of whitening of vial after molding was visually observed.
(3) Drop Test After a vial was stored under the conditions of 40° C. and 90% RH for one month, the vial was filled up with pure water (50 mL) and then sealed by a rubber tap and an aluminum cap. The sealed container thus obtained was allowed to drop from a height of 2 m. The appearance of the container at this time was checked.
(4) Elusion Test After a vial was stored under the conditions of 40° C. and 90% RH for one month, the vial was filled up with pure water (50 mL) and then sealed by a rubber tap and an aluminum cap. The sealed container thus obtained was stored under the conditions of 40° C. and 60% RH for 4 months and then the total amount of carbon (hereinafter, TOC) in the pure water was measured.
(TOC measurement)
Apparatus: TOC-$V_{CPH}$ manufactured by Shimadzu Corporation
Temperature of combustion furnace: 720° C.
Gas/flow rate: highly purified air, 150 mL/min measured by TOC meter
Injection amount: 150
Detection limit: 1 μg/mL Examples 10-2 to 10-4

Oxygen-absorbing resin compositions and vials were manufactured in the same manner as in Example 10-1 except that each of the corresponding polyester compounds shown in Table 12 was used in place of the polyester compound (10-1). The performance of the obtained vials was individually evaluated in the same manner as in Example 10-1. The evaluation results are shown in Table 12.

Example 10-5

An oxygen-absorbing resin composition and a vial were manufactured in the same manner as in Example 10-1 except that the polyester compound (10-1) (90 parts by mass) and the polyester compound (10-2) (10 parts by mass) were used in place of the polyester compound (10-1) (100 parts by mass). The performance of the obtained vial was evaluated in the same manner as in Example 10-1. The evaluation results are shown in Table 12.

Comparative Example 10-1

A single-layer vial having the same shape as in Example 10-1 was manufactured in the same manner as in Example 10-1 except that a cycloolefin copolymer (TOPAS 6013 manufactured by Ticona GmbH) (100 parts by mass) was used in place of the oxygen-absorbing resin composition (10-1). The performance of the obtained vial was evaluated in the same manner as in Example 10-1. The evaluation results are shown in Table 12.

Comparative Example 10-2

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-1). A vial was manufactured in the same manner as in Example 10-1 except that the oxygen-absorbing resin composition (M-1) was used in place of the oxygen-absorbing resin composition (10-1). The performance of the obtained vial was evaluated in the same manner as in Example 10-1. The evaluation results are shown in Table 12.

TABLE 12

| | Resin used in Layer A | Layer constitution | Oxygen transmission rate (30th day) mL/ (021 atm · day · package) | Appearance after molding | Drop test | Elution test TOC amount (μg/mL) |
|---|---|---|---|---|---|---|
| Example 10-1 | Polyester compound (10-1) | Three layers | Detection limit or less | Slightly whitened in part | No breakage is observed in all containers | Detection limit or less |
| Example 10-2 | Polyester compound (10-2) | Three layers | Detection limit or less | Transparent | No breakage is observed in all containers | Detection limit or less |
| Example 10-3 | Polyester compound (10-3) | Three layers | Detection limit or less | Slightly whitened in whole | No breakage is observed in all containers | Detection limit or less |
| Example 10-4 | Polyester compound (10-4) | Three layers | Detection limit or less | Transparent | No breakage is observed in all containers | Detection limit or less |
| Example 10-5 | Polyester compound (10-1) + (10-2)*) | Three layers | Detection limit or less | Transparent | No breakage is observed in all containers | Detection limit or less |
| Comparative Example 10-1 | — | Single layer | 0.0871 | Transparent | No breakage is observed in all containers | Detection limit or less |
| Comparative Example 10-2 | Nylon MXD6 | Three layers | Detection limit or less | Slightly whitened in whole | 14 out of 20 containers are broken | 15 |

*)Blend of polyester compound (10-1) (90 parts by mass) and polyester compound (10-2) (10 parts by mass)

As is apparent from Table 12, it was confirmed that the vials of Examples 10-1 to 10-5 have satisfactory oxygen barrier property and maintain satisfactory strength even after long-term storage, and that the amount of elution from the container to the content is small. Furthermore, it was confirmed that the vials of Examples 10-1 to 10-5 each have sufficient visibility of the content in a container, in particular, the vials of Examples 10-2, 10-4 and 10-5 are excellent in transparency.

Example 11-1

With a polyester compound (10-1) (100 parts by mass), cobalt stearate (II) (0.02 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition (11-1). Subsequently, as shown below, a multilayer injection molded container, i.e., vial, was manufactured by using the oxygen-absorbing resin composition (11-1). The performance of the obtained vial was evaluated in the same manner as in Example 10-1. Furthermore, the performance, i.e., water vapor transmission rate of the vial was evaluated in the following manner. The evaluation results are shown in Table 13.

[Manufacturing of Vial]

Under the following conditions, the thermoplastic resin for constituting a resin layer (layer B) was injected from an injection cylinder and then the oxygen-absorbing resin composition (11-1) for constituting an oxygen-absorbing layer (layer A) was injected from another injection cylinder simultaneously with the thermoplastic resin for constituting layer B. Subsequently, a thermoplastic resin for constituting layer B was injected in a necessary amount to fill the cavity of an injection mold to obtain an injection molded article of a three-layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. A cycloolefin copolymer (trade name: TOPAS6013, manufactured by Ticona GmbH) was used as the thermoplastic resin for constituting layer B.

(Shape of Vial)

The whole length of a vial was specified as 89 mm, the outer diameter as 40 mmφ and the film thickness as 1.8 mm. Note that a vial was manufactured by use of an integrated injection blow-molding machine (Type: IBS 85, proving 4 vials, manufactured by UNILOY).

(Molding Conditions for Vial)

Temperature of injection cylinder for layer A: 260° C.
Temperature of injection cylinder for layer B: 280° C.
Temperature of resin flow channel in injection mold: 280° C.
Blowing temperature: 150° C.
Temperature of cooling water for blow mold: 15° C.

[Performance Evaluation of Vial]

(5) Water Vapor Transmission Rate (WVTR) of Vial

The water vapor transmission rate of 10th day from initiation of measurement was measured at 40° C. and under an atmosphere having a relative humidity of 100%, which was measured outside a molded article. Measurement was performed by use of a water vapor transmission rate measurement apparatus (trade name: PERMATRAN-W 3/33G, manufactured by MOCON). The lower the measurement value, the more satisfactory the water vapor barrier property. Note that the detection lower limit of water vapor transmission rate measured is $5 \times 10^{-4}$ g/(day·package).

Examples 11-2 to 11-4

Oxygen-absorbing resin compositions and vials were manufactured in the same manner as in Example 11-1 except that each of the corresponding polyester compounds shown in Table 13 was used in place of the polyester compound (10-1). The performance of the obtained vials was individually evaluated in the same manner as in Example 11-1. The evaluation results are shown in Table 13.

Example 11-5

An oxygen-absorbing resin composition and a vial were manufactured in the same manner as in Example 11-1 except that the polyester compound (10-1) (90 parts by mass) and the polyester compound (10-2) (10 parts by mass) were used in place of the polyester compound (10-1) (100 parts by mass). The performance of the obtained vial was evaluated in the same manner as in Example 11-1. The evaluation results are shown in Table 13.

Comparative Example 11-1

A single-layer vial having the same shape as in Example 11-1 was manufactured in the same manner as in Example 11-1 except that a cycloolefin copolymer (TOPAS 6013 manufactured by Ticona GmbH) (100 parts by mass) was used in place of the oxygen-absorbing resin composition (10-1). The performance of the obtained vial was evaluated in the same manner as in Example 11-1. The evaluation results are shown in Table 13.

Comparative Example 11-2

A vial was manufactured in the same manner as in Example 1 except that a polycarbonate (Lexan 144R, manufactured by Sabic) was used in place of the cycloolefin copolymer as the thermoplastic resin for constituting layer B. The performance of the obtained vial was evaluated in the same manner as in Example 11-1. The evaluation results are shown in Table 13.

Comparative Example 11-3

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-2). A vial was manufactured in the same manner as in Example 11-1 except that the oxygen-absorbing resin composition (M-2) was used in place of the oxygen-absorbing resin composition (10-1). The performance of the obtained vial was evaluated in the same manner as in Example 11-1. The evaluation results are shown in Table 13.

As is apparent from Table 13, it was confirmed that the vials of Examples 11-1 to 11-5 have satisfactory oxygen barrier property and water vapor barrier property and maintain satisfactory strength even after long-term storage, and that the amount of elution from the container to the content is small. Furthermore, it was confirmed that the vials of Examples 11-1 to 11-5 each have sufficient visibility of the content in a container, in particular, the vials of Examples 11-2, 11-4 and 11-5 are excellent in transparency.

Production Example of Polymer

Production Example 12-1

To a polyester resin manufacturing apparatus (0.15 cubic meters) equipped with a packed tower system rectifier, a partial condenser, a total condenser, a cold trap, a stirrer, a heating unit and a nitrogen inlet tube, dimethyl tetralin-2, 6-dicarboxylate (52.49 kg) obtained in Synthesis Example 1-1, 1,4-butanediol (30.49 kg) and tetrabutyl titanate (8.28 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (8.28 g) was added. The temperature was gradually increased and pressure was gradually decreased and then polycondensation was performed at 245° C. and 0.1 kPa or less to obtain a tetralin ring-containing polyester compound (12-1).

The weight average molecular weight and number average molecular weight of the obtained polyester compound (12-1) were determined by GPC (gel permeation chromatography). As a result, the polystyrene-equivalent weight average molecular weight was $8.7 \times 10^4$ and the number average molecular weight thereof was $3.1 \times 10^4$. The glass transition temperature and melting point were measured by DSC. As a result, the glass transition temperature was 36° C. and the melting point was 145° C.

TABLE 13

| | Resin used in Layer A | Resin used in Layer B | Layer constitution | Oxygen transmission rate (30th day)[2] | Water vapor transmission rate (10th day) g/(day · package) | Appearance after molding | Drop test | Elution test TOC amount (μg/mL) |
|---|---|---|---|---|---|---|---|---|
| Example 11-1 | Polyester compound (10-1) | COC | Three layers | Detection limit or less | 0.0008 | Slightly whitened in part | No breakage is observed in all containers | Detection limit or less |
| Example 11-2 | Polyester compound (10-2) | COC | Three layers | Detection limit or less | 0.0007 | Transparent | No breakage is observed in all containers | Detection limit or less |
| Example 11-3 | Polyester compound (10-3) | COC | Three layers | Detection limit or less | 0.0007 | Slightly whitened in whole | No breakage is observed in all containers | Detection limit or less |
| Example 11-4 | Polyester compound (10-4) | COC | Three layers | Detection limit or less | 0.0008 | Transparent | No breakage is observed in all containers | Detection limit or less |
| Example 11-5 | Polyester compound (10-1) + (10-2)[1] | COC | Three layers | Detection limit or less | 0.0007 | Transparent | No breakage is observed in all containers | Detection limit or less |
| Comparative Example 11-1 | COC Single layer | | Single layer | 0.0871 | 0.0007 | Transparent | No breakage is observed in all containers | Detection limit or less |
| Comparative Example 11-2 | Polyester compound (10-1) | PC | Three layers | Detection limit or less | 0.0220 | Transparent | No breakage is observed in all containers | Detection limit or less |
| Comparative Example 11-3 | Nylon MXD6 | COC | Three layers | Detection limit or less | 0.0009 | Slightly whitened in whole | 14 out of 20 containers are broken | 15 |

[1] Blend of polyester compound (10-1) (90 parts by mass) and polyester compound (10-2) (10 parts by mass)

Production Example 12-2

To a polyester resin manufacturing apparatus (0.03 cubic meters) equipped with a packed tower system rectifier, a partial condenser, a total condenser, a cold trap, a stirrer, a heating unit and a nitrogen inlet tube, dimethyl tetralin-2,6-dicarboxylate (18.15 kg) obtained in Synthesis Example 1-1, ethylene glycol (7.26 kg) and tetrabutyl titanate (2.86 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (2.86 g) was added. The temperature was gradually increased and pressure was gradually decreased and then polycondensation was performed at 245° C. and 0.1 kPa or less to obtain a tetralin ring-containing polyester compound (12-2).

The polystyrene-equivalent weight average molecular weight of the obtained polyester compound (12-2) was $8.5 \times 10^4$ and the number average molecular weight thereof was $3.0 \times 10^4$. The glass transition temperature was 67° C. and the melting point was not determined because of amorphous crystal.

Production Example 12-3

To a polyester resin manufacturing apparatus (0.03 cubic meters) equipped with a packed tower system rectifier, a partial condenser, a total condenser, a cold trap, a stirrer, a heating unit and a nitrogen inlet tube, dimethyl tetralin-2,6-dicarboxylate (14.79 kg) obtained in Synthesis Example 1-1, 1,6-hexanediol (11.26 kg) and tetrabutyl titanate (2.33 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (2.33 g) was added. The temperature was gradually increased and pressure was gradually decreased and then polycondensation was performed at 245° C. and 0.1 kPa or less to obtain a tetralin ring-containing polyester compound (12-3).

The polystyrene-equivalent weight average molecular weight of the obtained polyester compound (12-3) was $8.9 \times 10^4$ and the number average molecular weight thereof was $3.3 \times 10^4$. The glass transition temperature was 16° C. and the melting point was 137° C.

Production Example 12-4

To a polyester resin manufacturing apparatus (0.03 cubic meters) equipped with a packed tower system rectifier, a partial condenser, a total condenser, a cold trap, a stirrer, a heating unit and a nitrogen inlet tube, dimethyl tetralin-2,6-dicarboxylate (16.63 kg) obtained in Synthesis Example 1-1, 1,4-butanediol (7.73 kg), ethylene glycol (1.33 kg) and tetrabutyl titanate (2.62 g) were supplied. The temperature of the mixture was raised up to 230° C. under a nitrogen atmosphere and a transesterification reaction was performed. After the reaction conversion rate of the dicarboxylate component reached 85% or more, tetrabutyl titanate (2.62 g) was added. The temperature was gradually increased and pressure was gradually decreased and then polycondensation was performed at 245° C. and 0.1 kPa or less to obtain a tetralin ring-containing polyester compound (12-4).

The polystyrene-equivalent weight average molecular weight of the obtained polyester compound (12-4) was $1.1 \times 10^5$ and the number average molecular weight thereof was $4.1 \times 10^4$. The glass transition temperature was 39° C. and the melting point was 135° C.

Example 12-1

With a polyester compound (12-1) (100 parts by mass), cobalt stearate (II) (0.02 parts by mass in terms of cobalt) was dry-blended. The obtained mixture was supplied to a double-screw extruder having two screws of 37 mm in diameter, at a rate of 30 kg/h. Melt-kneading was performed at a cylinder temperature of 220° C. and a strand was extruded from an extruder head. After cooling, the strand was pelletized to obtain an oxygen-absorbing resin composition (12-1). Subsequently, as shown below, a multilayer injection molded container, i.e., vial, was manufactured by using the oxygen-absorbing resin composition (12-1). The performance of the obtained vial was evaluated in the same manner as in Example 10-1. The evaluation results are shown in Table 14.

[Manufacturing of Vial]

Under the following conditions, the thermoplastic resin for constituting a resin layer (layer B) was injected from an injection cylinder and then the oxygen-absorbing resin composition (12-1) for constituting an oxygen-absorbing layer (layer A) was injected from another injection cylinder simultaneously with the thermoplastic resin for constituting layer B. Subsequently, a thermoplastic resin for constituting layer B was injected in a necessary amount to fill the cavity of an injection mold to obtain an injection molded article of a three-layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. Polyethylene terephthalate (trade name: BK 2180, manufactured by Japan Unipet) was used as the thermoplastic resin for constituting layer B.

(Shape of Vial)

The whole length of a vial was specified as 89 mm, the outer diameter as 40 mmφ and the film thickness as 1.8 mm. Note that a vial was manufactured by use of an integrated injection blow molding machine (Type: IBS 85, proving 4 vials, manufactured by UNILOY).

(Molding Conditions for Vial)

Temperature of injection cylinder for layer A: 260° C.
Temperature of injection cylinder for layer B: 280° C.
Temperature of resin flow channel in injection mold: 280° C.
Blowing temperature: 150° C.
Temperature of cooling water for blow mold: 15° C.

Examples 12-2 to 12-4

Oxygen-absorbing resin compositions and vials were manufactured in the same manner as in Example 12-1 except that each of the corresponding polyester compounds shown in Table 14 was used in place of the polyester compound (12-1). The performance of the obtained vials was individually evaluated in the same manner as in Example 10-1. The evaluation results are shown in Table 14.

Example 12-5

An oxygen-absorbing resin composition and a vial were manufactured in the same manner as in Example 12-1 except that the polyester compound (12-1) (90 parts by mass) and a polyester compound (12-2) (10 parts by mass) were used in place of the polyester compound (12-1) (100 parts by mass). The performance of the obtained vial was evaluated in the same manner as in Example 10-1. The evaluation results are shown in Table 14.

Comparative Example 12-1

A single-layer vial having the same shape as in Example 12-1 was manufactured in the same manner as in Example 12-1 except that a polyethylene terephthalate ((BK2180) manufactured by Japan Unipet) (100 parts by mass) was used in place of the oxygen-absorbing resin composition (12-1). The performance of the obtained vial was evaluated in the same manner as in Example 10-1. The evaluation results are shown in Table 14.

Comparative Example 12-2

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 30 kg/h. Melt-kneading was performed at a cylinder temperature of 280° C. and a strand was extruded from an extruder head. After cooling, the strand was pelletized to obtain an oxygen-absorbing resin composition (M-3). A vial was manufactured in the same manner as in Example 12-1 except that the oxygen-absorbing resin composition (M-3) was used in place of the oxygen-absorbing resin composition (12-1). The performance of the obtained vial was evaluated in the same manner as in Example 10-1. The evaluation results are shown in Table 14.

sition (13-1). Subsequently, as shown below, a multilayer injection molded container, i.e., syringe, was manufactured by using the oxygen-absorbing resin composition (13-1). Thereafter, performance of the obtained syringe was evaluated as shown below. The evaluation results are shown in Table 15.

[Manufacturing of Syringe]

Under the following conditions, the thermoplastic resin for constituting a resin layer (layer B) was injected from an injection cylinder and then the oxygen-absorbing resin composition (13-1) for constituting an oxygen-absorbing layer (layer A) was injected from another injection cylinder simultaneously with the thermoplastic resin for constituting layer B. Subsequently, the thermoplastic resin for constituting layer B was injected in a necessary amount to fill the cavity of an injection mold to manufacture a syringe constituted of three layers (B/A/B). The total mass of the syringe herein was specified as 1.95 g and the mass of layer A was specified as 30 mass % of the total mass of the syringe. A cycloolefin copolymer (trade name: TOPAS 6013, manufactured by Ticona GmbH) was used as the thermoplastic resin for constituting layer B.

(Shape of Syringe)

The volume (1 cc) of the content was used as a standard in accordance with 1S011040-6. Note that a syringe was manufactured by use of an injection molding machine (type: ASB-12N/10, manufactured by Nissei ASB Machine Co., Ltd).

(Conditions for Molding Syringe)
Temperature of injection cylinder for layer A: 250° C.
Temperature of injection cylinder for layer B: 260° C.
Temperature of resin flow channel in injection mold: 270° C.
Mold temperature: 18° C.

TABLE 14

|  | Example 12-1 | Example 12-2 | Example 12-3 | Example 12-4 | Example 12-5 | Comparative Example 12-1 | Comparative Example 12-2 |
|---|---|---|---|---|---|---|---|
| Layer constitution | Three layers | Three layers | Three layers | Three layers | Three layers | Single layer | Three layers |
| Resin used in oxygen-absorbing resin composition | Polyester compound (12-1) | Polyester compound (12-2) | Polyester compound (12-3) | Polyester compound 12-4) | Polyester compound (12-1) + (12-2)[2] | — | Nylon MXD6 |
| Oxygen transmission rate[1] | Detection limit or less | Detection limit or less | Detection limit or less | Detection limit or less | Detection limit or less | 0.011 | Detection limit or less |
| Visibility of content | Slightly hazy (acceptable) | Transparent (acceptable) | Slightly hazy (acceptable) | Transparent (acceptable) | Transparent (acceptable) | Transparent (acceptable) | Hazy (acceptable) |
| Impact resistance | No breakage | No breakage | No breakage | No breakage | No breakage | No breakage | Interlayer peeling occurs in 9 products |
| Elution test (µg/ml) | Detection limit or less | Detection limit or less | Detection limit or less | Detection limit or less | Detection limit or less | Detection limit or less | 27 |

[1]Unit: mL/(0.21 atm · day · package)
[2]Blend of polyester compound (12-1) (90 parts by mass) and polyester compound (12-2) (10 parts by mass)

As is apparent from Table 14, it was confirmed that the vials of Examples 12-1 to 12-5 maintain satisfactory oxygen barrier property, visibility of a content and impact resistance after long-term storage, and that the amount of elution from the container to the content is small.

Example 13-1

With a polyester compound (12-1) (100 parts by mass), cobalt stearate (II) (0.02 parts by mass in terms of cobalt) was dry-blended. The obtained mixture was supplied to a double-screw extruder having two screws of 37 mm in diameter, at a rate of 30 kg/h. Melt-kneading was performed at a cylinder temperature of 220° C. and a strand was extruded from an extruder head. After cooling, the strand was pelletized to obtain an oxygen-absorbing resin compo-

[Performance Evaluation of Syringe]

Measurement of oxygen transmission rate, evaluation of appearance after molding, drop test and elution test of the obtained syringes were performed in accordance with the following methods and evaluation was made based on the following criteria.

(1) Oxygen Transmission Rate (OTR) of Syringe

At the 30th day from initiation of measurement, the oxygen transmission rate was measured at 23° C. and under an atmosphere having a relative humidity of 50%, which was measured outside the molded article, and a relative humidity of 100%, which was measured within the molded article. Measurement was performed by use of an oxygen transmission rate measurement apparatus (trade name: OX-TRAN 2-21ML, manufactured by MOCON). The lower the measurement value, the more satisfactory the oxygen barrier property. Note that detection lower limit of oxygen transmission rate measured is $5 \times 10^{-5}$ mL/(0.21 atm·day·package).

(2) Visibility of Content in Syringe

The content in a syringe was visually observed. The visibility of a content in the syringe was evaluated. If the content was visible without any problem, the syringe was determined to come up to the standard.

(3) Impact Resistance Test

After a syringe was stored under the conditions of 40° C. and 90% RH for one month, a metal ball (50 g) was dropped on the body of the syringe from a height of 2 m. At this time, the presence or absence of breakage was checked with respect to 20 samples.

(4) Elution Test

After a syringe was stored under the conditions of 40° C. and 90% RH for one month, the syringe was filled with pure water (1 cc) and sealed with a plunger equipped with a top cap and a gasket. The syringe thus obtained was stored under the conditions of 40° C. and 60% RH for 4 months and thereafter, the total amount of carbon (hereinafter, TOC) in the pure water was measured.

(TOC Measurement)

Apparatus: TOC-$V_{CPH}$ manufactured by Shimadzu Corporation

Temperature of combustion furnace: 720° C.

Gas/flow rate: highly purified air, 150 mL/min measured by TOC meter

Injection amount: 150 μl,

Detection limit: 1 μg/mL

Examples 13-2 to 13-4

Oxygen-absorbing resin compositions and syringes were manufactured in the same manner as in Example 13-1 except that each of the corresponding polyester compounds shown in Table 15 was used in place of the polyester compound (12-1). The performance of the obtained syringes was individually evaluated in the same manner as in Example 13-1. The evaluation results are shown in Table 15.

Example 13-5

An oxygen-absorbing resin composition and a syringe were manufactured in the same manner as in Example 13-1 except that the polyester compound (12-1) (90 parts by mass) and polyester compound (12-2) (10 parts by mass) were used in place of the polyester compound (12-1) (100 parts by mass). The performance of the obtained syringe was evaluated in the same manner as in Example 13-1. The evaluation results are shown in Table 15.

Comparative Example 13-1

A single-layer syringe having the same shape as in Example 13-1 was manufactured in the same manner as in Example 13-1 except that a cycloolefin copolymer (TOPAS 6013 manufactured by Ticona GmbH) (100 parts by mass) was used in place of the oxygen-absorbing resin composition (12-1). The performance of the obtained vial was evaluated in the same manner as in Example 13-1. The evaluation results are shown in Table 15.

Comparative Example 13-2

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-4). A syringe was manufactured in the same manner as in Example 13-1 except that the oxygen-absorbing resin composition (M-4) was used in place of the oxygen-absorbing resin composition (13-1). The performance of the obtained syringe was evaluated in the same manner as in Example 13-1. The evaluation results are shown in Table 15.

TABLE 15

|  | Example 13-1 | Example 13-2 | Example 13-3 | Example 13-4 | Example 13-5 | Comparative Example 13-1 | Comparative Example 13-2 |
| --- | --- | --- | --- | --- | --- | --- | --- |
| Layer constitution | Three layers | Three layers | Three layers | Three layers | Three layers | Single layer | Three layers |
| Resin used in oxygen-absorbing resin composition | Polyester compound (12-1) | Polyester compound (12-2) | Polyester compound (12-3) | Polyester compound (12-4) | Polyester compound (12-1) + (12-2)[2] | — | Nylon MXD6 |
| Oxygen transmission rate[1] | Detection limit or less | Detection limit or less | Detection limit or less | Detection limit or less | Detection limit or less | 0.024 | Detection limit or less |
| Visibility of content | Slightly hazy (acceptable) | Transparent (acceptable) | Slightly hazy (acceptable) | Transparent (acceptable) | Transparent (acceptable) | Transparent (acceptable) | Hazy (acceptable) |
| Impact resistance | No breakage | No breakage | No breakage | No breakage | No breakage | No breakage | 7 products are broken |
| Elution test (μg/ml) | Detection limit or less | Detection limit or less | Detection limit or less | Detection limit or less | Detection limit or less | Detection limit or less | 38 |

[1]Unit: mL/(0.21 atm · day · package)
[2]Blend of polyester compound (12-1) (90 parts by mass) and polyester compound (12-2) (10 parts by mass)

As is apparent from Table 15, it was confirmed that the syringes of Examples 13-1 to 13-5 maintain satisfactory oxygen barrier property, visibility of a content and impact resistance after long-term storage, and that the amount of elution from the syringe to the content is small.

Example 14-1

With a polyester compound (10-1) (100 parts by mass), cobalt stearate (II) (0.02 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition (14-1). Subsequently, as shown below, a multilayer injection molded container, i.e., vial, was manufactured by using the oxygen-absorbing resin composition (14-1). Thereafter, the performance of the obtained vial was evaluated in the same manner as in Example 10-1. Furthermore, a storage test of biopharmaceutical of vials was performed in the following manner. The evaluation results are shown in Table 16.

[Manufacturing of Vial]

Under the following conditions, the thermoplastic resin for constituting a resin layer (layer B) was injected from an injection cylinder and then the oxygen-absorbing resin composition (14-1) for constituting an oxygen-absorbing layer (layer A) was injected from another injection cylinder simultaneously with the thermoplastic resin for constituting layer B. Subsequently, a thermoplastic resin for constituting layer B was injected in a necessary amount to fill the cavity of an injection mold to obtain an injection-molded article of a three layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. A cycloolefin copolymer (trade name: TOPAS6013, manufactured by Ticona GmbH) was used as the thermoplastic resin for constituting layer B.

(Shape of Vial)

The whole length of a vial was specified as 89 mm, the outer diameter as 40 imp and the film thickness as 1.8 mm. Note that a vial was manufactured by use of an integrated injection blow molding machine (Type: IBS 85, proving 4 vials, manufactured by UNILOY).

(Molding Conditions for Vial)

Temperature of injection cylinder for layer A: 260° C.
Temperature of injection cylinder for layer B: 280° C.
Temperature of resin flow channel in injection mold: 280° C.
Blowing temperature: 150° C.
Temperature of cooling water for blow mold: 15° C.

[Performance Evaluation of Vial]

(6) Storage Test of Biopharmaceutical (Binding-Rate Measurement Method)

Using an isothermal titration calorimetry, a cell was filled with an antigen solution (5 μm) (FGF1-Mouse, manufactured by BIOLOGICAL Industries Ltd.). While adding an antibody solution (10 μL) dropwise to the cell, the binding rate was measured at 25° C.

(Storage Test)

A vial was filled with 1 cc of ANTI FGF1 monoclonal antibody (mAb1) (manufactured by Wako Pure Chemical Industries Ltd.), which was adjusted to be 50 μm, and stored under the conditions of 8° C. and 50% RH for 180 days. As a solvent, a phosphate buffer (PBS pH 7.4) manufactured by Invitrogen was used. The binding rates in the antibody solution before and after the storage test (for 180 days) were measured by the method mentioned above and an antibody activity retention rate was obtained from the binding rates before and after the storage in accordance with the following expression:

Antibody activity retention rate (%) =(Binding rate in the antibody solution after storage of 180 days/Binding rate in the antibody solution before storage)×100

Examples 14-2 to 14-4

Oxygen-absorbing resin compositions and vials were manufactured in the same manner as in Example 14-1 except that each of the corresponding polyester compounds shown in Table 15 was used in place of the polyester compound (10-1). The performance of the obtained vials was individually evaluated in the same manner as in Example 14-1. The evaluation results are shown in Table 16.

Example 14-5

An oxygen-absorbing resin composition and a vial were manufactured in the same manner as in Example 14-1 except that the polyester compound (10-1) (90 parts by mass) and the polyester compound (10-2) (10 parts by mass) were used in place of the polyester compound (10-1) (100 parts by mass). The performance of the obtained vial was evaluated in the same manner as in Example 14-1. The evaluation results are shown in Table 16.

Comparative Example 14-1

A single-layer vial having the same shape as in Example 14-1 was manufactured in the same manner as in Example 14-1 except that a cycloolefin copolymer (TOPAS 6013 manufactured by Ticona GmbH) (100 parts by mass) was used in place of the oxygen-absorbing resin composition (14-1). The performance of the obtained vial was evaluated in the same manner as in Example 10-1. The evaluation results are shown in Table 16.

Comparative Example 14-2

With nylon MXD6 (S7007, manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 15 kg/h. Melt-kneading was performed at a cylinder temperature of 280° C. and a strand was extruded from an extruder head. After cooling, the strand was pelletized to obtain an oxygen-absorbing resin composition (M-5). A vial was manufactured in the same manner as in Example 14-1 except that the oxygen-absorbing resin composition (M-5) was used in place of the oxygen-absorbing resin composition (10-1). The performance of the obtained vial was evaluated in the same manner as in Example 14-1. The evaluation results are shown in Table 16.

TABLE 16

| | Resin used in Layer A | Resin used in Layer B | Layer constitution | Oxygen transmission rate (30th day)[2] | Appearance after molding | Drop test | Elution test TOC amount (μg/mL) | Antibody activity retention rate (%) |
|---|---|---|---|---|---|---|---|---|
| Example 14-1 | Polyester compound (10-1) | COC | Three layers | Detection limit or less | Slightly whitened in part | No breakage is observed in all containers | Detection limit or less | 72 |
| Example 14-2 | Polyester compound (10-2) | COC | Three layers | Detection limit or less | Transparent | No breakage is observed in all containers | Detection limit or less | 69 |

TABLE 16-continued

| | Resin used in Layer A | Resin used in Layer B | Layer constitution | Oxygen transmission rate (30th day)[2] | Appearance after molding | Drop test | Elution test TOC amount (μg/mL) | Antibody activity retention rate (%) |
|---|---|---|---|---|---|---|---|---|
| Example 14-3 | Polyester compound (10-3) | COC | Three layers | Detection limit or less | Slightly whitened in whole | No breakage is observed in all containers | Detection limit or less | 71 |
| Example 14-4 | Polyester compound (10-4) | COC | Three layers | Detection limit or less | Transparent | No breakage is observed in all containers | Detection limit or less | 73 |
| Example 14-5 | Polyester compound (10-1) + (10-2)[1] | COC | Three layers | Detection limit or less | Transparent | No breakage is observed in all containers | Detection limit or less | 78 |
| Comparative Example 14-1 | COC Single layer | | Single layer | 0.0871 | Transparent | No breakage is observed in all containers | Detection limit or less | 35 |
| Comparative Example 14-2 | Nylon MXD6 | COC | Three layers | Detection limit or less | Slightly whitened in whole | 14 out of 20 containers are broken | 15 | 79 |

[1]Blend of polyester compound (10-1) (90 parts by mass) and polyester compound (10-2) (10 parts by mass)
[2]Unit: mL/(0.21 atm · day · package)

As is apparent from Table 16, it was confirmed that when a biopharmaceutical is stored in the vials of Examples 14-1 to 14-5, satisfactory strength was maintained even after long-term storage and that the amount of elution from the container to the content is small and thus reduction of drug efficacy after storage was suppressed.

Example 15-1

With the polyester compound (1-1) (100 parts by mass), cobalt acetate (II) (0.02 parts by mass in terms of cobalt) was dry-blended. The obtained mixture was supplied to a double-screw extruder having two screws of 37 mm in diameter, at a rate of 15 kg/h. Melt-kneading was performed at a cylinder temperature of 220° C. and a strand was extruded from an extruder head. After cooling, the strand was pelletized to obtain an oxygen-absorbing resin composition (15-1).

Subsequently, under the following conditions, the thermoplastic resin for constituting layer B was injected from an injection cylinder and then the resin composition for constituting layer A was injected from another injection cylinder simultaneously with the thermoplastic resin for constituting layer B. Subsequently, the thermoplastic resin for constituting layer B was injected in a necessary amount to fill a cavity to manufacture an injection molded article (test-tube form parison) constituted of three layers (layer B/layer A/layer B). The total mass of the parison was specified as 25 g and the mass of layer A was specified as 10 mass % based on the total mass of the parison. Note that a polyethylene terephthalate (trade name: BK-2180, manufactured by Japan Unipet) was used as the thermoplastic resin for constituting layer B and the above oxygen-absorbing resin composition (15-1) was used as the resin composition for constituting layer A.
(Shape of Parison)
The whole length of a parison was specified as 95 mm, the outer diameter as 22 mm and the film thickness as 2.7 mm. Note that a parison was manufactured by use of an injection molding machine (Type: M200, proving 4 parisons, manufactured by Meiki Co., Ltd.).
(Molding Conditions for Parison)
Temperature of injection cylinder for layer A: 250° C.
Temperature of injection cylinder for layer B: 280° C.
Temperature of resin flow channel in mold: 280° C.
Temperature of cooling water for mold: 15° C.
The obtained parison was cooled and then subjected to a secondary processing, in which the parison was heated and shaped by biaxial stretching blow molding to manufacture a multilayer bottle (oxygen-absorbing multilayer container).
(Shape of Bottle Obtained by Secondary Processing)
The whole length of a bottle was specified as 160 mm, an outer diameter as 60 mm, an inner volume as 350 mL and a film thickness as 0.28 mm. The draw ratio was specified as 1.9 folds lengthwise and 2.7 folds widthwise. The shape of the bottom was a champagne-bottle type. The base of bottle has a dimple. Note that a blow molding machine (type: EFB 1000ET, manufactured by FRONTIER Inc.) was used for secondary processing.
(Secondary Processing Conditions)
Heating temperature of parison: 100° C.
Pressure of a stretching rod: 0.5 MPa
Primary blow pressure: 0.7 MPa
Secondary blow pressure: 2.5 MPa
Primary blow delayed time: 0.33 sec
Primary blow time: 0.35 sec
Secondary blow time: 2.0 sec
Blow discharge time: 0.6 sec
Mold temperature: 30° C.
The obtained multilayer bottle was filled with wine (350 mL) and a bottle opening was sealed with a cap. The sealed container thus obtained was stored at 30° C. The sealed container was opened at 30th day, 60th day and 90th day to check the taste and flavor of the wine. Note that the taste and flavor of the wine was indicated by an average of evaluations given by 5 testers. The evaluation results are shown in Table 17.

Example 15-2

An oxygen-absorbing resin composition and a multilayer bottle were manufactured in the same manner as in Example 1 except that a polyester compound (1-2) was used in place of the polyester compound (1-1). A storage test was performed in the same manner as in Example 15-1. Evaluation results are shown in Table 17.

Example 15-3

An oxygen-absorbing resin composition and multilayer bottle were manufactured in the same manner as in Example 1 except that a polyester compound (1-3) was used in place of the polyester compound (1-1). A storage test was performed in the same manner as in Example 15-1. Evaluation results are shown in Table 17.

Comparative Example 15-1

A single-layer bottle having the same shape as in Example 15-1 was manufactured in the same manner as in Example 15-1 except that a polyethylene terephthalate (trade name: BK-2180, manufactured by Japan Unipet) (100 parts by mass) was used in place of the oxygen-absorbing resin composition (15-1). Subsequently, the storage test of the obtained single-layer bottle was performed in the same manner as in Example 15-1. The evaluation results are shown in Table 17.

TABLE 17

|  | Polyester compound | Taste and flavor[1] | | |
|---|---|---|---|---|
|  |  | After 30 days | After 60 days | After 90 days |
| Example 15-1 | Polycondensation product of dimethyl tetralin-2,6-dicarboxylate/1,4-butanediol | ◎ | ◎ | ◎ |
| Example 15-2 | Polycondensation product of dimethyl tetralin-2,6-dicarboxylate/ethylene glycol | ◎ | ◎ | ○ |
| Example 15-3 | Polycondensation product of dimethyl tetralin-2,6-dicarboxylate/1,6-hexanediol | ◎ | ◎ | ○ |
| Comparative Example 15-1 | Polyethylene terephthalate | ○ | ○ | x |

[1] ◎ satisfactory, ○ almost satisfactory, x reduced

As is apparent from Table 17, it was confirmed that when wine is stored in the oxygen-absorbing multilayer containers of Examples 15-1 to 15-3 excellent in oxygen-absorbing performance and oxygen barrier property, the taste and flavor of the wine is satisfactorily maintained for a long term. In contrast, in a conventional PET single-layer bottle (Comparative Example 15-1) having no oxygen-absorbing function, the taste and flavor of the wine significantly reduced with the passage of time. From these, it was demonstrated that the oxygen-absorbing multilayer container of the present invention is suitable for storing an alcohol beverage.

Example 16-1

The multilayer bottle obtained in Example 15-1 was filled with an orange fruit juice (350 mL) and a bottle opening was sealed with a cap. The sealed container thus obtained was stored at 30° C. The sealed container was opened at 30th day, 60th day and 90th day to check the taste and flavor and color tone of the orange fruit juice. Note that the taste and flavor of the orange fruit juice was indicated by an average of evaluations given by 5 testers. The evaluation results are shown in Table 18.

Example 16-2

A storage test was performed in the same manner as in Example 16-1 except that the multilayer bottle obtained in Example 15-2 was used. The evaluation results are shown in Table 18.

Example 16-3

A storage test was performed in the same manner as in Example 16-1 except that the multilayer bottle obtained in Example 15-3 was used. The evaluation results are shown in Table 18.

Comparative Example 16-1

A storage test was performed in the same manner as in Example 16-1 except that the single-layer bottle obtained in Comparative Example 15-1 was used. The evaluation results are shown in Table 18.

TABLE 18

|  | Resin used in oxygen-absorbing resin composition | Taste and flavor[1] | | | Color tone[2] | | |
|---|---|---|---|---|---|---|---|
|  |  | After 30 days | After 60 days | After 90 days | After 30 days | After 60 days | After 90 days |
| Example 16-1 | Polyester compound (1-1) | ◎ | ◎ | ○ | ◎ | ◎ | ○ |
| Example 16-2 | Polyester compound (1-2) | ◎ | ○ | ○ | ◎ | ○ | ○ |
| Example 16-3 | Polyester compound (1-3) | ◎ | ◎ | ○ | ◎ | ○ | ○ |
| Comparative Example 16-1 | Polyethylene terephthalate single-layer bottle | ○ | ○ | X | ○ | X | X |

[1] Taste: ◎ satisfactory, ○ almost satisfactory, X reduced
[2] Color tone: ◎ satisfactory, ○ slightly satisfactory, X changed As is apparent from Table 18, it was confirmed that when orange fruit juice is stored in the oxygen-absorbing multilayer containers of Examples 16-1 to 16-3 excellent in oxygen-absorbing performance and oxygen barrier property, the taste and flavor and color tone of the orange fruit juice are satisfactorily maintained for a long term. In contrast, in a conventional PET single-layer bottle (Comparative Example 16-1) having no oxygen-absorbing function, the taste and flavor and color tone of the orange fruit juice significantly reduced with the passage of time. From these, it was demonstrated that the oxygen-absorbing multilayer container of the present invention is suitable for storing a fruit juice and a vegetable juice.

Example 17-1

The multilayer bottle obtained in Example 15-1 was filled with noodle broth (350 mL) and a bottle opening was sealed with a cap. The sealed container thus obtained was stored at 35° C. The sealed container was opened at 30th day, 60th day and 90th day to check the taste and flavor of the noodle broth. Note that the taste and flavor of the noodle broth was indicated by an average of evaluations given by 5 testers. The evaluation results are shown in Table 19.

Example 17-2

A storage test was performed in the same manner as in Example 17-1 except that the multilayer bottle obtained in Example 15-2 was used. The evaluation results are shown in Table 19.

Example 17-3

A storage test was performed in the same manner as in Example 17-1 except that the multilayer bottle obtained in Example 15-3 was used. The evaluation results are shown in Table 19.

Comparative Example 17-1

A storage test was performed in the same manner as in Example 17-1 except that the single-layer bottle obtained in Comparative Example 15-1 was used. The evaluation results are shown in Table 19.

TABLE 19

| | | Taste and flavor[1] | | |
|---|---|---|---|---|
| | Resin used in Layer A | After 30 days | After 60 days | After 90 days |
| Example 17-1 | Polycondensation product of dimethyl tetralin-2,6-dicarboxylate/1,4-butanediol | ⊚ | ⊚ | ⊚ |
| Example 17-2 | Polycondensation product of dimethyl tetralin-2,6-dicarboxylate/ethylene glycol | ⊚ | ⊚ | ⊚ |
| Example 17-3 | Polycondensation product of dimethyl tetralin-2,6-dicarboxylate/1,6 hexanediole | ⊚ | ⊚ | ○ |
| Comparative Example 17-1 | (Polyethylene terephthalate single-layer bottle) | ○ | ○ | x |

[1] ⊚ satisfactory, ○ almost satisfactory, x reduced

As is apparent from Table 19, it was confirmed that when noodle broth is stored in the oxygen-absorbing multilayer containers of Examples 17-1 to 17-3 excellent in oxygen-absorbing performance and oxygen barrier property, the taste and flavor of the noodle broth is satisfactorily maintained for a long term. In contrast, in a conventional PET single-layer bottle (Comparative Example 17-1) having no oxygen-absorbing function, the taste and flavor of the noodle broth significantly reduced with the passage of time. From these, it was demonstrated that the oxygen-absorbing multilayer container of the present invention is suitable for storing broth.

Example 18-1

The multilayer bottle obtained in Example 15-1 was filled with high-quality green tea (350 mL) and a bottle opening was sealed with a cap. The sealed container thus obtained was stored at 35° C. The sealed container was opened at 30th day, 60th day and 90th day to check the taste and flavor of the high-quality green tea. Note that the taste and flavor of the high-quality green tea was indicated by an average of evaluations given by 5 testers. The evaluation results are shown in Table 20.

Example 18-2

A storage test was performed in the same manner as in Example 18-1 except that the multilayer bottle obtained in Example 15-2 was used. The evaluation results are shown in Table 20.

Example 18-3

A storage test was performed in the same manner as in Example 18-1 except that the multilayer bottle obtained in Example 15-2 was used. The evaluation results are shown in Table 20.

Comparative Example 18-1

A storage test was performed in the same manner as in Example 18-1 except that the single-layer bottle obtained in Comparative Example 15-1 was used. The evaluation results are shown in Table 20.

TABLE 20

| | | Taste and flavor[1] | | |
|---|---|---|---|---|
| | Polyester compound | After 30 days | After 60 days | After 90 days |
| Example 18-1 | Polycondensation product of dimethyl tetralin-2,6-dicarboxylate/1,4-butanediol | ⊚ | ⊚ | ⊚ |
| Example 18-2 | Polycondensation product of dimethyl tetralin-2,6-dicarboxylate/ethylene glycol | ⊚ | ⊚ | ⊚ |
| Example 18-3 | Polycondensation product of dimethyl tetralin-2,6-dicarboxylate/1,6-hexanediol | ⊚ | ⊚ | ○ |
| Comparative Example 18-1 | Polyethylene terephthalate | ○ | ○ | x |

[1] ⊚ satisfactory, ○ almost satisfactory, x reduced

As is apparent from Table 20, it was confirmed that when high-quality green tea is stored in the oxygen-absorbing multilayer containers of Examples 18-1 to 18-3 excellent in oxygen-absorbing performance and oxygen barrier property, the taste and flavor of the high-quality green tea is satisfactorily maintained for a long term. In contrast, in a conventional PET single-layer bottle (Comparative Example 18-1) having no oxygen-absorbing function, the taste and flavor of the high-quality green tea significantly reduced with the passage of time. From these, it was demonstrated that the oxygen-absorbing multilayer container of the present invention is suitable for storing teas.

As described in the foregoing, the present invention is not limited to the above embodiments and Examples and can be appropriately modified within the gist of the invention.

Note that the present application claims a priority right based on the following 19 Japanese Patent Applications, the contents of which are incorporated herein by reference.

Japanese Patent Application No. 2011-257821 filed with the Japanese Patent Office on Nov. 25, 2011.
Japanese Patent Application No. 2012-223276 filed with the Japanese Patent Office on Oct. 5, 2012.
Japanese Patent Application No. 2012-224914 filed with the Japanese Patent Office on Oct. 10, 2012.
Japanese Patent Application No. 2012-228313 filed with the Japanese Patent Office on Oct. 15, 2012.
Japanese Patent Application No. 2012-228749 filed with the Japanese Patent Office on Oct. 16, 2012.
Japanese Patent Application No. 2012-229009 filed with the Japanese Patent Office on Oct. 16, 2012.
Japanese Patent Application No. 2012-231790 filed with the Japanese Patent Office on Oct. 19, 2012.
Japanese Patent Application No. 2012-231635 filed with the Japanese Patent Office on Oct. 19, 2012.
Japanese Patent Application No. 2012-231636 filed with the Japanese Patent Office on Oct. 19, 2012.
Japanese Patent Application No. 2012-235091 filed with the Japanese Patent Office on Oct. 24, 2012.
Japanese Patent Application No. 2012-235092 filed with the Japanese Patent Office on Oct. 24, 2012.
Japanese Patent Application No. 2012-235409 filed with the Japanese Patent Office on Oct. 25, 2012.
Japanese Patent Application No. 2012-235248 filed with the Japanese Patent Office on Oct. 25, 2012.
Japanese Patent Application No. 2012-235249 filed with the Japanese Patent Office on Oct. 25, 2012.
Japanese Patent Application No. 2012-237569 filed with the Japanese Patent Office on Oct. 29, 2012.
Japanese Patent Application No. 2012-238926 filed with the Japanese Patent Office on Oct. 30, 2012.
Japanese Patent Application No. 2012-238927 filed with the Japanese Patent Office on Oct. 30, 2012.
Japanese Patent Application No. 2012-238928 filed with the Japanese Patent Office on Oct. 30, 2012.
Japanese Patent Application No. 2012-238929 filed with the Japanese Patent Office on Oct. 30, 2012.

INDUSTRIAL APPLICABILITY

The oxygen-absorbing resin composition etc. of the present invention, since they have excellent oxygen-absorbing performance in a wide range of humidity conditions from low humidity to high humidity, can be widely and effectively used in general technical fields requiring oxygen absorption. Furthermore, since the composition etc. can absorb oxygen regardless of the presence or absence of the moisture content of an article to be packaged and produce no odor after absorption of oxygen, they can be particularly effectively used in e.g., foods, cooking foods, beverages, medicinal products and health foods. Moreover, since an oxygen-absorbing resin composition etc. not responsive to a metal detector can also be provided, they can be widely and effectively applied to uses requiring external inspection of metals, metal pieces, etc. by a metal detector, for example, packaging materials and containers.

The invention claimed is:

1. An oxygen-absorbing resin composition comprising a polyester compound and a transition metal catalyst, wherein the polyester compound has at least one constituent unit having a tetralin ring selected from the group consisting of constituent units represented by the following general formulas (5) to (7):

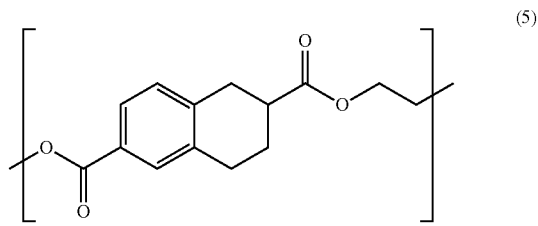

(5)

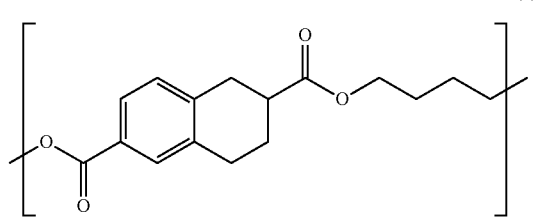

(6)

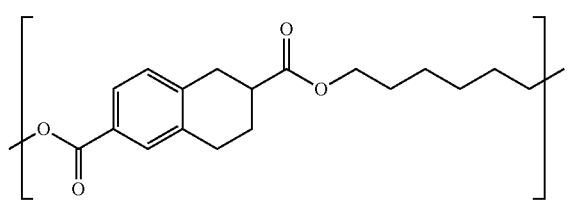

(7)

wherein the oxygen-absorbing resin composition further comprises a catalyst for producing the polyester compound;
wherein the transition metal catalyst is different from the catalyst for producing the polyester compound;
wherein a content rate of the polyester compound is 90 mass % or more based on a total amount of the oxygen-absorbing resin composition;
wherein the transition metal catalyst comprises cobalt and the catalyst for producing the polyester compound comprises at least one metal selected from the group consisting of zinc, lead, cerium, cadmium, manganese, lithium, sodium, potassium, calcium, nickel, magnesium, vanadium, aluminum, titanium, antimony and tin; and
wherein the transition metal catalyst is present in an effective amount to serve as a catalyst for the oxidation reaction of the tetralin ring-containing polyester compound by removing hydrogen at the benzyl position.

2. The oxygen-absorbing resin composition according to claim 1, wherein the transition metal catalyst further comprises at least one transition metal selected from the group consisting of manganese, iron, nickel and copper.

3. The oxygen-absorbing resin composition according to claim 1, wherein the transition metal catalyst is contained in an amount of 0.001 to 10 parts by mass in terms of a transition metal based on 100 parts by mass of the polyester compound.

4. The oxygen-absorbing resin composition according to claim 1, further comprising a thermoplastic resin.

5. The oxygen-absorbing resin composition according to claim 1, further comprising a polyolefin resin.

6. An oxygen-absorbing molded article obtained by molding the oxygen-absorbing resin composition according to claim 1 into a film or sheet form.

7. An oxygen-absorbing multilayer body at least comprising an oxygen-absorbing layer formed of the oxygen-absorbing resin composition according to claim 1 and a resin layer comprising a thermoplastic resin.

8. An oxygen-absorbing multilayer container comprising the oxygen-absorbing multilayer body according to claim 7.

9. An oxygen-absorbing multilayer body comprising at least three layers comprising a sealant layer comprising a thermoplastic resin, an oxygen-absorbing layer formed of the oxygen-absorbing resin composition according to claim 1 and a gas barrier layer comprising a gas barrier substance, in this order.

10. An oxygen-absorbing multilayer container comprising the oxygen-absorbing multilayer body according to claim 9.

11. An oxygen-absorbing paper container obtained by forming a carton from an oxygen-absorbing multilayer body comprising at least four layers comprising an isolation layer comprising a thermoplastic resin, an oxygen-absorbing layer formed of the oxygen-absorbing resin composition according to claim 1, a gas barrier layer comprising a gas barrier substance and a paper substrate layer, in this order.

12. An oxygen-absorbing injection-molded article formed of the oxygen-absorbing resin composition according to claim 1.

13. An oxygen-absorbing container obtained by molding the oxygen-absorbing injection-molded article according to claim 12 into a cup or bottle form.

14. The oxygen-absorbing container according to claim 13, wherein the molding is stretch blow molding.

15. An oxygen-absorbing multilayer injection-molded article comprising an oxygen-absorbing layer formed of the oxygen-absorbing resin composition according to claim 1 and a resin layer comprising a thermoplastic resin.

16. An oxygen-absorbing multilayer container obtained by molding the oxygen-absorbing multilayer injection-molded article according to claim 15 into a cup or bottle form.

17. The oxygen-absorbing multilayer container according to claim 16, wherein the molding is stretch blow molding.

18. An oxygen-absorbing medical multilayer molded container having at least three layers including a first resin layer at least comprising a thermoplastic resin, an oxygen-absorbing layer formed of the oxygen-absorbing resin composition according to claim 1 and a second resin layer at least comprising a thermoplastic resin in this order.

19. The oxygen-absorbing medical multilayer molded container according to claim 18, wherein each of the thermoplastic resin of the first resin layer and the thermoplastic resin of the second resin layer is a polyolefin.

20. The oxygen-absorbing medical multilayer molded container according to claim 18, wherein each of the thermoplastic resin of the first resin layer and the thermoplastic resin of the second resin layer is a polyester other than the polyester compound comprising the constituent unit having the tetralin ring.

21. The oxygen-absorbing medical multilayer molded container according to claim 20, wherein the polyester of the first resin layer and the polyester of the second resin layer each are obtained by polycondensation of at least two components of a polyvalent carboxylic acid comprising no tetralin ring and a polyhydric alcohol comprising no tetralin ring.

22. An oxygen-absorbing prefilled syringe made capable of storing a medicinal agent in advance in a sealed condition, and releasing the sealed condition to eject the medical agent at a time of use, wherein the prefilled syringe is formed of a multilayered structure comprising at least three layers including a first resin layer comprising a thermoplastic resin, an oxygen-absorbing layer formed of the oxygen-absorbing resin composition according to claim 1 and a second resin layer comprising a thermoplastic resin, in this order.

23. A method for storing a biopharmaceutical, comprising storing the biopharmaceutical in the oxygen-absorbing medical multilayer molded container according to claim 18.

24. A method for storing an alcohol beverage, comprising storing the alcohol beverage in an oxygen-absorbing multilayer container using an oxygen-absorbing multilayer body in all or a part of the container, wherein the oxygen-absorbing multilayer body at least comprises an oxygen-absorbing layer formed of the oxygen-absorbing resin composition according to claim 1 and a resin layer comprising a thermoplastic resin.

25. A method for storing a fruit juice and/or a vegetable juice, comprising storing the fruit juice and/or the vegetable juice in an oxygen-absorbing multilayer container using an oxygen-absorbing multilayer body in all or a part of the container, wherein the oxygen-absorbing multilayer body at least comprises an oxygen-absorbing layer formed of the oxygen-absorbing resin composition according to claim 1 and a resin layer comprising a thermoplastic resin.

26. A method for storing a broth, comprising storing the broth in an oxygen-absorbing container using an oxygen-absorbing multilayer body in all or a part of the container, wherein the oxygen-absorbing multilayer body at least comprises an oxygen-absorbing layer formed of the oxygen-absorbing resin composition according to claim 1 and a resin layer comprising a thermoplastic resin.

27. A method for storing a liquid-state tea or a paste-state tea, comprising storing the liquid-state tea or paste-state tea in an oxygen-absorbing container using an oxygen-absorbing multilayer body in all or a part of the container, wherein the oxygen-absorbing multilayer body at least comprises an oxygen-absorbing layer formed of the oxygen-absorbing resin composition according to claim 1 and a resin layer comprising a thermoplastic resin.

28. A method for storing a biopharmaceutical, comprising storing the biopharmaceutical in the oxygen-absorbing prefilled syringe according to claim 22.

* * * * *